United States Patent
Sinha

(10) Patent No.: US 10,988,803 B2
(45) Date of Patent: *Apr. 27, 2021

(54) MULTIPLEXED ASSAY FOR QUANTITATING AND ASSESSING INTEGRITY OF CELL-FREE DNA IN BIOLOGICAL FLUIDS FOR CANCER DIAGNOSIS, PROGNOSIS AND SURVEILLANCE

(71) Applicant: Life Genetics Lab, LLC, New Orleans, LA (US)

(72) Inventor: Sudhir Sinha, Metairie, LA (US)

(73) Assignee: Life Genetics Lab, LLC, New Orleans, LA (US)

( * ) Notice: Subject to any disclaimer, the term of this patent is extended or adjusted under 35 U.S.C. 154(b) by 358 days.

This patent is subject to a terminal disclaimer.

(21) Appl. No.: 14/983,397

(22) Filed: Dec. 29, 2015

(65) Prior Publication Data
US 2016/0186239 A1 Jun. 30, 2016

Related U.S. Application Data

(60) Provisional application No. 62/118,666, filed on Feb. 20, 2015, provisional application No. 62/097,400, filed on Dec. 29, 2014.

(51) Int. Cl.
*C12Q 1/68* (2018.01)
*C12Q 1/686* (2018.01)
*C12Q 1/6851* (2018.01)
*C12Q 1/6886* (2018.01)

(52) U.S. Cl.
CPC ........... *C12Q 1/686* (2013.01); *C12Q 1/6851* (2013.01); *C12Q 1/6886* (2013.01)

(58) Field of Classification Search
None
See application file for complete search history.

(56) References Cited

U.S. PATENT DOCUMENTS

| | | | |
|---|---|---|---|
| 8,551,707 B2 | 10/2013 | Oeth et al. | |
| 8,835,110 B2 | 9/2014 | Wang et al. | |
| 2007/0231802 A1* | 10/2007 | Barrett | C12Q 1/6886 435/6.11 |
| 2009/0068660 A1 | 3/2009 | Hoon et al. | |
| 2009/0280479 A1 | 11/2009 | Hoon et al. | |
| 2011/0151465 A1 | 6/2011 | Hoon et al. | |
| 2011/0159502 A1 | 6/2011 | Hoon et al. | |
| 2013/0143213 A1 | 6/2013 | Oliphant et al. | |

FOREIGN PATENT DOCUMENTS

| | | | |
|---|---|---|---|
| WO | 2006128192 A2 | 11/2006 | |
| WO | WO 2006/128192 | * 11/2006 | |
| WO | 2011153254 A2 | 12/2011 | |
| WO | 2012048113 A2 | 4/2012 | |
| WO | 2014143616 A1 | 9/2014 | |
| WO | 2014201092 A1 | 12/2014 | |

OTHER PUBLICATIONS

Hartman et al. (Molecular and Cellular Probes 19 (2005) 51-59) (Year: 2005).*
Breitback et al. (2014) Direct Quantification of Cell-Free, Circulating DNA from Unpurified Plasma. PLoS One 9(3): e87838, 10 pages) (Year: 2014).*
Pineda et al. (Forensic Science International: Genetics 13 (2014) 224-235, published online Aug. 18, 2014) (Year: 2014).*
Hao et al., "Circulating cell-free DNA in serum as a biomarker for diagnosis and prognostic prediction of colorectal cancer", British Journal of Cancer (Oct. 14, 2014); 111(8), pp. 1482-1489, (Feb. 26, 2002), www.bjcancer.com, DOIL10.1038/bjc.2014.470, UK.
Garcia-Olmo et al., "Circulating nucleic acids in plasma and serum (CNAPS): applications in oncology", OncoTargets and Therapy (2013), vol. 2016:6, pp. 819-832, DOI: http://dx.doi.org/10.2147/OTT.S44668.
Nicklas et al., "Development of an Alu-based, Real-Time PCR Method for Quantitation of Human DNA in Forensic Samples", J Forensic Sci, Sep. 2003, vol. 48, No. 5, Paper ID JFS2002414_485, pp. 936-944, West Conshohocken, PA.
Yu et al., "Recent Advances in Clinical Applications of Circulating Cell-free DNA Integrity", Lab Med. 2014; 45 (1): 6-12, US, www.medscape.com/viewarticle/823418_print.
Sunami et al., "Multimarker Circulating DNA Assay for Assessing Blood of Prostate Cancer Patients", Clinical Chemistry (2009), vol. 55:3, pp. 559-567, USA.
Roth et al., "Circulating microRNAs as blood-based markers for patients with primary and metastatic breast cancer", Breast Cancer Research (2010) vol. 12, Issue 6:R90, Germany, http://breast-cancer-research.com/content/12/6/R90.

(Continued)

*Primary Examiner* — Juliet C Switzer
(74) *Attorney, Agent, or Firm* — Crowell & Moring LLP

(57) ABSTRACT

A retrotransposable element based multiplexed qPCR assay to robustly quantitate and distinguish cell free DNA integrity and concentration in blood plasma and serum is described. The multiplexed system for characterizing cancer in humans includes a sample of serum, plasma, urine, or other biological fluid, the sample comprising cell free DNA, the cell free DNA comprising long and short retrotransposable element targets and an added internal positive control, the long and short targets being independent of each other, a distinctly labeled TaqMan probe corresponding to each target, a forward primer and a reverse primer corresponding to each target, a DNA standard for generating standard curves, a qPCR system for amplifying the targets and a qPCR data analysis system. The assay provides an accurate, minimally-invasive, rapid, high-throughput, and cost-effective method with the potential to complement or replace existing methods for detection, diagnosis, prognosis, treatment monitoring and/or surveillance of cancer, thereby improving patient outcomes.

19 Claims, 36 Drawing Sheets

Specification includes a Sequence Listing.

(56) References Cited

OTHER PUBLICATIONS

Agostini et al., "Circulating Cell-Free DNA: A Promising Marker of Pathologic Tumor Response in Rectal Cancer Patients Receiving Preoperative Chemoradiotherapy", Annals of Surgical Oncology, 2011, 18:2461-2468, DOI 10.1245/s10434-011-1638-y, USA.

Mead et al., "Circulating tumour markers can define patients with normal colons, benign polyps, and cancers", British Journal of Cancer (2011) 105, pp. 239-245, UK.

Shen et al., "Diagnosis of lung cancer in individuals with solitary pulmonary nodules by plasma microRNA biomarkers", BioMed Central Cancer (2011), 11:374, pp. 1-9, Baltimore, MD USA, http://www.biomedcentral.com/1471-2407/11/374.

Hassanein et al., "The State of Molecular Biomarkers for the Early Detection of Lung Cancer", Cancer Prev Res (Phila), Aug. 2012; 5(8): 992-1006. doi:10.01158/1940-6207.CAPR-11-0441, Nashville, TN.

Schwarzenbach et al., "Cell-free nucleic acids as biomarkers in cancer patients", Nature Reviews Cancer, May 12, 2011; doi:10.1038/nrc3066, pp. 426-437, USA.

Umetani et al., "Increased Integrity of Free Circulating DNA in sera of Patients with Colorectal or Periampullary Cancer: Direct Quantitative PCR for ALU Repeats", Clinical Chemistry (2006), 52:6, pp. 1062-1069, USA.

Umetani et al., "Prediction of Breast Tumor Progression by Integrity of Free Circulating DNA in Serum", Journal of Clinical Oncology, vol. 24, No. 26, Sep. 10, 2006, pp. 4270-4276, USA.

* cited by examiner

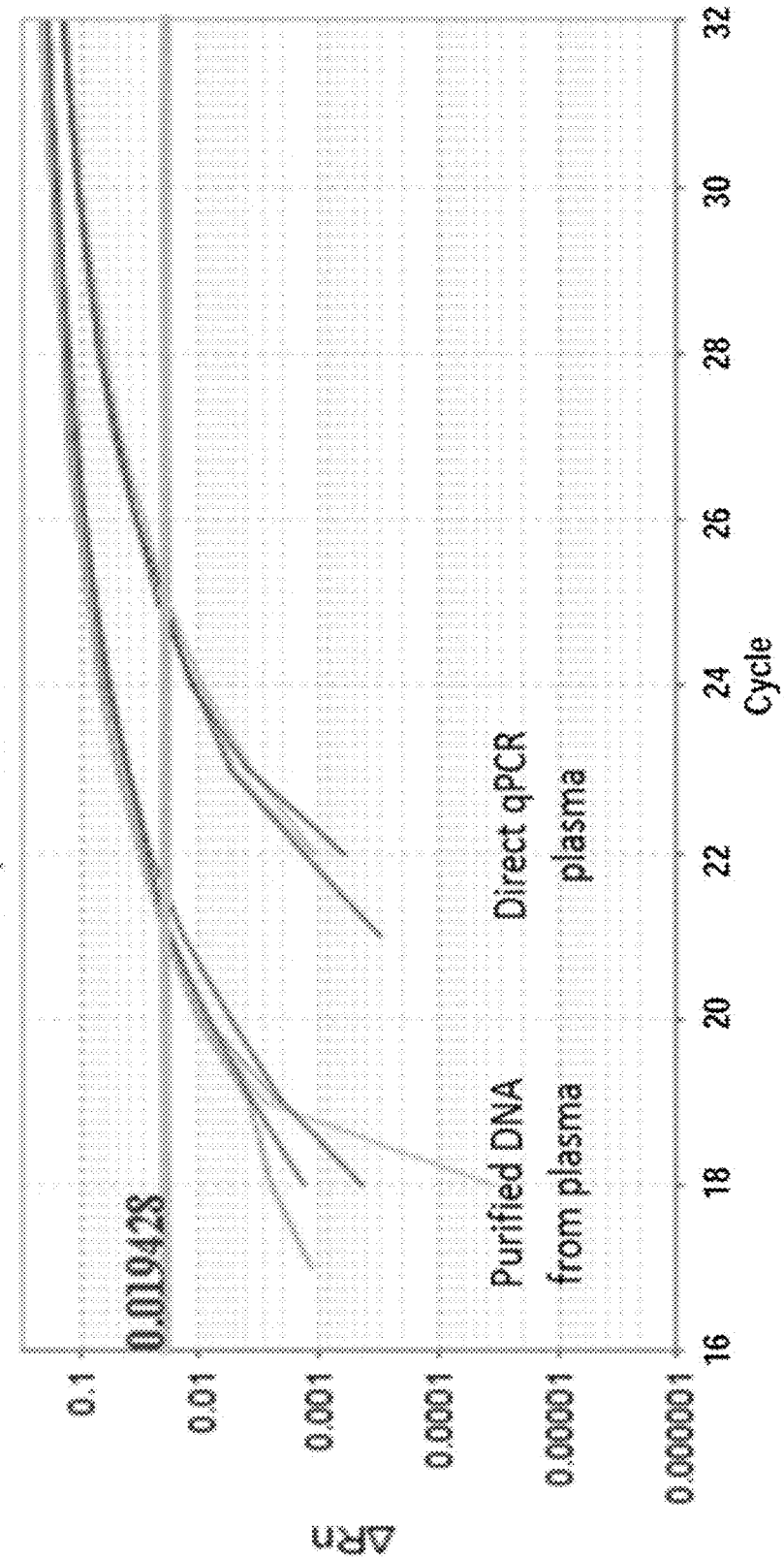

MULTIPLEXED ASSAY FOR QUANTITATING AND ASSESSING INTEGRITY OF CELL-FREE DNA IN BIOLOGICAL FLUIDS FOR CANCER DIAGNOSIS, PROGNOSIS AND SURVEILLANCE

CLAIM OF PRIORITY

This application makes reference to, incorporates the same herein, and claims all benefits accruing under 35 U.S.C. §119(e) from an application for MULTIPLEXED ASSAY FOR QUANTITATING AND ASSESSING INTEGRITY OF CELL-FREE DNA IN BIOLOGICAL FLUIDS FOR CANCER DIAGNOSIS, PROGNOSIS AND SURVEILLANCE, earlier filed in the United States Patent and Trademark Office as a provisional application under 35 U.S.C. § 111(b) on 29 Dec. 2014 and duly assigned Ser. No. 62/097,400 and from another application of the same title earlier filed in the United States Patent and Trademark Office as a provisional application under 35 U.S.C. § 111(b) on 20 Feb. 2015 and duly assigned Ser. No. 62/118,666.

SEQUENCE LISTING

Sequences are submitted concurrently with this application via EFS-Web as an ASCII text file named P60279_Seqprimerprobe122915.txt, created on 29 Dec. 2015, the file having a size of 7000 bytes. All sequences in the latter ASCII text file are hereby incorporated by reference.

BACKGROUND OF THE INVENTION

1. Field of the Invention

A multiplexed quantitative polymerase chain reaction (qPCR) process for determining the integrity and concentration of cell free DNA in blood plasma, blood serum, urine, or other biological fluids for cancer diagnosis, prognosis and surveillance.

2. Impetus for the Invention

Cancer is one of the leading causes of death in developed, and increasingly also developing, nations. According to the World Health Organization, in 2012, over 14 million new cases were reported and over 8 million people died worldwide (Atlanta: American Cancer Society, Cancer Facts & Figures, 2014). Colorectal cancer (CRC) is the third most commonly diagnosed cancer and third-leading cause of cancer deaths in the United States. In 2014, nearly 140,000 diagnoses and 50,000 deaths are expected in the U.S. (Atlanta: American Cancer Society, Colorectal Cancer: Facts & Figures 2014-2016). CRC is often curable if detected early, and outcomes can be improved with post-treatment monitoring and surveillance for recurrence.

Effective cancer management depends on early diagnosis, accurate tumor staging, and consistent monitoring.

SUMMARY OF THE INVENTION

The present application describes a process whereby retrotransposon interspersed element ('RE') markers can be simultaneously assayed in a single, highly sensitive multiplex qPCR reaction, with the inclusion of an internal positive control to monitor the presence of PCR inhibitors potentially present in blood serum or plasma. This method enables development of an accurate, rapid, affordable, minimally invasive, high throughput, cost effective clinical test with the potential to complement or replace existing procedures and improve cancer diagnosis, prognosis, surveillance and/or treatment monitoring.

Accordingly, one object of the invention is to develop a multiplexed qPCR method that accurately quantitates cfDNA in biological fluids including blood plasma or serum.

Another object of the invention is to develop a multiplexed qPCR method that accurately provides a determination of the extent of fragmentation or integrity of cfDNA in biological fluids including blood plasma or serum.

Another object of the invention is to develop a three target (one short RE target, one long RE target, and one internal positive control synthetic target) multiplex RE-qPCR assay to accurately and robustly obtain cfDNA concentration and DNA integrity values from normal and CRC patients by direct qPCR from plasma/serum samples without DNA purification.

One embodiment of the invention takes the form of a multiplexed method to quantitate the integrity of circulating cell free human DNA, comprising providing a sample of serum, plasma, urine, or other biological fluid, the sample comprising cell free human DNA, the cell free human DNA comprising a short nucleic acid fragment including less than 180 bp and a long nucleic acid fragment including more than 180 bp, the short nucleic acid fragment and the long nucleic acid fragment being retrotransposable element genomic targets that are independent of each other, using a quantitative polymerase chain reaction (qPCR) method to separately and simultaneously quantitate the short nucleic acid fragment and the long nucleic acid fragment, obtaining for each quantitated nucleic acid fragment a threshold cycle number, comparing each threshold cycle number with a standard curve to determine for each quantitated nucleic acid fragment a quantity of the DNA fragment that was present in the sample, and calculating a ratio of the quantity of the long nucleic acid fragment to the quantity of the short nucleic acid fragment, but the present invention is not limited thereto.

In certain embodiments of the multiplexed method of the present invention, the retrotransposable element genomic targets may be each independently an interspersed ALU, SVA, or LINE element. In certain embodiments, these retrotransposable element genomic targets may each have a copy number in excess of 1000 copies per genome.

Some embodiments of the multiplexed method of the present invention further comprise a step of adding a synthetic DNA sequence as an internal positive control prior to the using step, quantitating the internal positive control in the using step, and utilizing the quantitative internal positive control result in the comparing step to improve the accuracy and reliability of the comparing step.

In embodiments of the multiplexed method of the present invention, the use of an internal positive control enables a determination of the concentration of cell free DNA in the sample.

In some embodiments of the multiplexed method of the present invention, the sample of serum, plasma, urine, or other biological fluid may be placed in a single tube, and the qPCR reactions for quantitation of the nucleic acid fragments may be carried out in that same single tube.

In some embodiments of the multiplexed method of the present invention, the ratio of the quantity of the long nucleic acid fragment to the quantity of the short nucleic acid fragment may serve as an integrity value of circulating cell free DNA for diagnostic applications. These diagnostic applications may include one or more of the detection, diagnosis, prognosis, treatment monitoring, and surveillance of cancer.

In certain embodiments, the multiplexed method of the present invention may include a step of deactivating or eliminating proteins that bind to the short nucleic acid fragment or the long nucleic acid fragment. This may be done by mixing the sample with a buffer including a surfactant and chelating agent, enzymatically digesting the protein, then using heat to deactivate and insolubilize the digested protein, followed by centrifugation. Alternatively, dilution of the sample using 40 parts sterile water to one part sample by volume may have the effect of deactivating or eliminating these proteins.

In certain embodiments, the multiplexed method of the present invention may include a step of providing a hybridization probe corresponding to the short nucleic acid fragment and a probe corresponding to the long nucleic acid fragment. In certain embodiments, each probe may include an observable label. In some embodiments, the observable labels may be fluorescent labels that are distinct from each other.

In some embodiments, the multiplexed method of the present invention may include a step of separating amplification products obtained from the qPCR reaction using electrophoresis.

In some embodiments, the multiplexed method of the present invention may include a step of determining an optimum temperature for the qPCR reaction.

The multiplexed method of the present invention may include a sample that comes from an individual who is suffering from cancer or who is at risk for developing cancer.

In certain embodiments, the present invention may take the form of a multiplexed system for characterizing cancer in humans including a sample of serum, plasma, urine, or other biological fluid, the sample comprising cell free DNA, the cell free DNA comprising two retrotransposable element targets, the first target being a multi-copy retrotransposon having less than 180 bp, the second target being another multi-copy retrotransposon having more than 180 bp, the first target and the second target being independent of each other, the sample further comprising an added third target, the third target being an internal positive control comprising synthetic DNA; a TaqMan probe corresponding to each of the first target, the second target and the third target, each probe comprising a detectable label that is distinct from the labels incorporated into the other probes; a forward primer and a reverse primer for amplifying each of the first target, the second target and the third target; a DNA standard for generating standard curves for the first target and the second target; a qPCR system for simultaneously amplifying the first target, the second target and the third target and for producing a threshold cycle number for each target; and a qPCR data analysis system for producing DNA quantitation values for each target by interpolation using threshold cycle numbers and linear standard curves and for using the DNA quantitation values to produce an indication of the integrity of the cell free DNA.

In other embodiments of the multiplexed system of the present invention, the first target is a multi-copy retrotransposon having less than N bp, and the second target is another multi-copy retrotransposon having more than N bp, where N is 125 bp, 130 bp, 140 bp, 150 bp, 160 bp, 170 bp, 190 bp, 200 bp, or 205 bp.

In some embodiments of the multiplexed system of the present invention, the detectable labels corresponding to the first target, the second target and the third target may be fluorophores that are distinct from each other.

In some embodiments of the multiplexed system of the present invention, the qPCR system may amplify the first target, the second target and the third target without prior purification of the first, second, or third DNA targets.

In some embodiments, the multiplexed system of the present invention may include DNA polymerase, and the qPCR system may amplify a template DNA fragment of each of the first target, the second target and the third target after deactivation or elimination of protein bound to at least one of a template DNA and DNA polymerase.

In certain embodiments of the multiplexed system of the present invention, the retrotransposable element genomic targets may be each independently an interspersed ALU, SVA, or LINE element.

In certain embodiments of the multiplexed system of the present invention, the first target may be an ALU element having a size selected from the group consisting of 80 bp, 119 bp, 120 bp and 123 bp, and the second target may be an SVA element having a size selected from the group consisting of 207 bp, 257 bp, 265 bp, 290 bp, 355 bp, 367 bp, 399 bp and 411 bp.

In some embodiments of the multiplexed system of the present invention, the first target may be an ALU element of the Yb8 subfamily having a size of about 80 bp, and the second target may be an SVA element having a size of about 207 bp, but the first target and the second target are not limited thereto. In other embodiments, the first target Yb8 ALU element may have a size of about 119 bp, about 120 bp, or about 123 bp, and the second target SVA element may have a size of about 257 bp, about 265 bp, about 290 bp, about 355 bp, about 367 bp, about 399 bp, or about 411 bp. Embodiments of the present invention may be formed from any possible pairing of a suitable first target ALU element with a suitable second target SVA element.

In some embodiments of the multiplexed system of the present invention, the third target, which is an internal positive control comprising synthetic DNA, may have a size of about 172 base pairs, but the size of the internal positive control sequence is not limited thereto.

In some embodiments of the multiplexed system of the present invention, the first retrotransposable element target and the second retrotransposable element target may each have a copy number in excess of 1000 copies per genome.

In some embodiments of the multiplexed system of the present invention, one or more additional retrotransposable element targets found in the cell free DNA may be added to the multiplex. Such multiplexed systems may further comprise a distinctly labeled TaqMan probe corresponding to each target and a forward and reverse primer set corresponding to each target, the qPCR system simultaneously amplifying each target.

In some embodiments, the present invention may include a kit for determining concentration and integrity of cell free DNA in biological fluids, the kit comprising a set of primers corresponding to each of a short retrotransposable element genomic target sequence and a long retrotransposable element genomic target sequence, the short retrotransposable element being shorter than 180 bp in length, the long retrotransposable element being longer than 180 bp in length, the short retrotransposable element and the long retrotransposable element being independent of each other, each set of primers comprising a forward primer and a reverse primer; a synthetic genomic sequence suitable for use as an internal positive control; and one or more reagents for performing quantitative real-time polymerase chain reaction (PCR) amplification.

In some embodiments, the kit of the present invention may include a vacuum-filled test tube for collecting a sample of whole blood or an anticoagulant-treated tube for collecting a sample of whole blood and producing a plasma sample.

In some embodiments, the kit of the present invention may include a probe corresponding to the short target sequence and/or a probe corresponding to the long target sequence. Each probe may include an observable label. The observable labels may be fluorescent organic dyes.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows qPCR amplification plots for blood plasma samples, showing behavior both for purified DNA and for the case of using direct qPCR. The horizontal lines show the automatic cycle threshold setting.

DETAILED DESCRIPTION OF THE INVENTION

Figure 1:
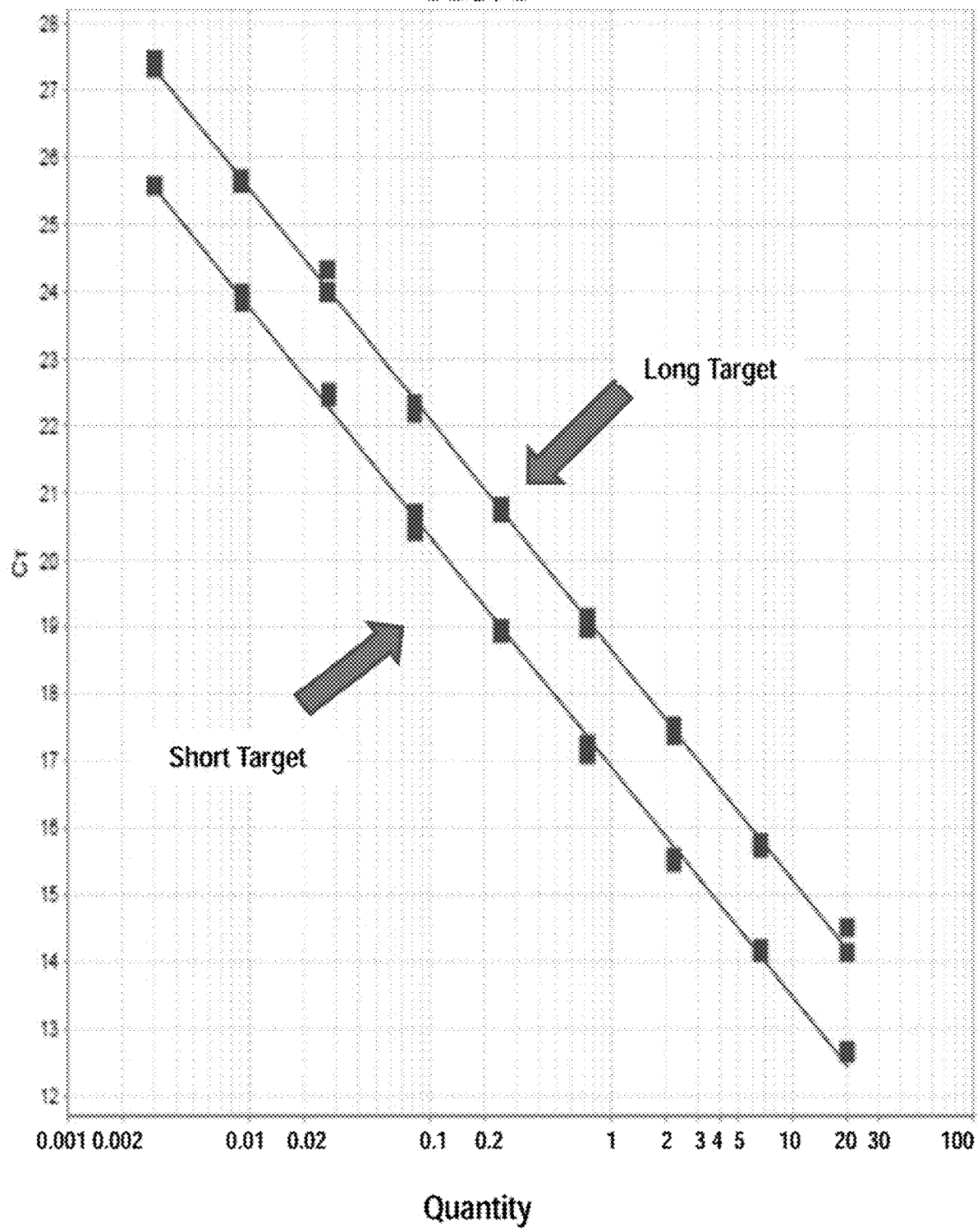
FIG. 1 shows standard curves for long and short targets of a three target multiplex RE-qPCR assay for cfDNA concentration and DNA integrity in a biological fluid sample.

Many current diagnostic procedures are invasive, expensive and unpleasant. In multiple recent published studies, circulating cell-free DNA (cfDNA) concentration and integrity (fragmentation pattern) has shown promise as a highly sensitive and specific, minimally invasive blood biomarker for multiple cancer types (see, e.g., Hao, T B, et al., *Circulating cell-free DNA in serum as a biomarker for diagnostic and prognostic prediction of colorectal cancer*, British Journal of Cancer 2014: 1-2, doi 10.1038/bjc.2014.470; Gonzalez-Masia, et al., *Circulating nucleic acids in plasma and serum (CNAPS): applications in oncology*, Onco. Targets Ther. 6:819-832 (2013); Yu, J, et al., *Recent advances in clinical applications of circulating cell-free DNA integrity*, Lab Med. 45(1): 6-12 (2014)). A number of these studies have indicated the utility of a highly sensitive assay to measure cfDNA integrity (fragmentation pattern) and concentration based on quantitation of an ALU element, the most common type of retrotransposable elements (RE) in the human genome (Table 1). RE-based methods for quantitating DNA are attractive due to their superior sensitivity (multi-copy representation in the genome) and robustness.

The most commonly employed cfDNA integrity/concentration assessment method, the ALU 247/115 bp index, targets sequences of a single ALU element, and thus the two fragments analyzed are not independent. This precludes use of these targets in a single multiplexed assay for maximum accuracy, efficiency and practical clinical use. This prior art method poses several particular problems. First, evaluating the first target and the second target separately rather than multiplexing into a single reaction mixture introduces well-to-well variability into the results. Every PCR reaction is somewhat different from every other PCR reaction, and experimental variation in set-up steps, such as variation in pipetting volumes, introduces error and can impact the results. Secondly, data presented herein demonstrates that the primers used in prior art studies to amplify these specific 247 bp/115 bp targets show poor primer specificity, with false signals being generated from non-template controls. Thirdly, single-plex amplification prohibits the incorporation of an internal PCR control. The use of an internal PCR control is critical for confirming the success of the reaction and for providing confidence that other experimental factors such as the presence of PCR inhibitors in the sample have not interfered. Additionally, single-plex amplification of each target is cumbersome, more labor-intensive and less cost effective than is running a multiplexed amplification.

One of the cancer types studied using cell free DNA integrity is colorectal cancer (CRC). The current gold-standard for CRC diagnosis and staging is colonoscopy and subsequent histological examination. While specific and accurate, colonoscopy is invasive, expensive, and poses some risks; all of which decrease patient compliance to screening recommendations and discourage routine monitoring. In CRC and a few other cancer types, tissue biopsy is supplemented with detection of cancer protein biomarkers in blood serum, e.g. carcinoembryonic antigen (CEA). Such assays have the significant advantage of being minimally invasive and also do not require immediate localization of the tumor. Nevertheless, these assays suffer from limited sensitivity. CEA, one component of the current standard of care for CRC post-treatment monitoring, has relatively low sensitivity and specificity for early (stages I and II) and late (stages III and IV) disease (early: 36% sensitivity and 87% specificity; late: 74% sensitivity and 83% specificity) (Fakih, M. G.; Padmanabhan, A., *CEA Monitoring in Colorectal Cancer*, Oncology 20(6): 579-587 (2006)). Given this performance, CEA is not recommended for CRC diagnosis according to the National Comprehensive Cancer Network guidelines for CRC (Ms-PSEE, Hunt, S., NCCN, Clinical Practice Guidelines in Oncology (NCCN Guidelines®) Colon Cancer, 2013).

cfDNA: A Brief Overview of Biology and Physiology

Characterization of cell-free DNA (cfDNA), DNA found in circulation in human blood plasma and serum, has emerged as an exciting prospect for a new generation of blood-based tools for cancer detection, monitoring and surveillance. Nucleic acid circulation in human blood plasma was first reported in 1948 (Mandel P; Metais P., *Les acides nucleiues du plasma sanguin chez l'Homme*. C. R. Acad. Sci. Paris 142: 241-243 (1948)). Leon, et al., (1977) were the first to report that mean cfDNA levels were significantly higher in the serum of patients with malignant cancers versus healthy patients (Leon, S A; Shapiro, B; Sklaroff, D M; Yaros, M J, *Free DNA in the Serum of Cancer Patients and the Effect of Therapy*, Cancer Research 1977: 646-650). In the past two decades, many details of cfDNA biology, and the relationship between cfDNA and disease, have been elucidated. A brief primer of these studies is provided below, with emphasis on aspects of cfDNA biology that are pertinent to our specific application.

Circulating cfDNA is derived from both the nuclear and mitochondrial genomes of normal and tumor cells (Mandel and Matais 1948, referenced supra; Zhong, S; Ng, M C Y; Lo, Y M D; Chan, J C N; Johnson, P J; Kong H., *Presence of mitochondrial tRNA$^{Leu(UUR)}$ A to G 3243 mutation in DNA extracted from serum and plasma of patients with type 2 diabetes mellitus*, J. Clin. Pathol. 53: 466-469 (2000)). Both coding and noncoding portions of the genome are represented among circulating cfDNA (Bettegowda, C, et al., *Detection of Circulating Tumor DNA in Early- and Late-Stage Human Malignancies*, Sci. Transl. Med. 6(224): 224ra24 (2014), doi:10.1126/scitranslmed.3007094.Detection). Although several mechanisms are believed to contribute to the circulating cfDNA pool, including spontaneous release of free, exosome-encapsulated, and microvesicle-encapsulated DNA into the bloodstream, cell death is the major generator of circulating cfDNAs (Jahr, S; Hentze, H; Englisch, S; Hardt, D; Fackelmayer, F O; Hesch, R, *DNA Fragments in the Blood Plasma of Cancer Patients: Quantitations and Evidence for Their Origin from Apoptotic and Necrotic Cells*, Cancer Research 61:1659-1665(2001)). Cell turnover in normal cells is ordinarily due to apoptosis, which results in stereotyped sized fragments of DNA: a monomeric form composed of ~180 bp fragments of DNA and associated nucleosomes, and reduced amounts of oligomeric forms. Id. Alternatively, tumor cells turn over using a diversity of cell death pathways, not only apoptosis, but also necrosis, autophagy, and mitotic catastrophe (Jin, Z; El-Deiry, W S, *Overview of Cell Death Signaling Pathways*, Cancer Biology & Therapy 4(2): 139-163 (2005), available at http://flybay.net/journals/cbt/jin4-2.pdf (accessed 15 Dec. 2014)). Non-apoptotic pathways non-specifically and incompletely degrade DNA, generating substantially longer DNA fragments, up to 21 kilobases in the case of necrosis (Jahr, S., cited supra). Differences in the rate of cell death and type of cell death pathway utilized between normal and cancer cells lead to distinct characteristics of cfDNA pools that distinguish patients with and without cancer. cfDNAs have variable half-life within the body, ranging from minutes to hours (Lo Y M D; Zhang J; Leung T N; Lau T K; Chang A M Z; Hjelm N M, *Rapid clearance of fetal DNA from maternal plasma*, Am. J. Hum. Genet. 64: 218-224(1999); Emlen W; Mannik M., *Effect of DNA size and strandedness on the in vivo clearance and organ localization of DNA*, Clin. Exp. Immunol. 56(1): 185-192 (1984)). Short half-life implies that circulating cfDNA levels provide a dynamic measure of the physiological and pathological state of an individual. Finally, there is evidence that a small fraction of circulating cfDNA from blood is able to pass the kidney barrier and enter urine. These cfDNAs are called 'trans-renal' cfDNAs (Su Y-H, et al., *Human Urine Contains Small, 150 to 250 Nucleotide-Sized, Soluble DNA Derived from the Circulation and May Be Useful in the Detection of Colorectal Cancer*, J. Molecular Diagnostics, 6(2): 101-107 (2004); Botezatu I, et al., *Genetic analysis of DNA excreted in urine: A new approach for detecting specific genomic DNA sequences from cells dying in an organism*, Clin. Chem. 46(8): 1078-1084 (2000)). The specific physiology of trans-renal cfDNAs awaits detailed exploration.

cfDNA and Cancer

Circulating cfDNAs from patients with and without cancer differ in a number of ways. Tumor genomes harbor specific genetic and epigenetic alterations that distinguish them from normal genomes, and these differences are reflected in cfDNAs. Nonspecific characteristics of cfDNA, such as concentration and integrity, differ between cancer patients and control subjects due to the specific mechanisms of cfDNA release into the blood by normal versus tumor cells. cfDNA concentration and integrity have often been found to be elevated in patients with cancer due to high rate of tumor cell death (reviewed in Schwarzenbach H; Hoon D S B; Pantel K., *Cell-free nucleic acids as biomarkers in cancer patients*, Nature Reviews Cancer 11: 426-437 (2011), doi:10.1038/nrc3066; González-Masiá, J A; García-Olmo, D; García-Olmo, D C, *Circulating nucleic acids in plasma and serum (CNAPS): Applications in oncology*, Onco. Targets. Ther. 6: 819-832 (2013)). However, absolute cfDNA concentration significantly varies among currently employed assays, significantly hampering the ability to compare results across studies. There is currently no standardized, validated, commercially available cfDNA concentration and integrity assay. There are no reports in the prior art of using a multiplexed qPCR system of the kind described herein for accurate simultaneous measurement of concentration and integrity of Cell Free DNA.

cfDNA integrity has emerged as a particularly promising method for detecting and monitoring cancer. This method is based on the fact that normal and tumor cells undergo different types of cell death, leading to different size cfDNA products in the blood, as explained above. cfDNA in patients with cancer is expected to be, on average, longer, and therefore of higher integrity than in patients without cancer. While some studies established an integrity index based on one or a small number of genes, Umetani, et al., pioneered the use of an ALU retrotransposon-based integrity index for cfDNA assessment (Umetani N, et al., *Increased integrity of free circulating DNA in sera of patients with colorectal or periampullary cancer: Direct quantitative PCR for ALU repeats*, Clin. Chem. 52(6): 1062-1069 (2006), doi:10.1373/clinchem.2006.068577; denoted Umetani 2006b in Table 1; Hoon, et al., *Use of free circulating DNA for diagnosis, prognosis, and treatment of cancer funding*, US 2009/0280479 A1). They defined integrity as the ratio of a 247 bp fragment (ALU 247) versus 115 bp fragment (ALU 115) of a single ALU element. ALU 115 measures the total cfDNA concentration and ALU 247 measures tumor-derived cfDNA. Using their ALU 247/115 integrity index, Umetani, et al., demonstrated that DNA integrity and concentration were significantly higher in patients with CRC, periampullary cancer, and breast cancer compared to healthy controls (Id.; Umetani, N, et al., *Prediction of breast tumor progression by integrity of free circulating DNA in serum*, J. Clin. Oncol. 24(26): 4270-4276 (2006), doi:10.1200/JCO.2006.05.9493; denoted Umetani 2006a in Table 1). They also showed that disease prognosis was predicted by cfDNA integrity in each of these cases. Subsequently, several authors have reported significant increases in cfDNA integrity in patients with cancer versus those without using the ALU 247/115 measure (summarized in Table 1 below).

The ALU-based method is highly sensitive due to the multi-copy nature of the ALU target (discussed more extensively below). Importantly, this enables development of a rapid, high-throughput, and cost effective assay due to the relative simplicity of the test. It utilizes real-time PCR, a standard DNA quantitation method compatible with multiple commonly used instrument platforms.

TABLE 1

Detection of cfDNA integrity using the ALU 247/115 index in different cancer types from serum or plasma samples. Area Under the Curve (AUC) from Receiver Operator Characteristic (ROC) curves presented. AUC assess diagnostic potential and ranges from 0.5 (not useful) to 1.0 (most useful).

| Cancer Type | Comparison Groups | AUC | Reference |
| --- | --- | --- | --- |
| Prostate | Benign prostate hyperplasia vs. prostate cancer | 0.91 | Feng 2013 |
| Colorectal | Healthy control (clean colon) vs. rectal cancer | 0.91 | Agostini 2011 |
| Colorectal | Normal control vs. primary colorectal cancer | 0.89 | Hao 2014 |
| Pleural effusion | No malignant pleural mesothelioma vs. malignant pleural effusion | 0.823 | Sriram 2012 |
| Breast | No lymph node metastasis vs. lymph node metastasis | 0.81 | Umetani 2006a |

TABLE 1-continued

Detection of cfDNA integrity using the ALU 247/115 index in different cancer types from serum or plasma samples. Area Under the Curve (AUC) from Receiver Operator Characteristic (ROC) curves presented. AUC assess diagnostic potential and ranges from 0.5 (not useful) to 1.0 (most useful).

| Cancer Type | Comparison Groups | AUC | Reference |
|---|---|---|---|
| Periampullary | Healthy control vs. periampullary cancer (st. I-IV) | 0.8 | Umetani 2006b |
| Breast | Healthy control vs. preoperative breast cancer (st. II-IV) | 0.79 | Umetani 2006a |
| Colorectal | Healthy control vs. colorectal cancer (st. I-IV) | 0.78 | Umetani 2006b |
| Colorectal | Normal control vs. colorectal cancer | 0.772 | Mead 2011 |
| Pleural effusion | No malignant pleural effusion vs. malignant pleural effusion | 0.766 | Sriram 2012 |
| Colorectal | Response vs. non-response to chemoradiotherapy | 0.76 | Agostini 2011 |
| Hepatocellular Carcinoma | Hepatocellular carcinoma (HCC) vs. HCC with Hepatitis C viral infection | 0.75 | El-Shazly 2010 |
| Colorectal | Healthy control vs. colorectal cancer | 0.74 | Leszinski 2014 |

Overview of Retrotransposable Elements (REs)

Retrotransposable Elements (REs) are mobile element insertion polymorphisms that are essentially homoplasy-free characters, identical by descent and easy to genotype (reviewed in Batzer M A; Deininger, P L, *Alu repeats and human genomic diversity*, Nat. Rev. Genet. 3(5): 370-9 (2002), doi:10.1038/nrg798). ALUs are REs that are approximately 300 bp insertions and are distributed throughout the human genome in large copy number. In addition to the major retrotransposon families, REs include smaller families of transposons such as SVA or long interspersed element ("LINE"). SVA elements, named after its main components, short interspersed element ("SINE"), variable number tandem repeat ("VNTR") and Alu element ("ALU"), contain the hallmarks of retrotransposons, in that they are flanked by target site duplications ("TSDs"), terminate in a poly(A) tail and they are occasionally truncated and inverted during their integration into the genome (Ono, M; Kawakami, M; Takezawa, T, *A novel human nonviral retroposon derived from an endogenous retrovirus*. Nucleic Acids Res. 15(21): 8725-8737 (1987); Wang, H, et al., *SVA elements: A hominid-specific retroposon family*, J. Mol. Biol. 354(4): 994-1007 (2005), doi:10.1016/j.jmb.2005.09.085). Long-interspersed Elements (LINE1) are similar to ALU and SVA in that they also contain the hallmarks of retrotransposons and are high copy number, but differ in size, being up to several kilobases in length (Deininger, P L; Batzer, M A, *Mammalian Retroelements. Genome Res.* 12(10): 1455-65 (2002), doi:10.1101/gr.282402).

RE-Based DNA Quantitation

RE-based quantitation methods are advantageous when compared to current, commercially available systems due to the presence of a large number of fixed insertions. With a high copy number of subfamily-specific RE repeats within the human genome, these human-specific DNA assays have a very sensitive dynamic range of 1 pg to 100 ng (Nicklas, J A; Buel, E., *Development of an Alu-based, Real-Time PCR Method for Quantitation of Human DNA in Forensic Samples*, J. Forensic Sci. 48(5): 1-9 (2003)). For example, the ALU Yb lineage contains approximately 1800 copies per genome and SVA contains approximately 1700 full length element copies per genome (Wang, H., referenced supra; Carter, A B, et al., *Genome-wide analysis of the human Alu Yb-lineage*, Hum. Genomics 1(3): 167-178 (2004)). This large copy number minimizes the effect of variation between individuals, resulting in highly reproducible quantitation values.

U.S. Patent Publication 2014/0051075 A1, to Sudhir K. Sinha, is entitled "Development of a Highly Sensitive Quantification System for Assessing DNA Degradation and Quality in Forensic Samples" and describes the detection of DNA quality with a multiplex reaction using ALU and SVA for human DNA quantification. Though very useful for forensic purposes, the described method does not detail specific application to cell free DNA from plasma and/or serum. The amplicon sizes needed for a cfDNA assay are different from those needed for forensic applications, and other details of the two methods such as amplification conditions and primer/probe concentrations differ as well.

There is a clear need in cancer management, and CRC treatment specifically, for a standardized and validated blood test to sensitively and robustly quantitate cfDNA integrity and concentration. The present application addresses this need by creating a multiplex qPCR assay for quantitating cfDNA integrity and concentration based on REs.

The most commonly employed method conducted by others in the field of cfDNA integrity and concentration assessment for cancer detection and monitoring is qPCR using the ALU 247/115 index. This method has shown promise in multiple studies; however, there is a strong need for a standardized, validated multiplex that can simultaneously and accurately measure cfDNA concentration, integrity and PCR inhibition from plasma and serum.

In one embodiment, the developed multiplex uses two independent retrotransposable element genomic targets, an ALU element in the Yb8 subfamily of 80 bp in size and an SVA element of 207 bp in size, in a multiplex based, real-time qPCR assay for the detection of two sized targets to assess the extent of DNA integrity. The multiplex exhibits high PCR efficiencies for both targets (see FIG. 1). The system also incorporates an internal positive control target synthetic sequence of 172 bp in size to monitor and enable the detection of PCR inhibitors in forensic samples. The system is highly sensitive due to its multi-copy nature, and the system is highly reproducible and accurate due to the high copy number (>1000 copies per genome) of the selected targets.

A pilot study with serum and plasma samples tested with the qPCR multiplex of 207 bp and 80 bp target sizes has been performed. Serum and plasma samples from normal healthy individuals were processed both with DNA purification and without purification (direct qPCR). The data shows several interesting observations. First, it is observed that the short target produces a quantification value as low as 0.3 picograms of cfDNA (Table 2). It should be noted that in this pilot study, the PCR was performed at 32 PCR cycles (a literature search reveals cfDNA qPCR assays are typically performed as low as 35 cycles). Even with 32 cycles, the ability of the RE-qPCR multiplex to detect cfDNA at very low levels is demonstrated. Cycle numbers and other PCR parameters may be further optimized.

Secondly, it is observed from this pilot study that the main challenge to overcome is the complete inhibition or lack of detection of the long target with serum and plasma samples processed using direct qPCR without DNA purification. This can be overcome in part by testing fragments of cfDNA of varying sizes and selecting the most sensitive and accurate targets. The use of robust enzymes and PCR additives may be of primary importance in overcoming the problem of lack of detection of the long target. This pilot study demonstrates that the basic concept in this effort of using the high copy number retrotransposon targets Yb8 and SVA in a multiplex qPCR system to detect DNA integrity for the application of colorectal cancer diagnosis and prognosis is feasible.

TABLE 2

RE qPCR on purified and direct qPCR serum and plasma samples from normal individuals.

| | ALU 80; Short (ng/μL) | SVA 207; Long (ng/μL) | DNA Integrity (SVA207/ ALU80) | IPC Ct (acceptable range from 18-22) |
|---|---|---|---|---|
| Whole serum 1 (direct) | 0.002 | 0 | 0 | Undetermined+ |
| Whole serum 2 (direct) | 0.022 | 0 | 0 | Undetermined+ |
| Whole serum 3 (direct) | 0.009 | 0 | 0 | Undetermined+ |
| Purified serum 1 | 0.020 | 0.009 | 0.45 | 20.2 |
| Purified serum 2 | 0.733 | 0.421 | 0.57 | 19.7 |
| Purified serum 3 | 0.045 | 0.013 | 0.29 | 20.2 |
| Whole plasma 4 (direct)* | 0.0003 | 0 | 0 | 24.9 |
| Whole plasma 5 (direct)* | 0.002 | 0 | 0 | 25.1 |
| Whole plasma 6 (direct)* | 0.0004 | 0 | 0 | 23.5 |
| Purified plasma 4 | 0.056 | 0.019 | 0.33 | 21.38 |
| Purified plasma 5 | 0.409 | 0.032 | 0.08 | 21.04 |
| Purified plasma 8 | 0.080 | 0.020 | 0.24 | 21.10 |

Breitbach 2014 method used for direct qPCR of plasma (The plasma was diluted in sterile water in a 1:40 ratio for direct qPCR measurement).
+Did not cross the cycle threshold at 32 PCR cycles.
Bold font indicates internal positive control Ct values outside of the acceptable range.

Figure 2B:
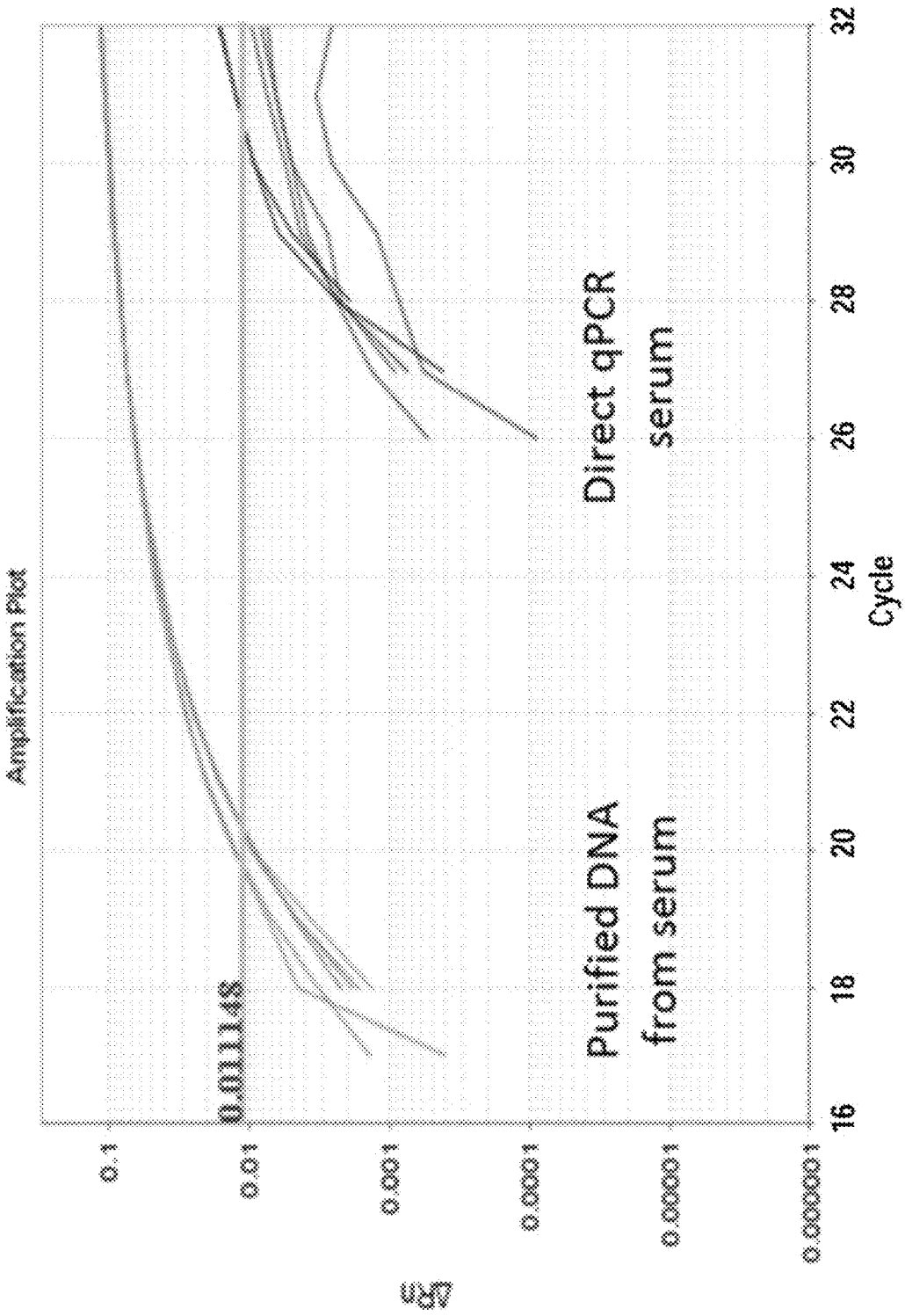
FIG. 2B shows qPCR amplification plots for serum samples, showing behavior both for purified DNA and for the case of using direct qPCR. The horizontal lines show the automatic cycle threshold setting.

Furthermore, the utility of the internal positive control (IPC) with direct qPCR serum and plasma samples is shown by the results of this pilot study. It is observed that with purified DNA from serum and plasma, no PCR inhibition is noted, as indicated by the acceptable IPC Ct values. On the other hand, the direct qPCR of both serum and plasma samples without DNA purification exhibits PCR inhibition as indicated by the failure of the IPC target to amplify as expected (see IPC amplification plots in FIG. 2 and IPC Ct values in Table 2). This work demonstrates the challenge in performing direct qPCR on serum and plasma samples.

EXAMPLES

Example 1

Experimental Design

The objective of this work was the development of a three target (one short RE target, one long RE target, and one internal positive control synthetic target) multiplex RE-qPCR assay to accurately and robustly obtain cfDNA concentration and DNA integrity values from normal and CRC patients directly from plasma/serum samples without DNA purification. The following process was used to address the goal of this work.

Step 1: Identification of Appropriate Multi Copy Targets (ALU, LINE, and/or SVA Element) for Accurate Quantitation of cfDNA Concentration.

Diagnostic potential of cfDNA integrity has been shown to be similar when different interspersed genetic elements are used (ALU and LINE1 in Madhavan, D, et al., *Plasma DNA integrity as a biomarker for primary and metastatic breast cancer and potential marker for early diagnosis*, Breast Cancer Res. Treat. 146(1): 163-74 (2014), doi: 10.1007/s10549-014-2946-2). Diagnostic potential is enhanced when multiple measures (e.g. concentration and integrity) are combined (Hao, T B, et al., *Circulating cell-free DNA in serum as a biomarker for diagnosis and prognostic prediction of colorectal cancer*, British Journal of Cancer 2014: 1-8, doi 10.1038/bjc.2014.470; Madhavan, et al., referenced supra). These results highlight the utility of evaluating different RE-based DNA quantitation methods for determining cfDNA concentration and integrity. In the case of the commonly employed ALU 247/115 protocol, targeted sequences of a single ALU element are used, and thus the two fragments analyzed are not independent. This can lead to less than accurate quantification values. As explained more fully above, the target sequences of the ALU 247/115 protocol cannot be multiplexed, and single-plexing is a much less advantageous experimental arrangement for the present purpose. The system of the present invention is one in which independent targets are used to accurately quantitate concentration and integrity within a single qPCR reaction.

For this application, a qPCR system employing two different sized targets has been assessed with blood serum and plasma samples. Additional targets may be assessed with the purpose of selecting the most accurate targets. Assessment included evaluating the ability of each tested target to accurately quantify DNA as compared to the known quantitation standard NIST SRM 2372 (Human DNA Quantitation Standard). The individual short RE target and long RE target that most accurately quantifies cfDNA and cfDNA integrity in the normal and CRC patient groups will be incorporated into the three-target multiplex. This step enables the identification of optimal targets for the accurate detection of cfDNA and cfDNA integrity.

Step 2: Creation of a Robust Three Target Multiplex Assay to Accurately Quantitate cfDNA Concentration and Integrity.

The two targets identified which most accurately quantify cfDNA concentration and integrity in the normal and CRC patient groups in a single-amplification multiplex reaction are used. The third target is a synthetic internal positive control (IPC) to monitor presence of inhibitors in the sample that can affect the accuracy of cfDNA measurement by qPCR. The approach to achieve the subject goal requires strategic planning as well as multiple attempts to optimize the reaction conditions. The task increases in complexity as one tries to multiplex more primers. There are several published reports that provide guidance to achieve successful PCR multiplexing (Markoulatos, P; Siafakas, N; Moncany, M, *Multiplex polymerase chain reaction: a practical approach*, J. Clin. Lab. Anal. 16(1): 47-51 (2002); Schoske, R; Vallone, P M; Ruitberg, C M; Butler, J M, *Multiplex PCR design strategy used for the simultaneous amplification of 10 Y chromosome short tandem repeat (STR) loci*, Anal. Bioanal. Chem. 375(3): 333-343 (2003); Henegariu, O; Heerema, N A; Dlouhy, S R; Vance, G H; Vogt, P H, *Multiplex PCR: critical parameters and step-by-step protocol*, Biotechniques 23(3): 504-511 (1997); Shuber, A P; Grondin, V J; Klinger, K W, *A simplified procedure for developing multiplex PCRs*, Genome Res. 5(5): 488-493 (1995), doi:10.1101/gr.5.5.488). The parameters to consider for developing a multiplexed PCR system are: 1) Primer length and sequence;

2) Melting temperature of each primer; 3) Relative concentration of primers; 4) Concentration of PCR buffer; 5) Balance between magnesium chloride and dNTP concentration; 6) Cycling Temperatures; 7) Cycling Times; and 8) Taqman probe design. We have analyzed performance of the multiplex assay in the following ways: melt curve analyses to show sequence specificity of the primer sequences; quantitation of the NIST SRM 2372 human DNA quantitation standard to determine accuracy; and quantitation of a dilution series of the NIST standard to assess sensitivity. This step enables the development of an accurate, sensitive, reproducible, and robust multiplex qPCR assay to determine cfDNA concentration and integrity in a single reaction in less than 2 hours.

Step 3: Determine if and how PCR Inhibition Affects Accuracy of RE-qPCR from Human Blood Plasma and Serum.

Serum and plasma specimens are known to frequently contain PCR inhibitors, including hematin, Immunoglobulin G, and low molecular mass solutes and proteins (Al-Soud, W A; Jönsson, L J; Rådström, P, *Identification and Characterization of Immunoglobulin G in Blood as a Major Inhibitor of Diagnostic PCR*, J. Clin. Microbiol. 38(1): 345-350 (2000)). These substances can significantly reduce PCR efficiency and cause false negative results. An important contribution of the present multiplex assay is the introduction of a synthetic DNA sequence used as an internal positive control (IPC) within each RE-qPCR reaction. This control evaluates PCR inhibition and determines successful PCR within a sample. Previous work has demonstrated that such a control increases reliability of PCR data by successfully identifying the effect of PCR inhibitors in a specimen (Pineda, G M; Montgomery, A H; Thompson, R; Indest, B; Carroll, M; Sinha, S K, *Development and validation of InnoQuant™, a sensitive human DNA quantitation and degradation assessment method for forensic samples using high copy number mobile elements Alu and SVA*, Forensic Sci. Int. Genet. 13: 224-235 (2014), doi:10.1016/j.fsigen.2014.08.007). Several studies show that the distribution of cfDNA concentration and integrity values from CRC patients and control subjects differ significantly, but the distributions of values are overlapping. It is possible that addressing inhibition may add resolution to these distributions. Incorporation of an IPC in the multiplex allows verification that the PCR reaction took place as expected without inhibitor or other adverse effects. IPC data has been analyzed from both purified DNA and direct RE-qPCR experiments to determine the extent of inhibition with respect to an empirically derived $C_T$ threshold. This step enables utilization of the developed multiplex in a direct qPCR reaction that includes verification of PCR success, while reducing false negative results.

Example 2

Protocol for Serum and Plasma Separation

Serum and plasma separation are performed according to the standard protocol and within four hours of collection, and stored at −80° C. until they are processed. Care is taken to avoid freeze-thaw cycles. For serum specimens, whole blood is collected in the commercially available red-topped test tube Vacutainer (Becton Dickinson). For plasma specimens, whole blood is collected in the commercially available anticoagulant-treated tubes e.g., EDTA-treated (lavender tops) or citrate-treated (light blue tops).

Example 3

Protocol for Direct DNA Quantitation

Two separate protocols have previously been described for direct DNA quantification from either human serum (Umetani, N., et al., *Increased integrity of free circulating DNA in sera of patients with colorectal or periampullary cancer: Direct quantitative PCR for ALU repeats*, Clin. Chem. 52(6): 1062-1069 (2006), doi:10.1373/clinchem.2006.068577) or plasma (Breitbach, S, et al., *Direct quantification of cell-free, circulating DNA from unpurified plasma*, PLOS One 9(3): e87838 (2014), doi: 10.1371/journal.pone.0087838). We have tested both of these methods on serum and plasma in order to compare amplification efficiency from both methods. The first method includes deactivation or elimination of proteins that bind to template DNA or DNA polymerase and might invalidate qPCR results. A volume of 20 μL of each serum or plasma sample is mixed with 20 μL of a preparation buffer that contains 25 mL/L Tween 20, 50 mM Tris, and 1 mM EDTA. This mixture is then digested with 16 μg of proteinase K solution (Qiagen) at 50° C. for 20 min, followed by 5 min of heat deactivation and insolubilization at 95° C. After subsequent centrifugation at 10,000 g for 5 min, 0.2 μL of the supernatant (containing 0.1-μL equivalent volume of serum/plasma) is used as a template for each direct RE-qPCR reaction. The second method bypasses the protein removal step and only requires 1:40 dilution of the serum/plasma sample with sterile $H_2O$.

Example 4

Procedure for DNA Purification

For comparison to and validation of direct quantification of cfDNA, RE-qPCR has been performed on isolated, purified cfDNA. cfDNA may be purified by magnetic bead extraction or by using the silica based membrane QIAamp DNA Investigator Kit (Qiagen).

Example 5

Design of Primers and TaqMan Probes

Primers and labeled probes used in the qPCR reactions may be obtained from Eurofins MWG/Operon, Integrated DNA Technologies, or a variety of other vendors. Primers for amplifying the ALU 115 and ALU 247 fragments and LINE1 79 and 300 fragments have been reported previously (Umetani N, et al., *Increased integrity of free circulating DNA in sera of patients with colorectal or periampullary cancer: Direct quantitative PCR for ALU repeats*, Clin. Chem. 52(6): 1062-1069 (2006), doi:10.1373/clinchem.2006.068577; Mead, R; Duku, M; Bhandari, P; Cree I A, *Circulating tumor markers can define patients with normal colons, benign polyps, and cancers*, Br. J. Cancer 105(2): 239-245 (2011), doi: 10.1038/bjc.2011.230).

Figure 3:
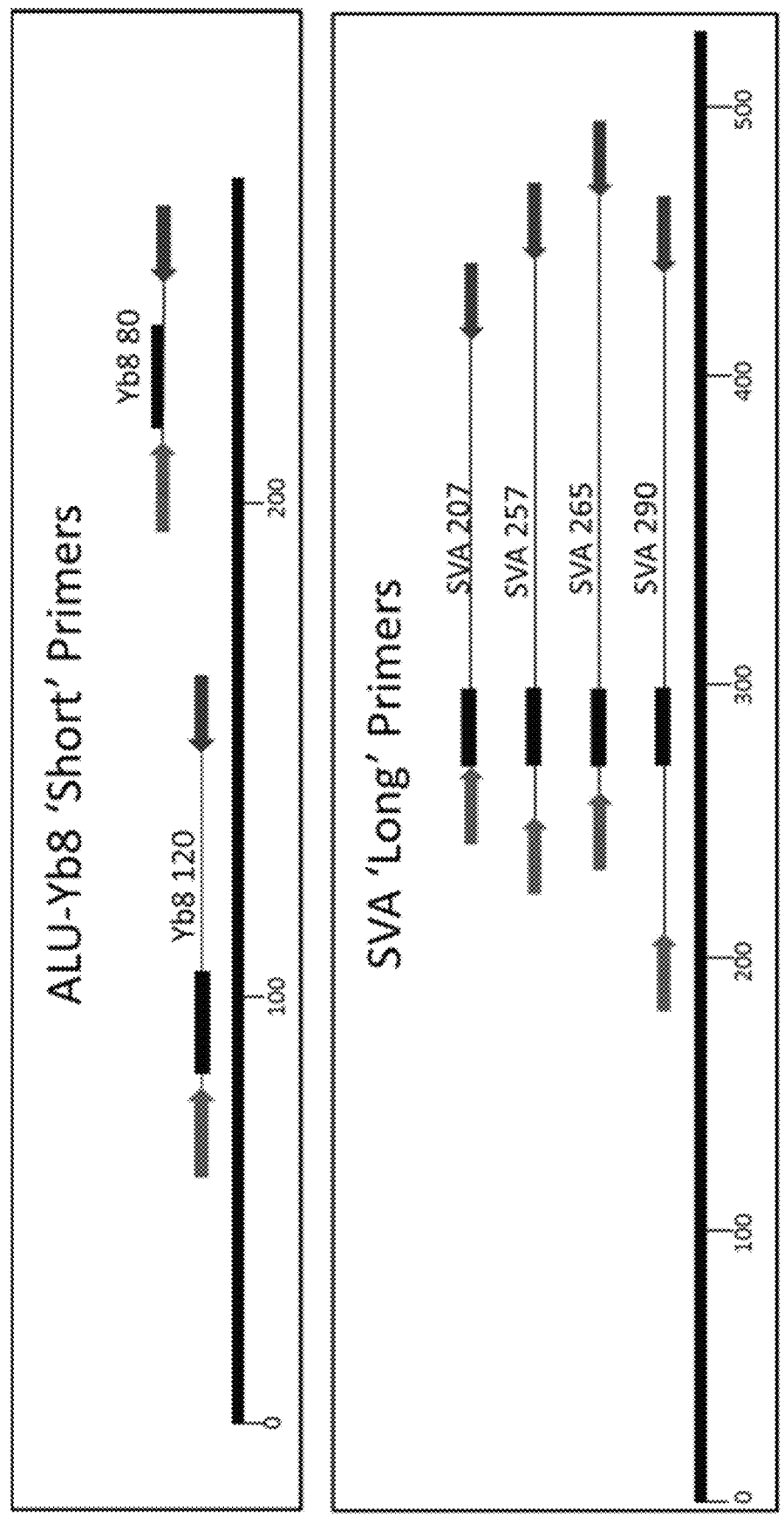
FIG. 3 shows a schematic representation of relative positions of the forward and reverse primers as well as the double labeled probes for qPCR analysis. The two short targets designed within the Yb8 sequence are 80 and 120 bp in size. The four long targets designed within the SVA sequence are 207, 257, 265, and 290 bp in size.
Figure 4A:
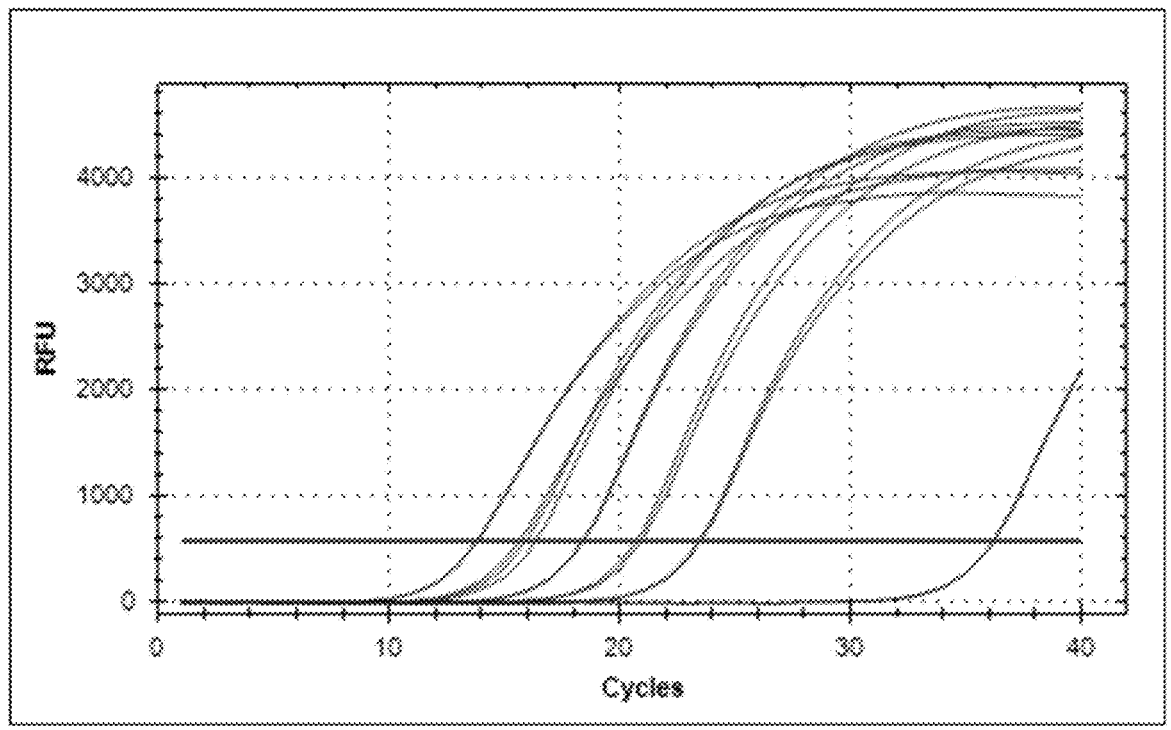
FIG. 4A shows an amplification plot for the SYBR qPCR analysis of the Yb8-119 target using standard DNA (1 ng, 200 pg, 40 pg, 8 pg, and 1.6 pg) in green, with positive control in red and no template control in black.
Figure 4B:
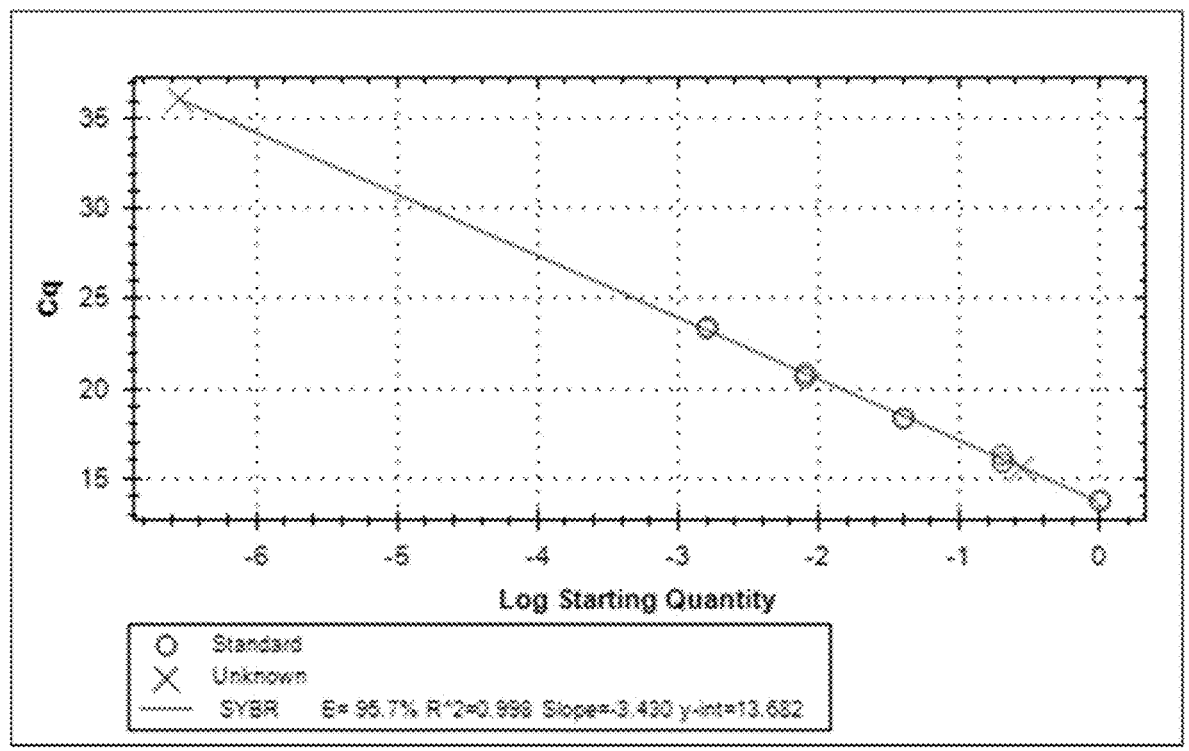
FIG. 4B shows a standard curve for the SYBR qPCR analysis of the Yb8-119 target using standard DNA (1 ng, 200 pg, 40 pg, 8 pg, and 1.6 pg).
Figure 4C:
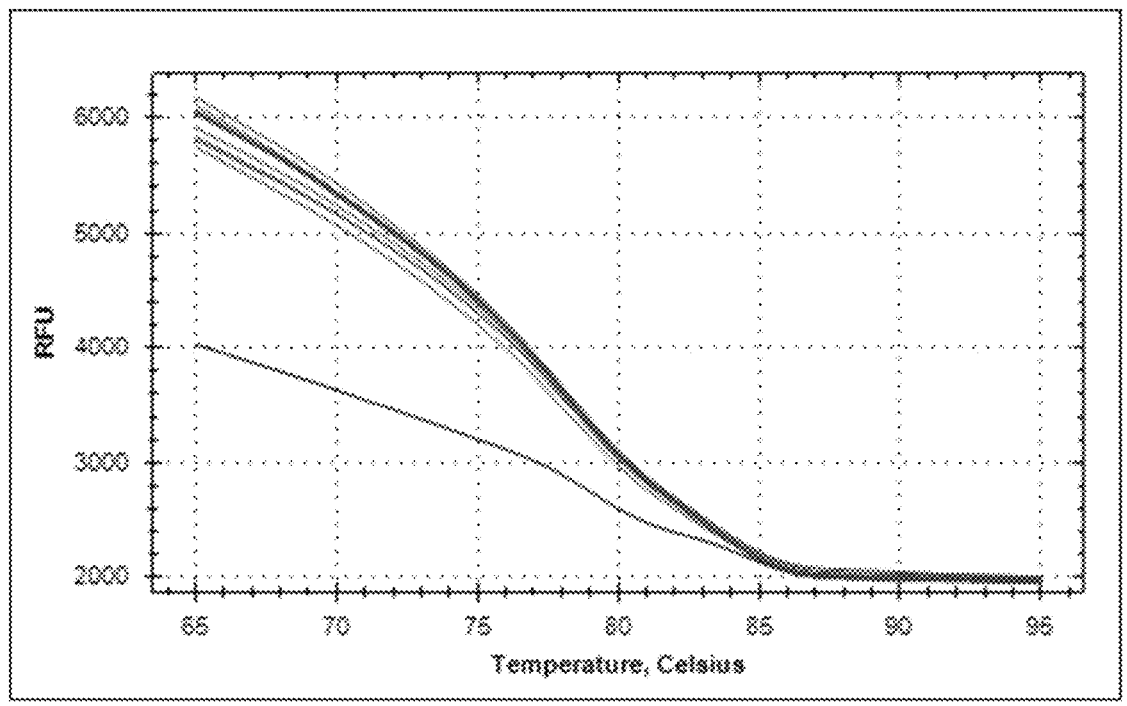
FIG. 4C shows a melt curve for the SYBR qPCR analysis of the Yb8-119 target using standard DNA (1 ng, 200 pg, 40 pg, 8 pg, and 1.6 pg) in green, with positive control in red and no template control in black.
Figure 4D:
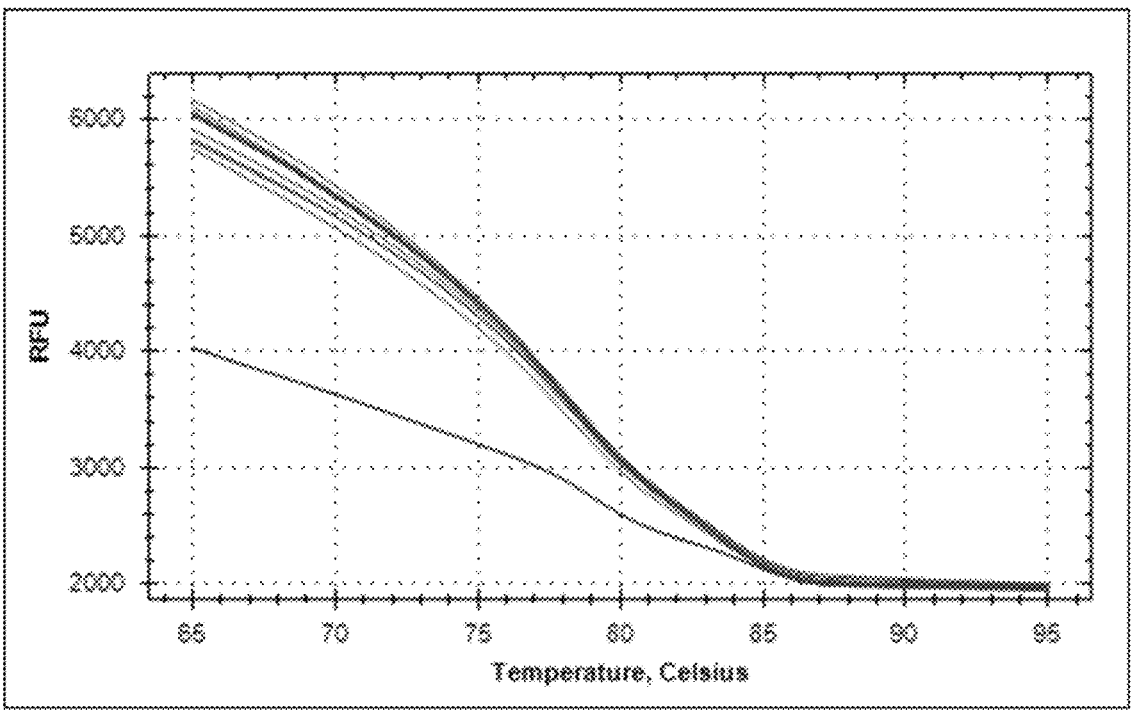
FIG. 4D shows a melt peak plot for the SYBR qPCR analysis of the Yb8-119 target using standard DNA (1 ng, 200 pg, 40 pg, 8 pg, and 1.6 pg) in green, with positive control in red and no template control in black.
Figure 5A:
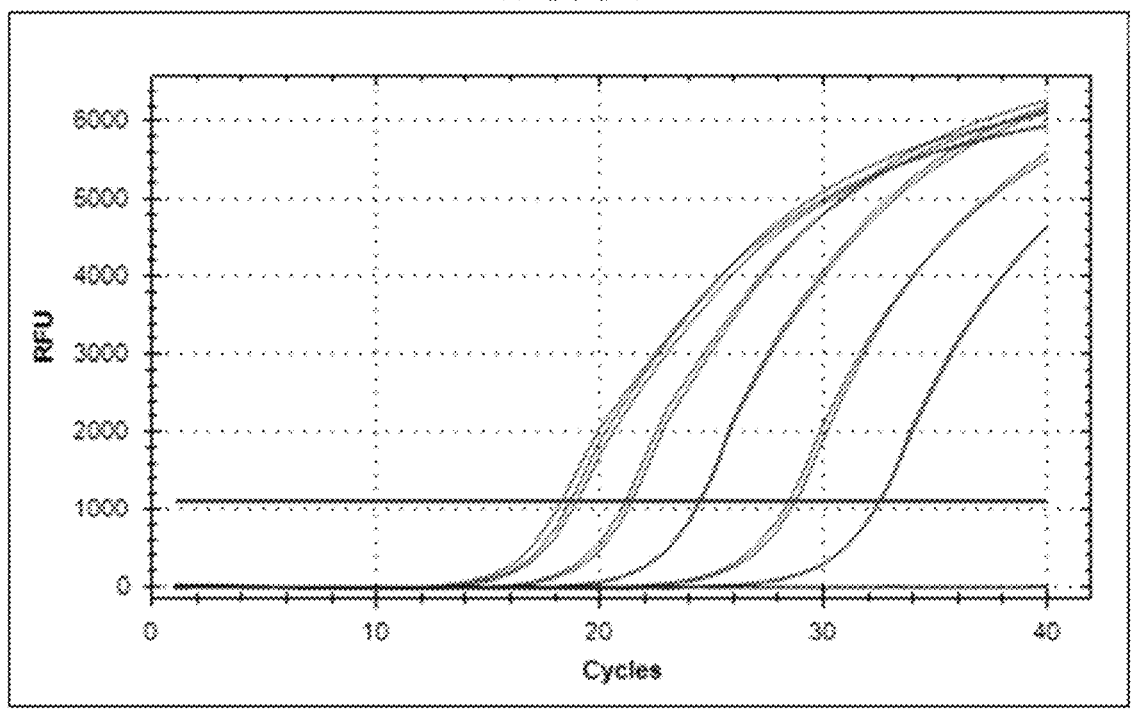
FIG. 5A shows an amplification plot for the SYBR qPCR analysis of the SVA-399 target using standard DNA (1 ng, 200 pg, 40 pg, 8 pg, and 1.6 pg) in green, with positive control in red and no template control in black.
Figure 5B:
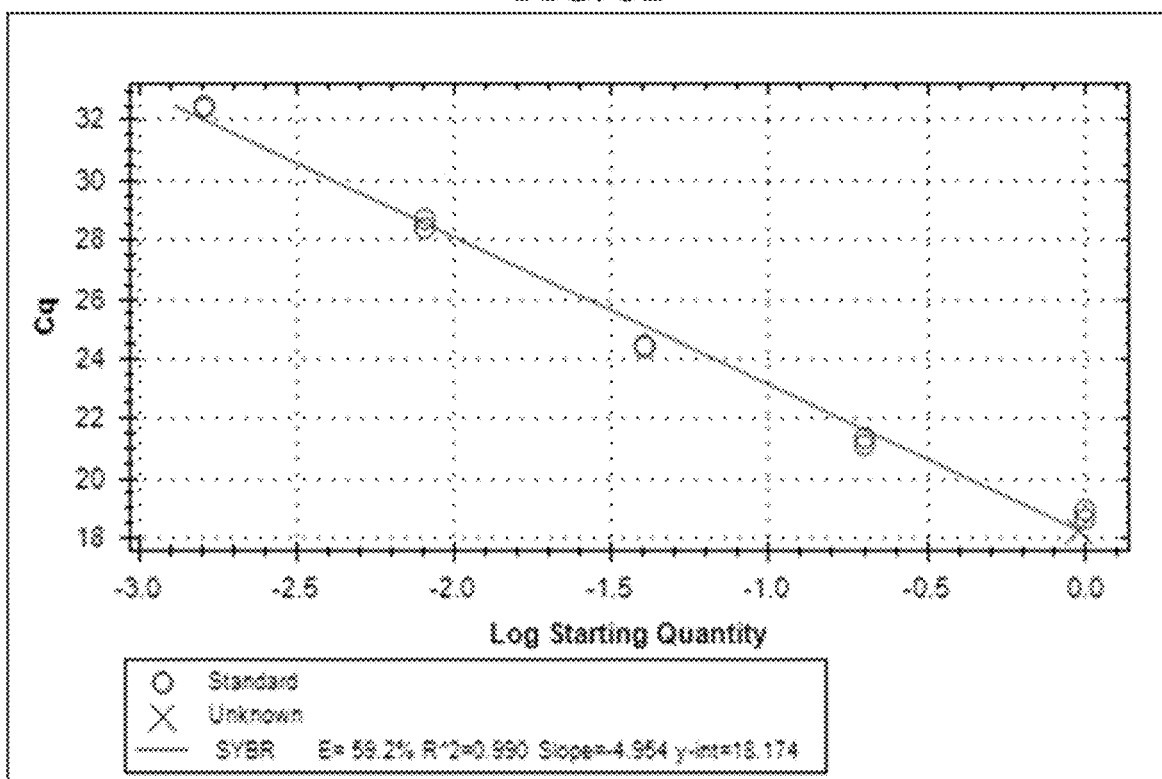
FIG. 5B shows a standard curve for the SYBR qPCR analysis of the SVA-399 target using standard DNA (1 ng, 200 pg, 40 pg, 8 pg, and 1.6 pg).
Figure 5C:
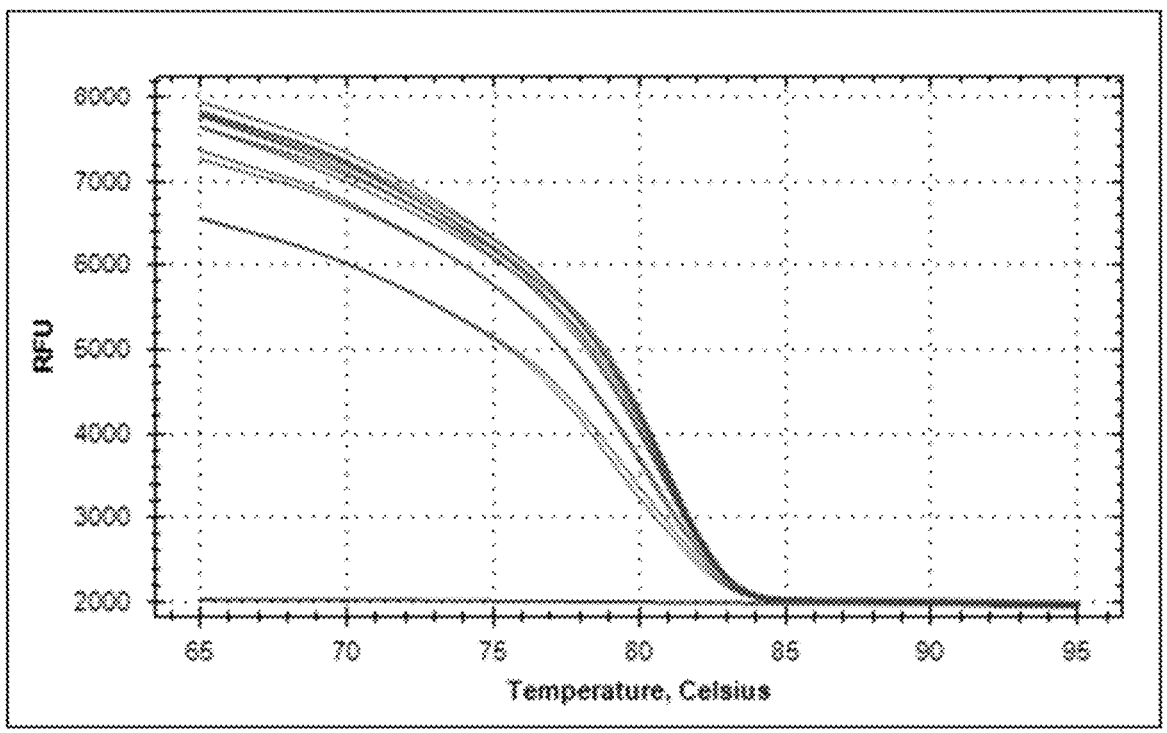
FIG. 5C shows a melt curve for the SYBR qPCR analysis of the SVA-399 target using standard DNA (1 ng, 200 pg, 40 pg, 8 pg, and 1.6 pg) in green, with positive control in red and no template control in black.
Figure 5D:
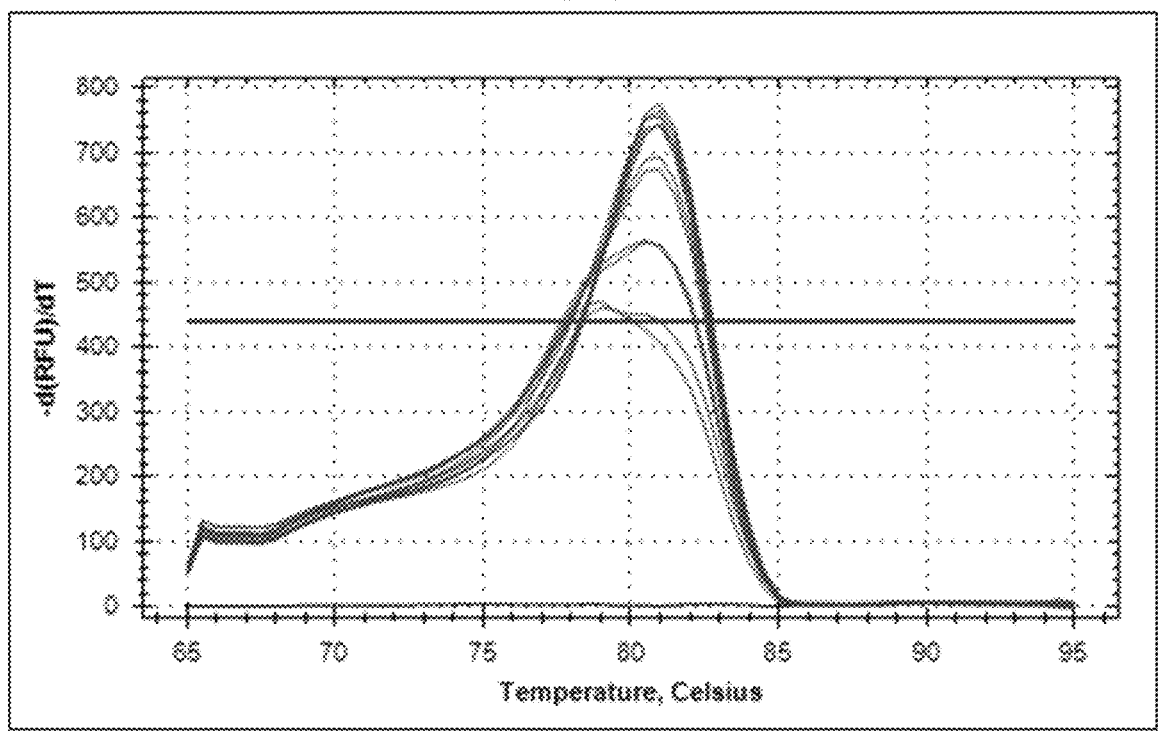
FIG. 5D shows a melt peak plot for the SYBR qPCR analysis of the SVA-399 target using standard DNA (1 ng, 200 pg, 40 pg, 8 pg, and 1.6 pg) in green, with positive control in red and no template control in black.
Figure 6A:
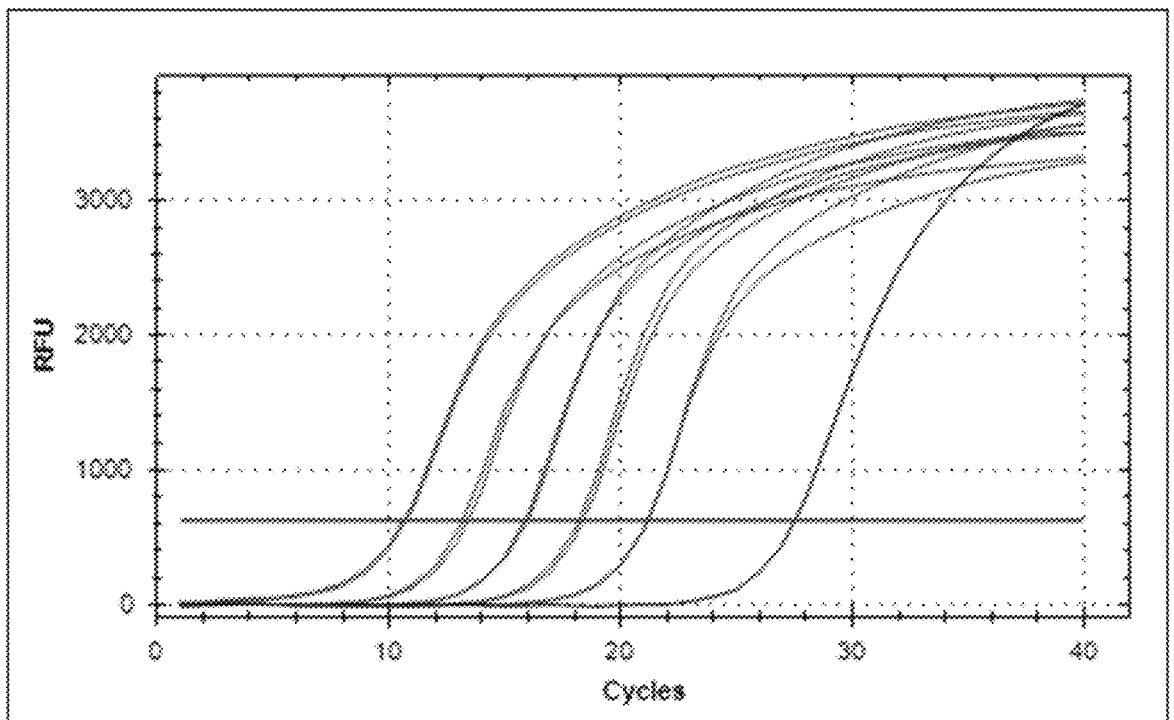
FIG. 6A shows an amplification plot for the SYBR qPCR analysis of the Alu-115 target using standard DNA (5 ng, 1 ng, 200) pg, 40 pg, and 8 pg) in green, with positive control in red and no template control in black.
Figure 6B:
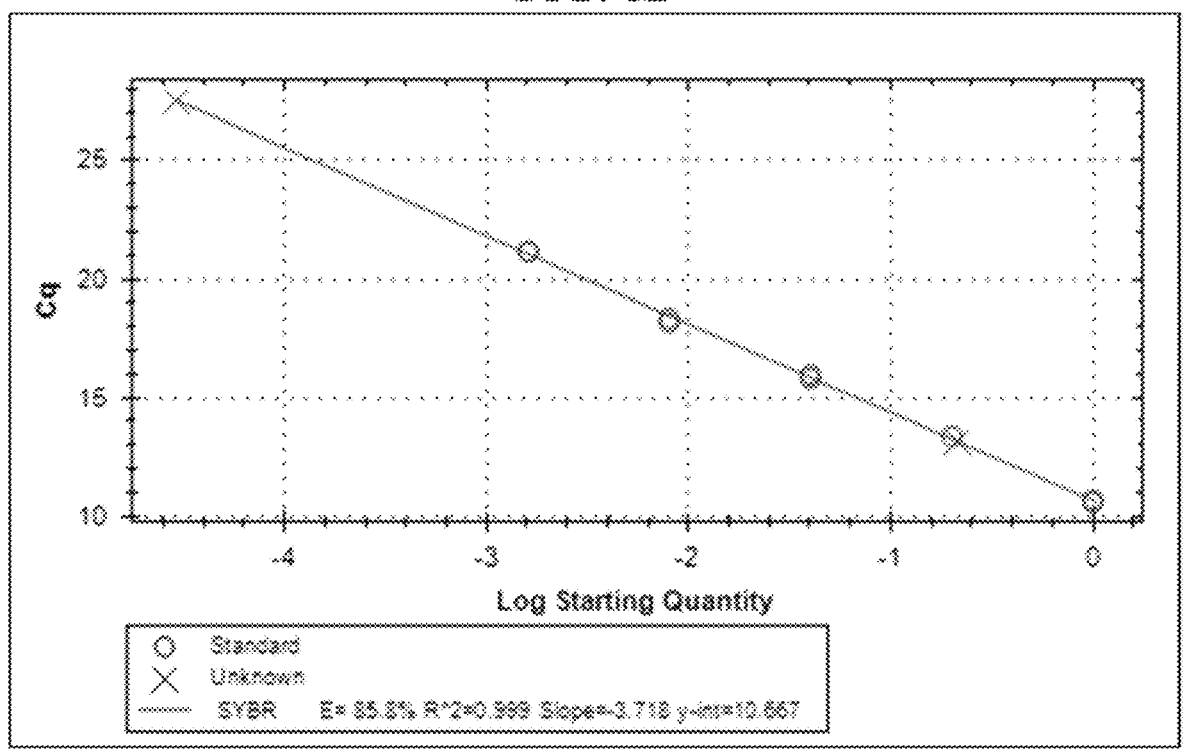
FIG. 6B shows a standard curve for the SYBR qPCR analysis of the Alu-115 target using standard DNA (5 ng, 1 ng, 200 pg, 40 pg, and 8 pg).
Figure 6C:
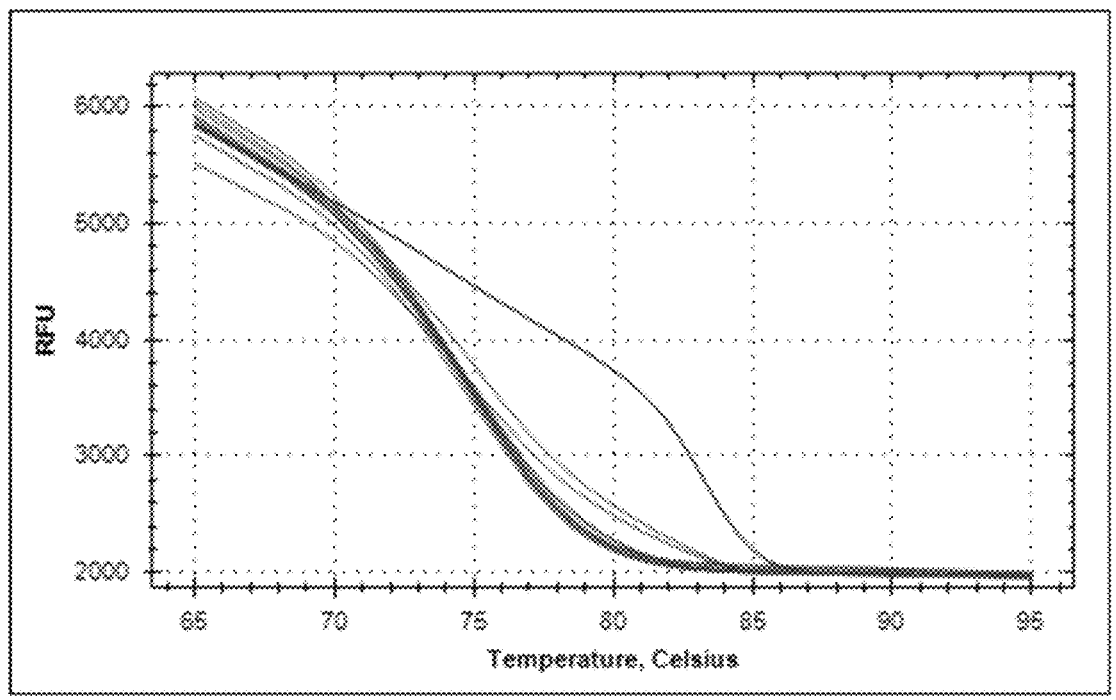
FIG. 6C shows a melt curve for the SYBR qPCR analysis of the Alu-115 target using standard DNA (5 ng, 1 ng, 200 pg, 40 pg, and 8 pg) in green, with positive control in red and no template control in black.
Figure 6D:
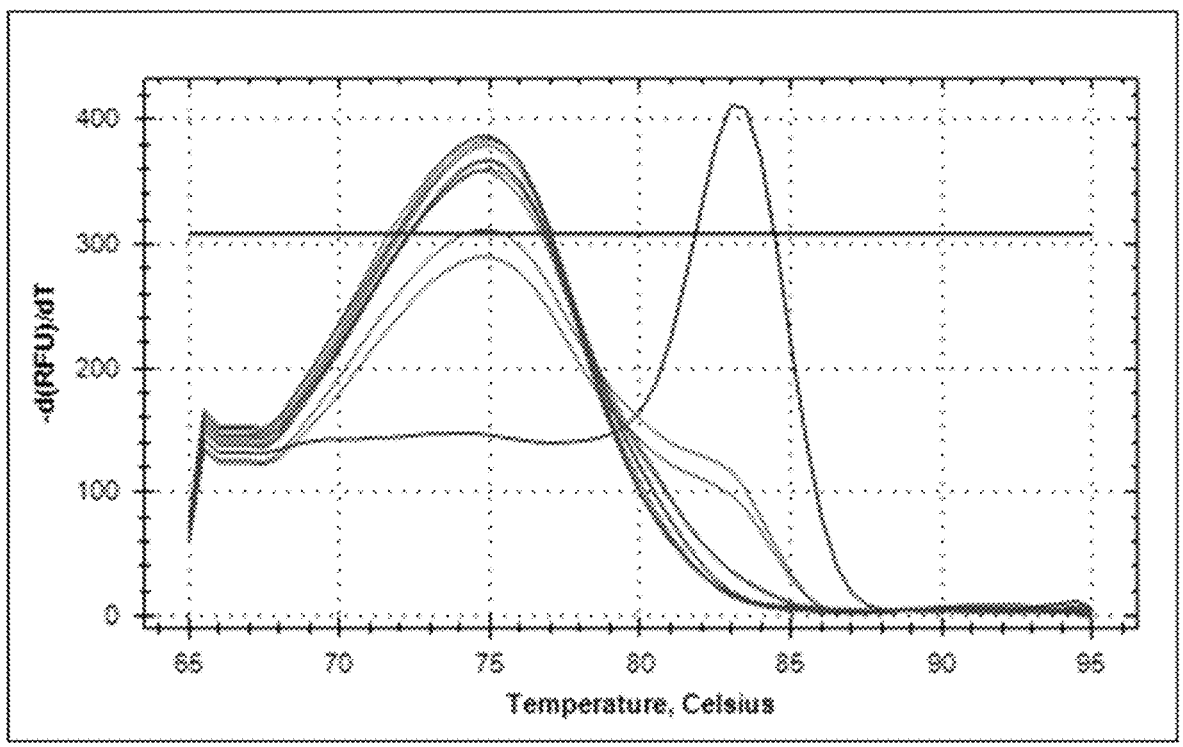
FIG. 6D shows a melt peak plot for the SYBR qPCR analysis of the Alu-115 target using standard DNA (5 ng, 1 ng, 200 pg, 40 pg, and 8 pg) in green, with positive control in red and no template control in black.
Figure 7A:
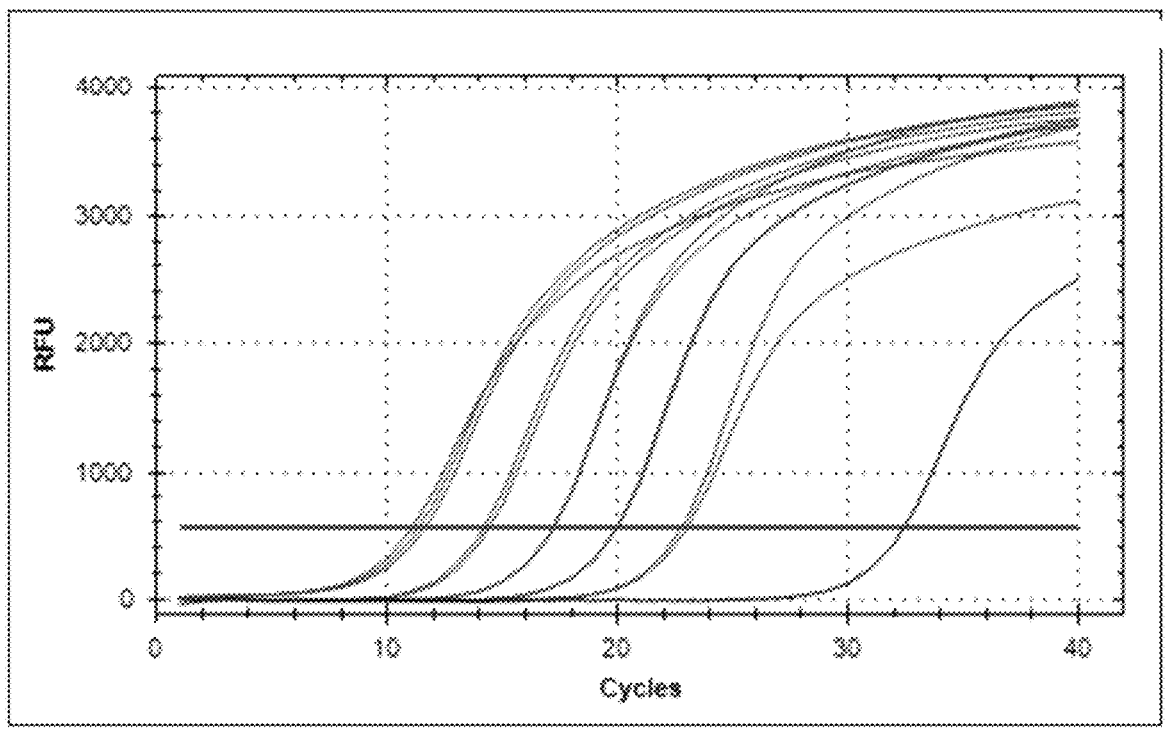
FIG. 7A shows an amplification plot for the SYBR qPCR analysis of the Alu-247 target using standard DNA (5 ng, 1 ng, 200 pg, 40 pg, and 8 pg) in green, with positive control in red and no template control in black.
Figure 7B:
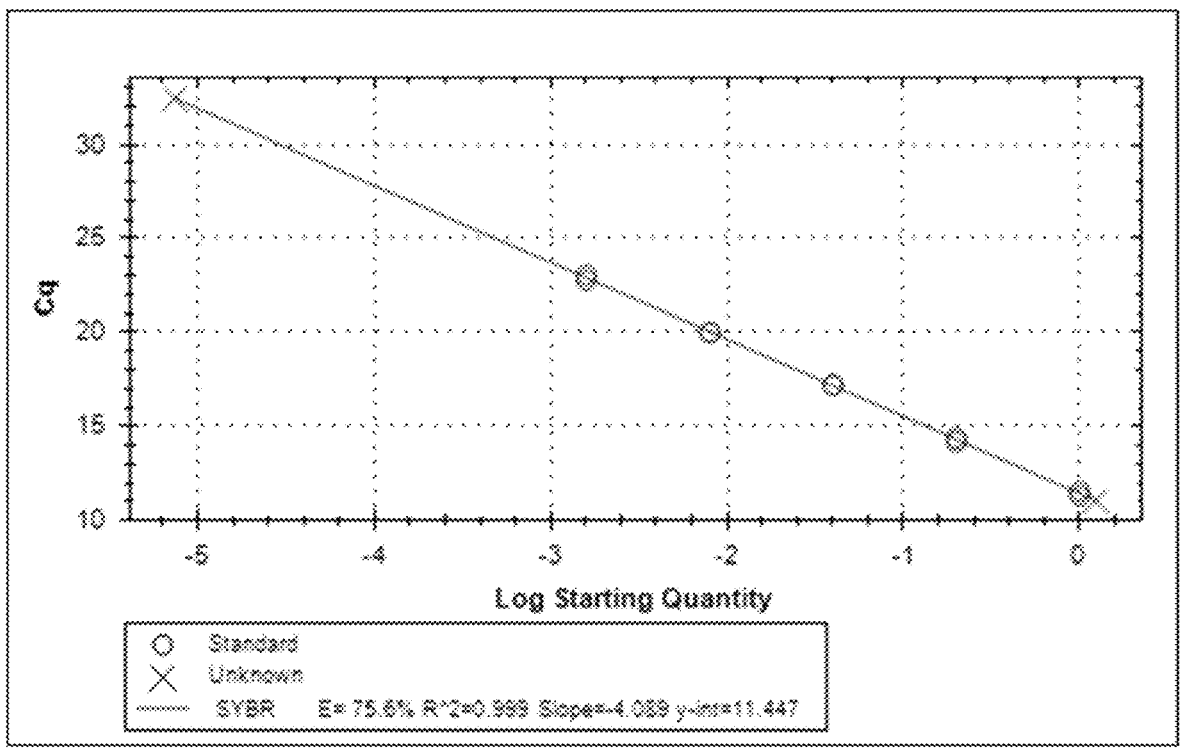
FIG. 7B shows a standard curve for the SYBR qPCR analysis of the Alu-247 target using standard DNA (5 ng, 1 ng, 200 pg, 40 pg, and 8 pg).
Figure 7C:
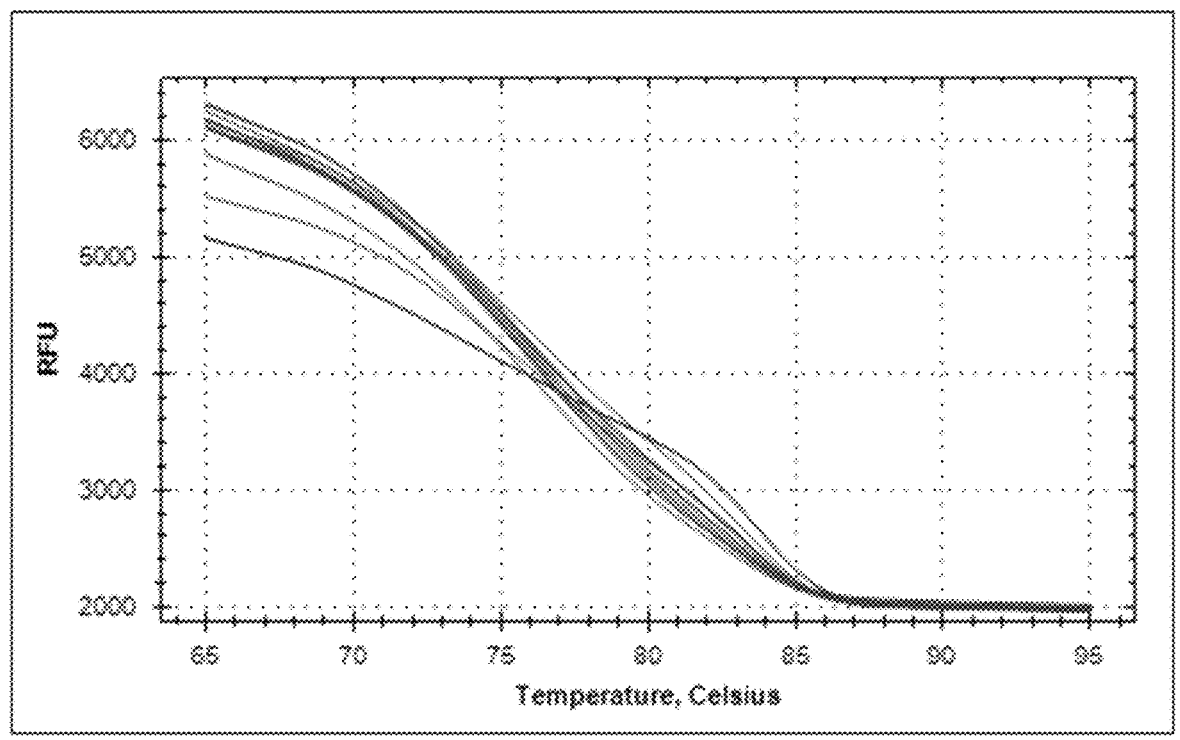
FIG. 7C shows a melt curve for the SYBR qPCR analysis of the Alu-247 target using standard DNA (5 ng, 1 ng, 200 pg, 40 pg, and 8 pg) in green, with positive control in red and no template control in black.
Figure 7D:
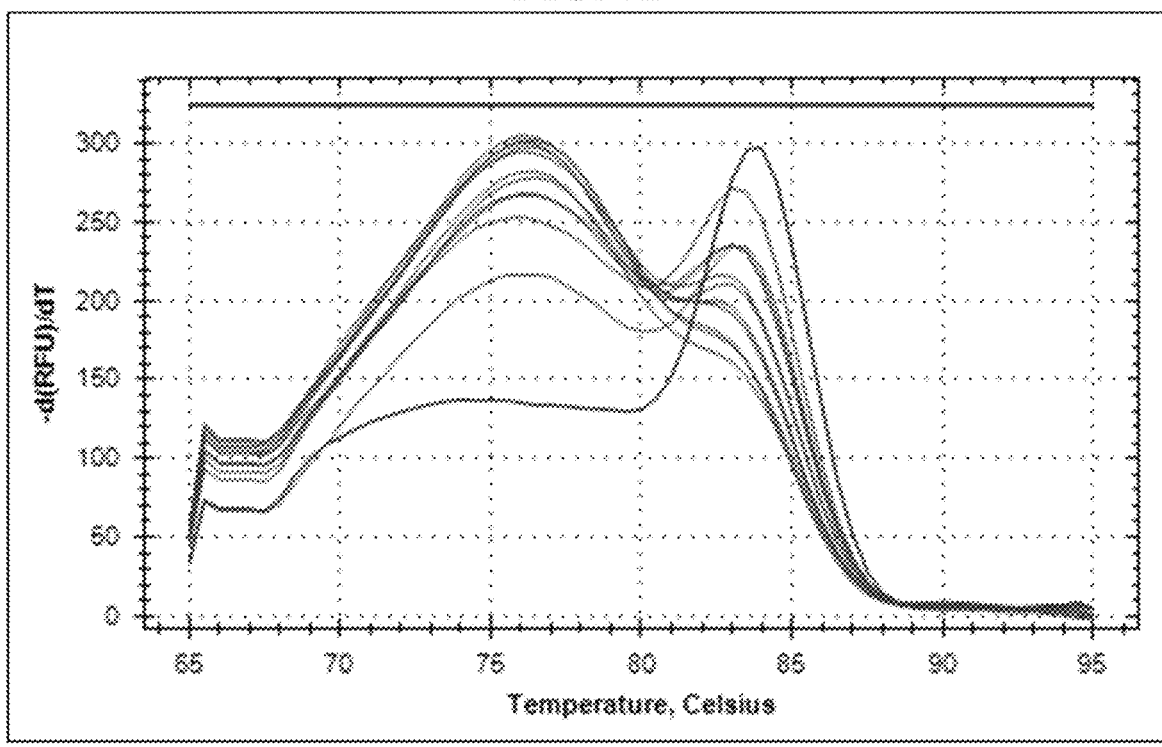
FIG. 7D shows a melt peak plot for the SYBR qPCR analysis of the Alu-247 target using standard DNA (5 ng, 1 ng, 200 pg, 40 pg, and 8 pg) in green, with positive control in red and no template control in black.
Figure 8A:
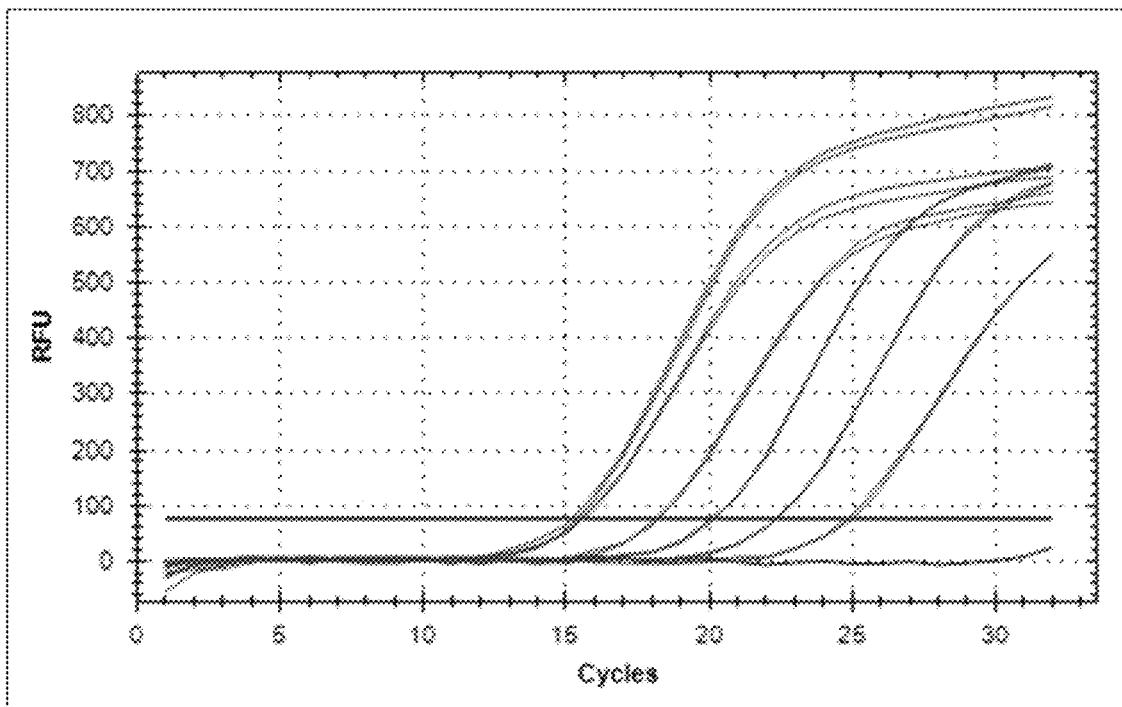
FIG. 8A shows an amplification plot for the Yb8-80 target of a real-time PCR multiplex of the Yb8-80 and SVA-207 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.
Figure 8B:
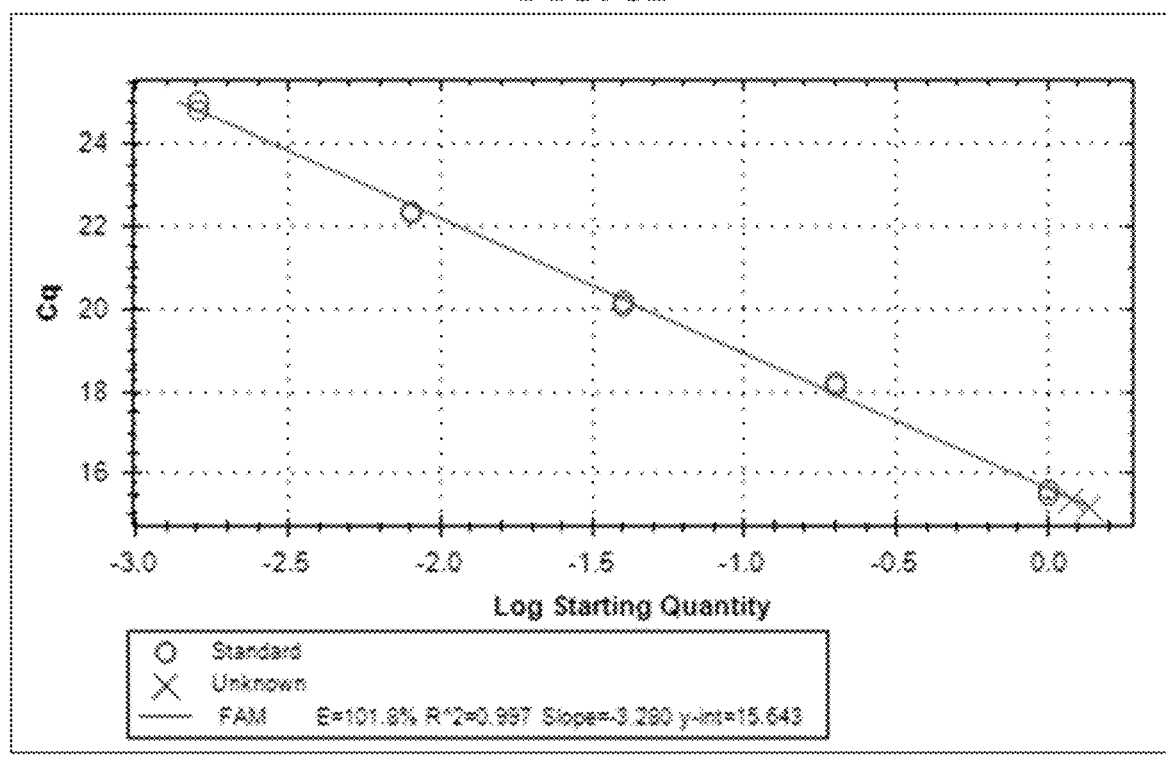
FIG. 8B shows a standard curve for the Yb8-80 target of a real-time PCR multiplex of the Yb8-80 and SVA-207 targets.
Figure 8C:
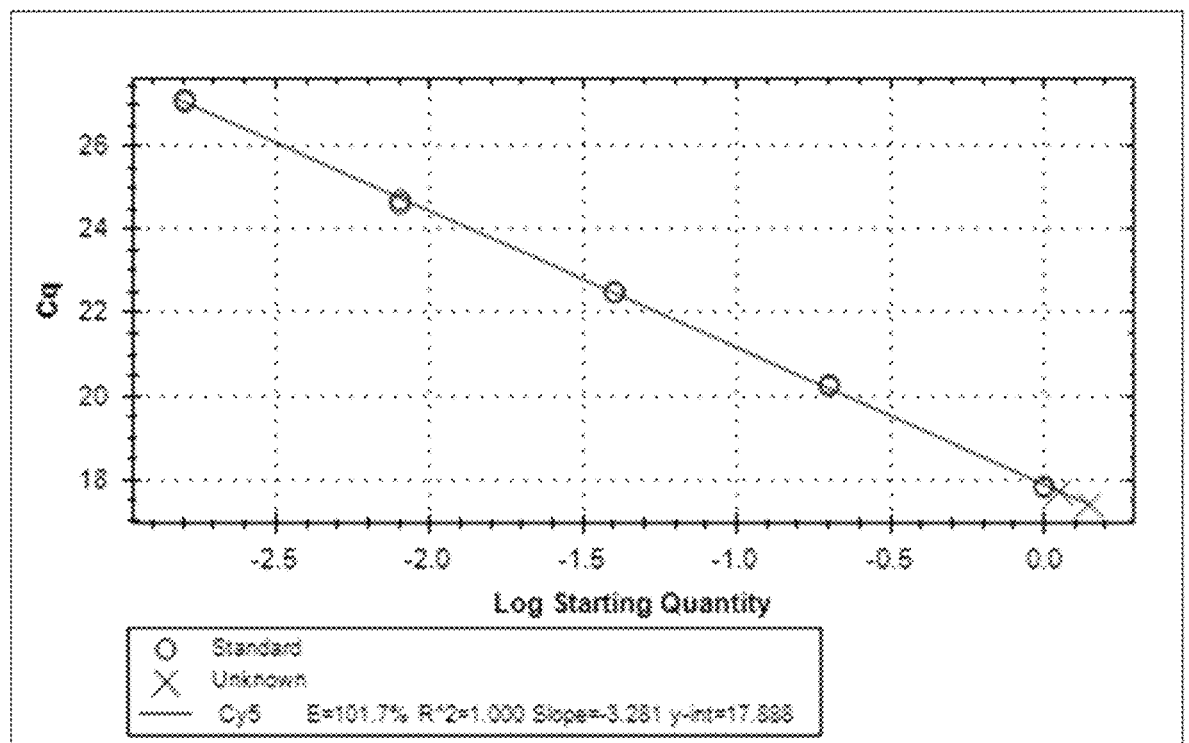
FIG. 8C shows an amplification plot for the SVA-207 target of a real-time PCR multiplex of the Yb8-80 and SVA-207 targets, the quantification of DNA in each sample being determined by use of a calibration curve with serial dilutions (1 ng, 200 pg, 40 pg, 8 pg, and 1.6 pg), with amplification of the SVA-207 target in purple, positive control in red and no template control in black.
Figure 8D:
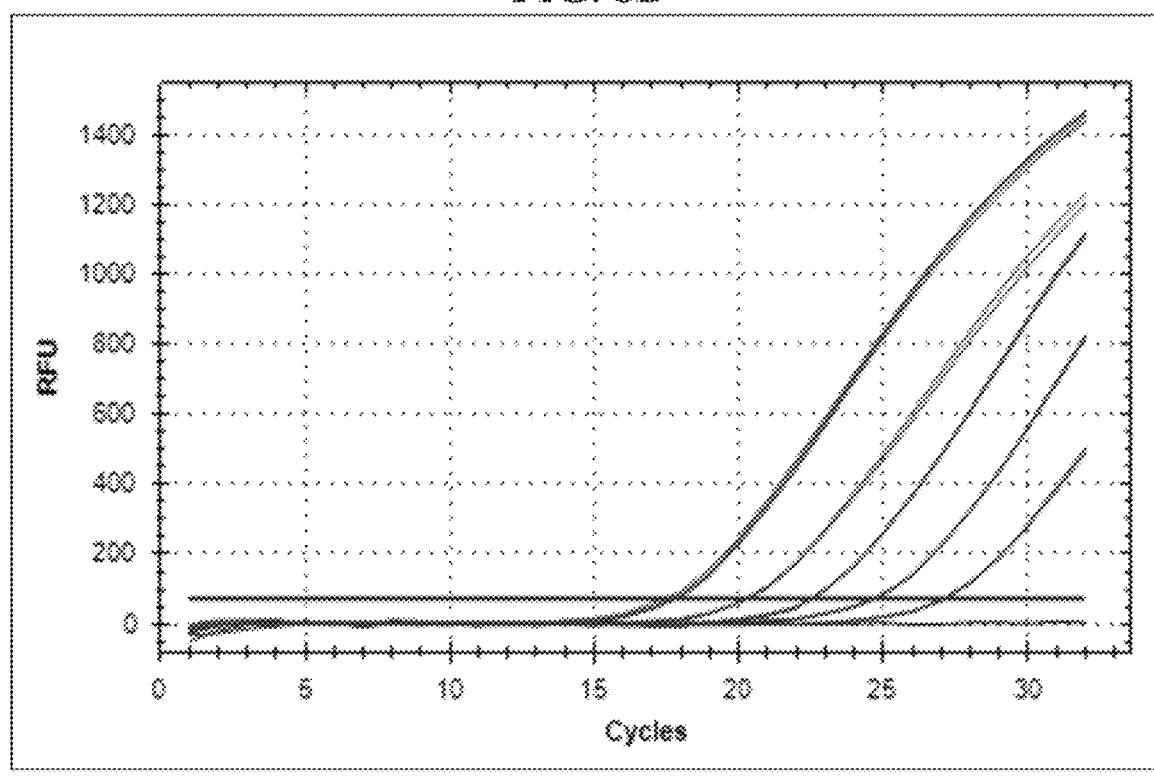
FIG. 8D shows a standard curve for the SVA-207 target of a real-time PCR multiplex of the Yb8-80 and SVA-207 targets.
Figure 8E:
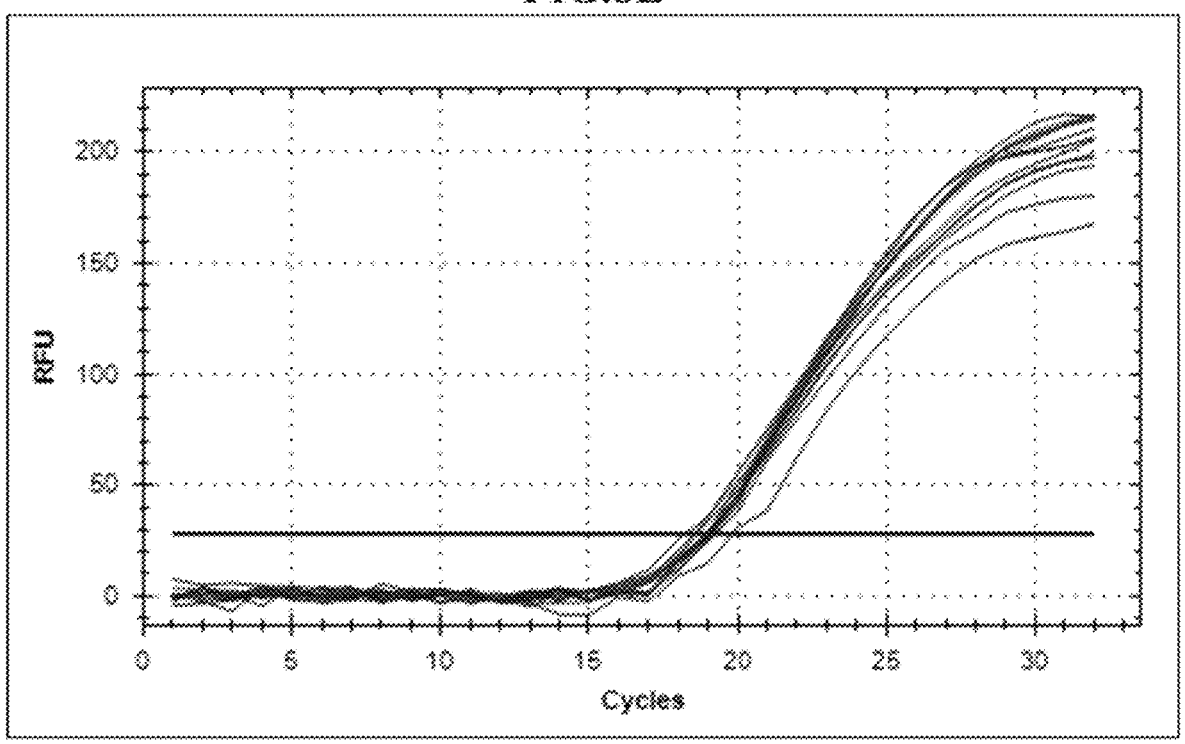
FIG. 8E shows an amplification plot of the internal positive control target within a real-time PCR multiplex of the Yb8-80 and SVA-207 targets, with amplification of the internal positive control target in blue.
Figure 9A:
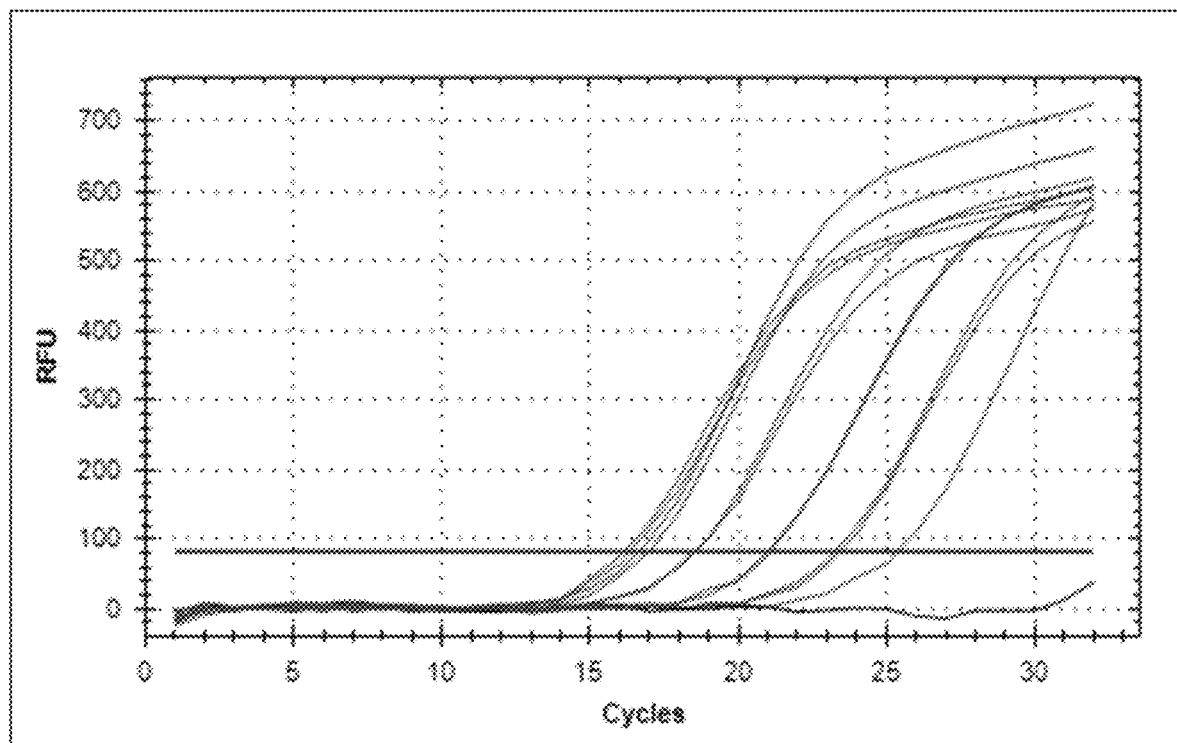
FIG. 9A shows an amplification plot for the Yb8-80 target of a real-time PCR multiplex of the Yb8-80 and SVA-257 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.
Figure 9B:
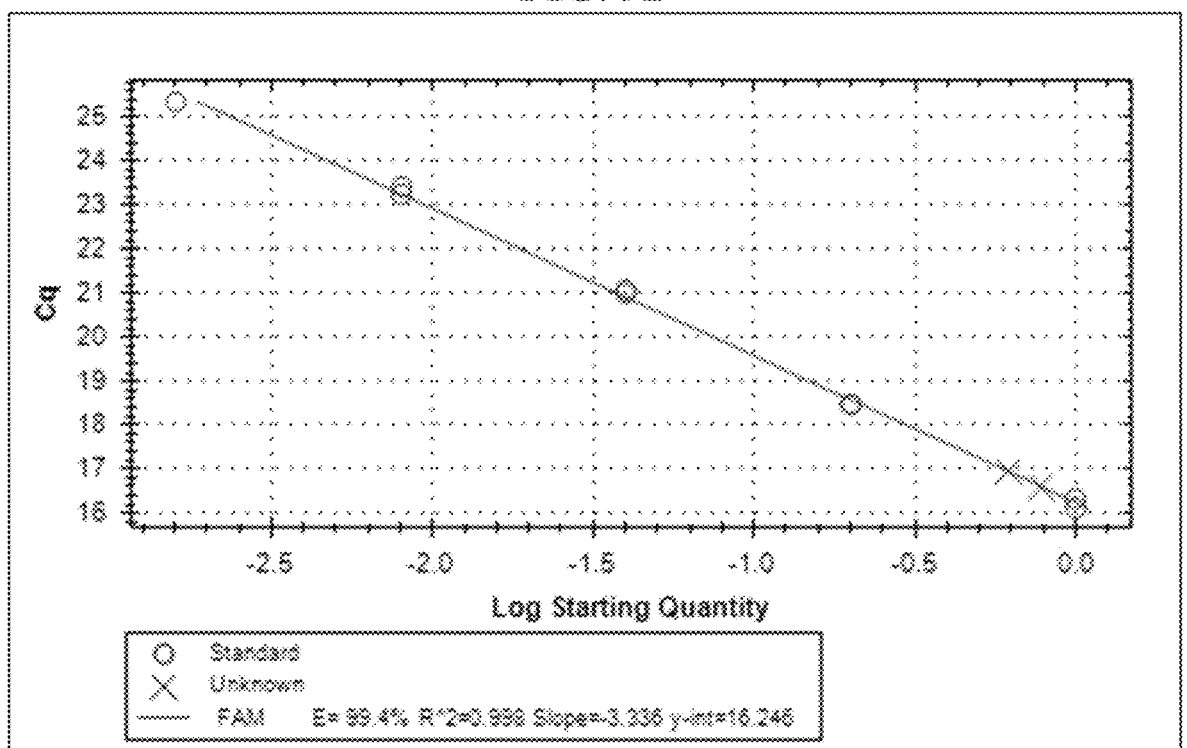
FIG. 9B shows a standard curve for the Yb8-80 target of a real-time PCR multiplex of the Yb8-80 and SVA-257 targets.
Figure 9C:
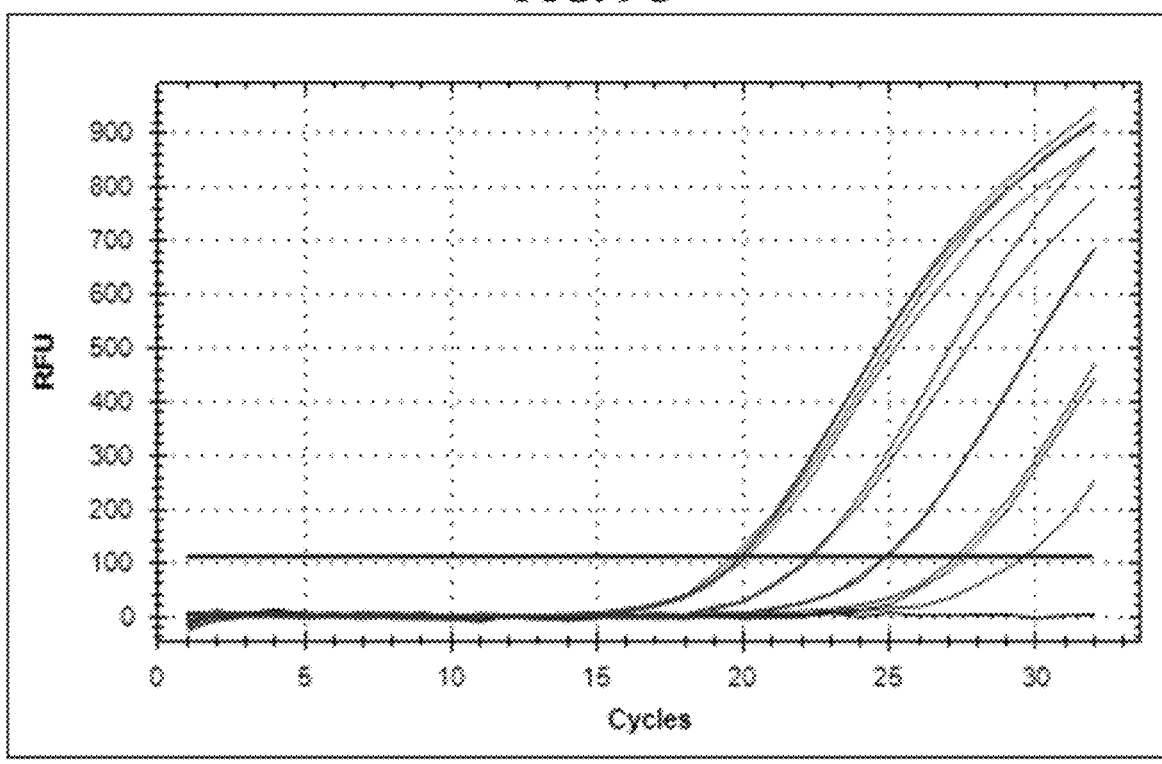
FIG. 9C shows an amplification plot for the SVA-257 target of a real-time PCR multiplex of the Yb8-80 and SVA-257 targets, the quantification of DNA in each sample being determined by use of a calibration curve with serial dilutions (1 ng, 200 pg, 40 pg, 8 pg, and 1.6 pg), with amplification of the SVA-257 target in purple, positive control in red and no template control in black.
Figure 9D:
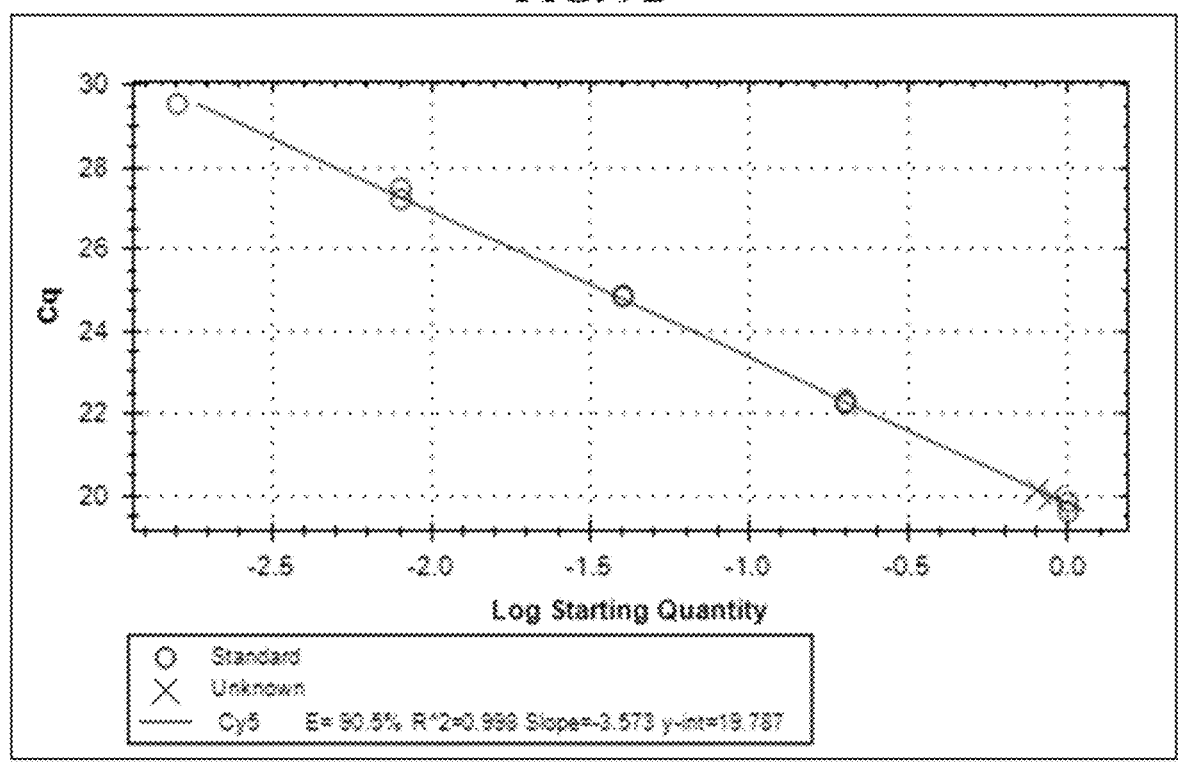
FIG. 9D shows a standard curve for the SVA-257 target of a real-time PCR multiplex of the Yb8-80 and SVA-257 targets.
Figure 9E:
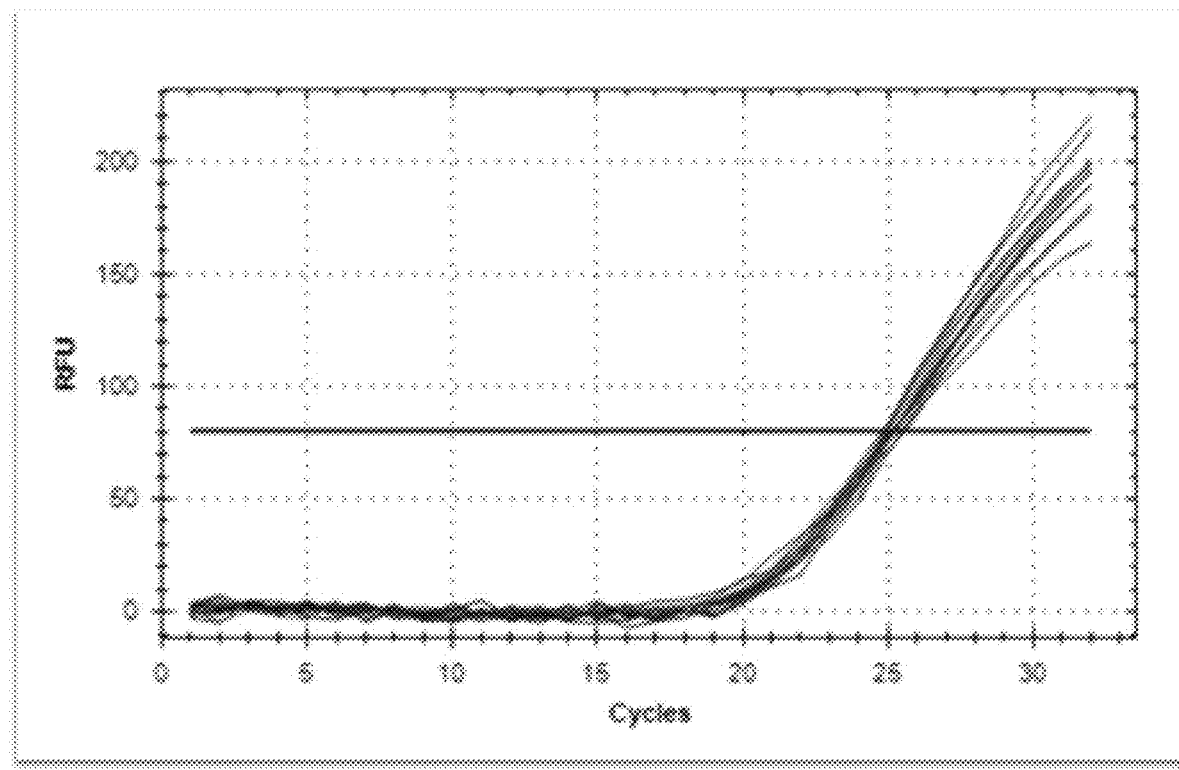
FIG. 9E shows an amplification plot of the internal positive control target within a real-time PCR multiplex of the Yb8-80 and SVA-257 targets, with amplification of the internal positive control target in blue.
Figure 10A:
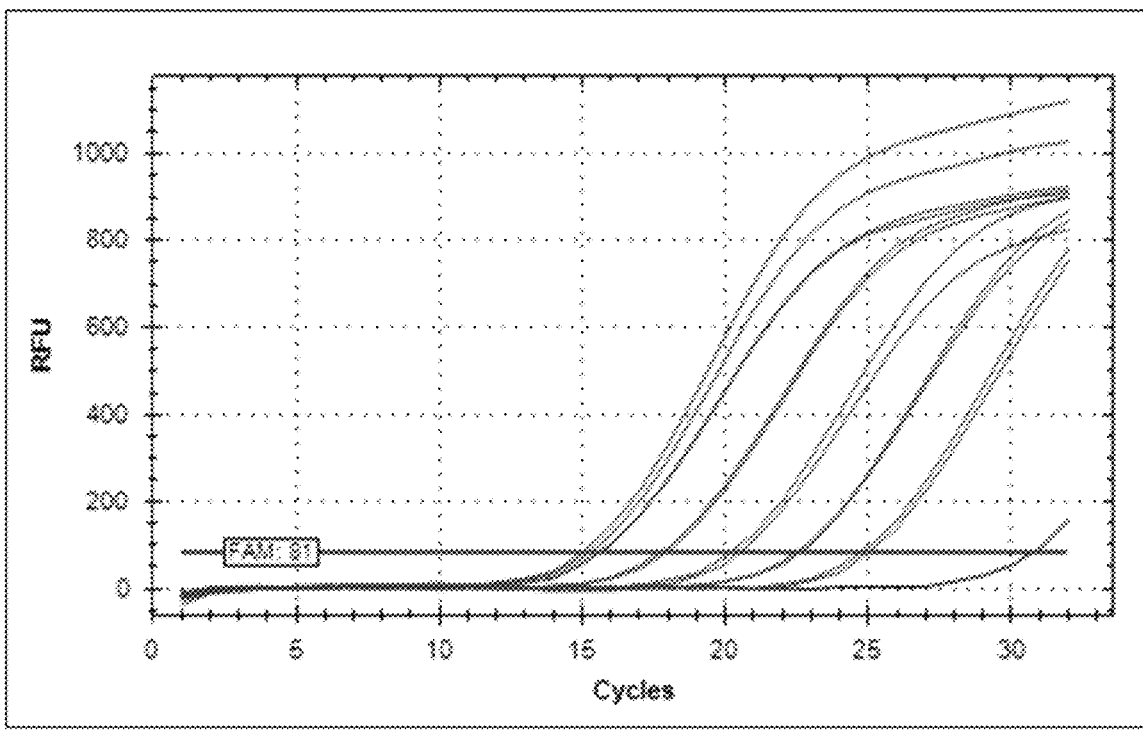
FIG. 10A shows an amplification plot for the Yb8-80 target of a real-time PCR multiplex of the Yb8-80 and SVA-265 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.
Figure 10B:
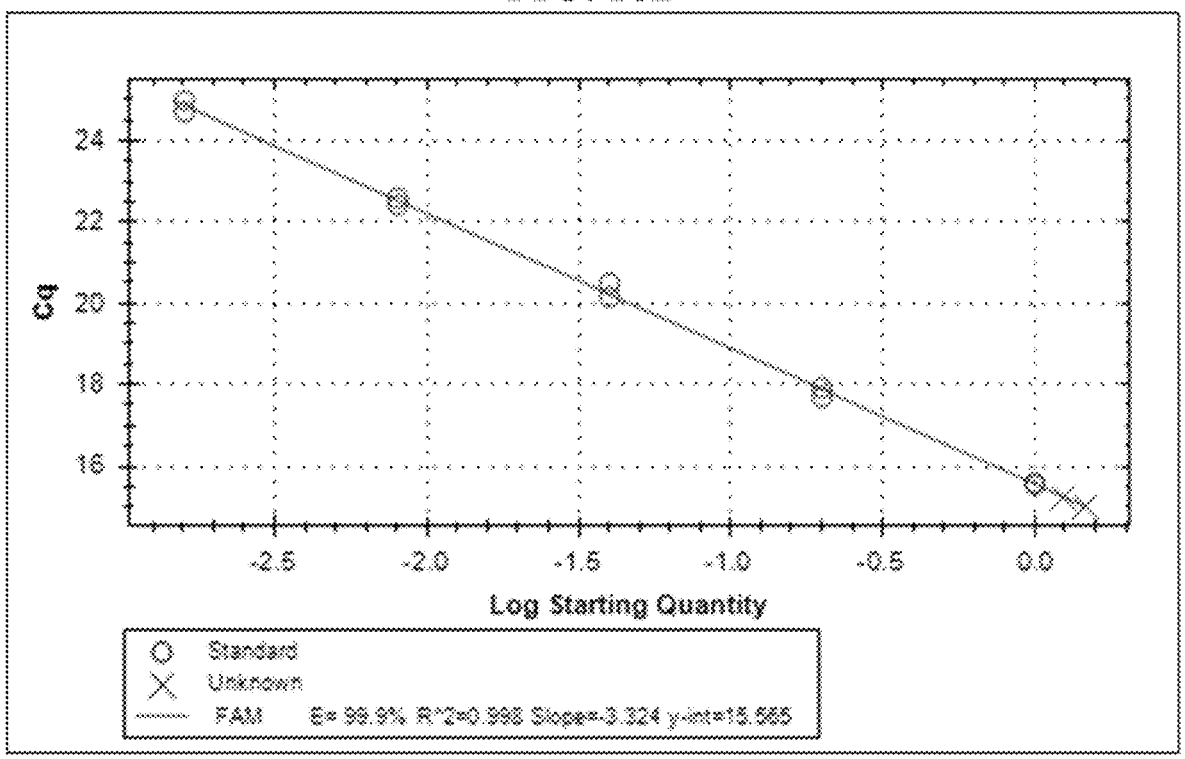
FIG. 10B shows a standard curve for the Yb8-80 target of a real-time PCR multiplex of the Yb8-80 and SVA-265 targets.
Figure 10C:
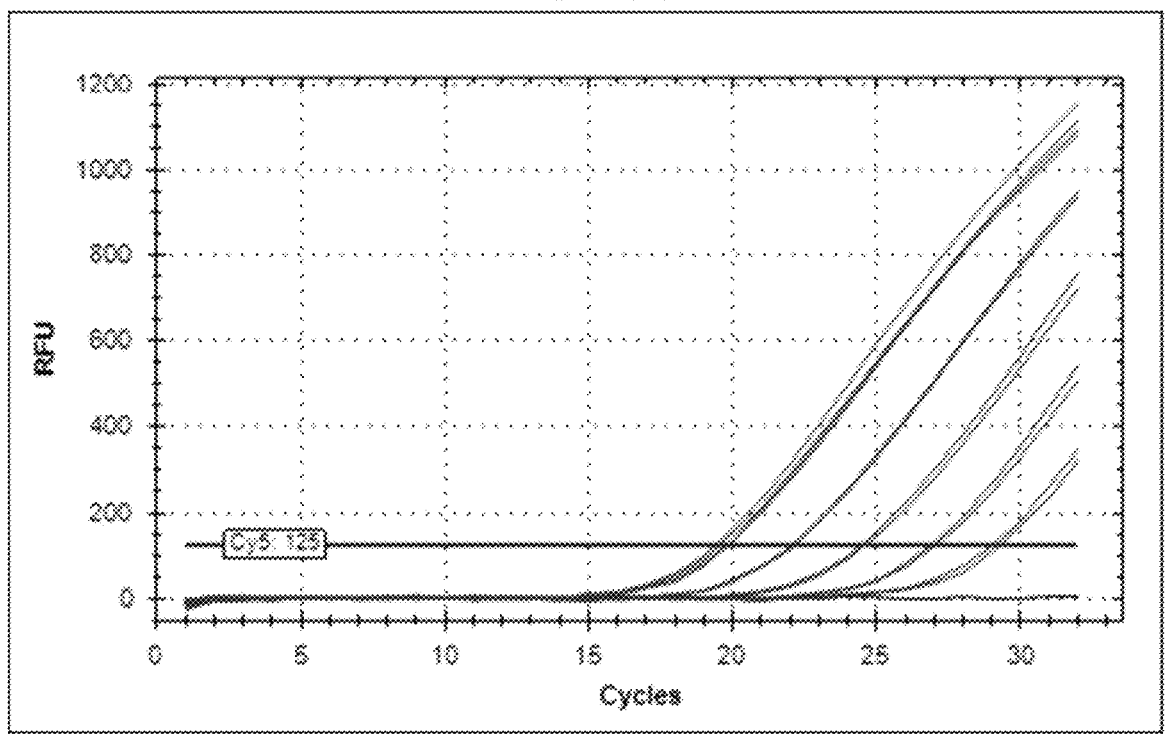
FIG. 10C shows an amplification plot for the SVA-265 target of a real-time PCR multiplex of the Yb8-80 and SVA-265 targets, the quantification of DNA in each sample being determined by use of a calibration curve with serial dilutions (1 ng, 200 pg, 40 pg, 8 pg, and 1.6 pg), with amplification of the SVA-265 target in purple, positive control in red and no template control in black.
Figure 10D:
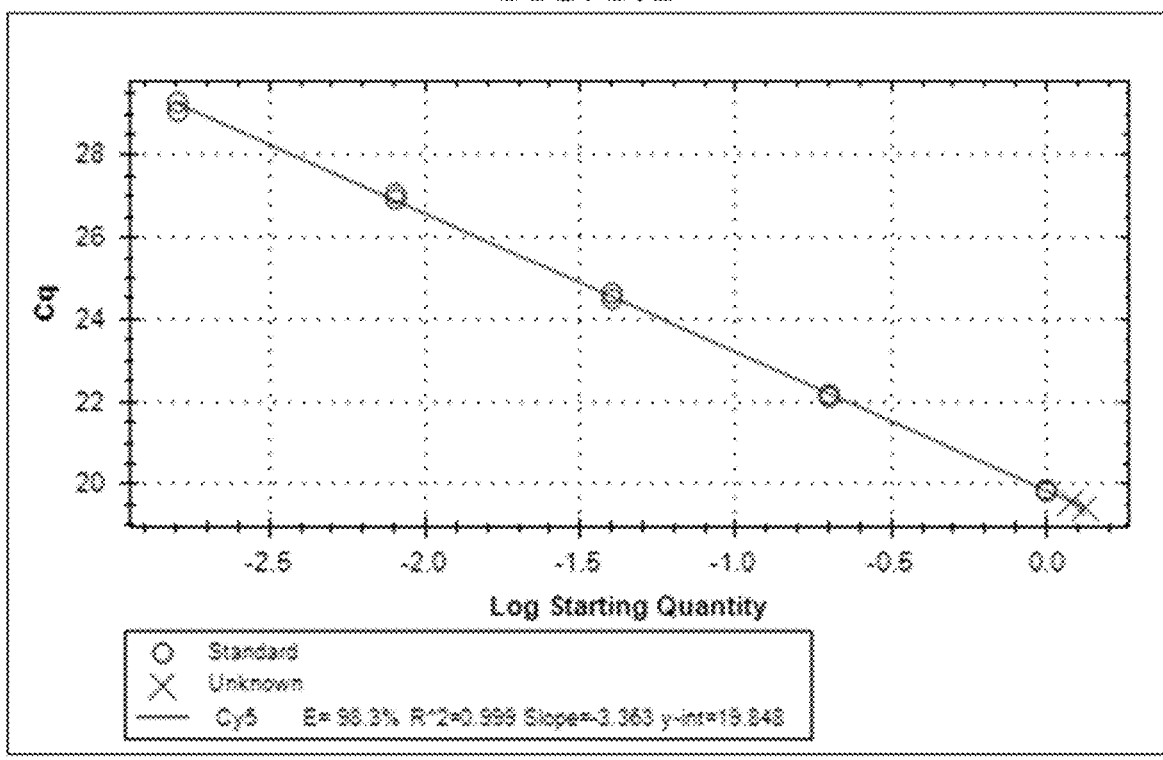
FIG. 10D shows a standard curve for the SVA-265 target of a real-time PCR multiplex of the Yb8-80 and SVA-265 targets.
Figure 10E:
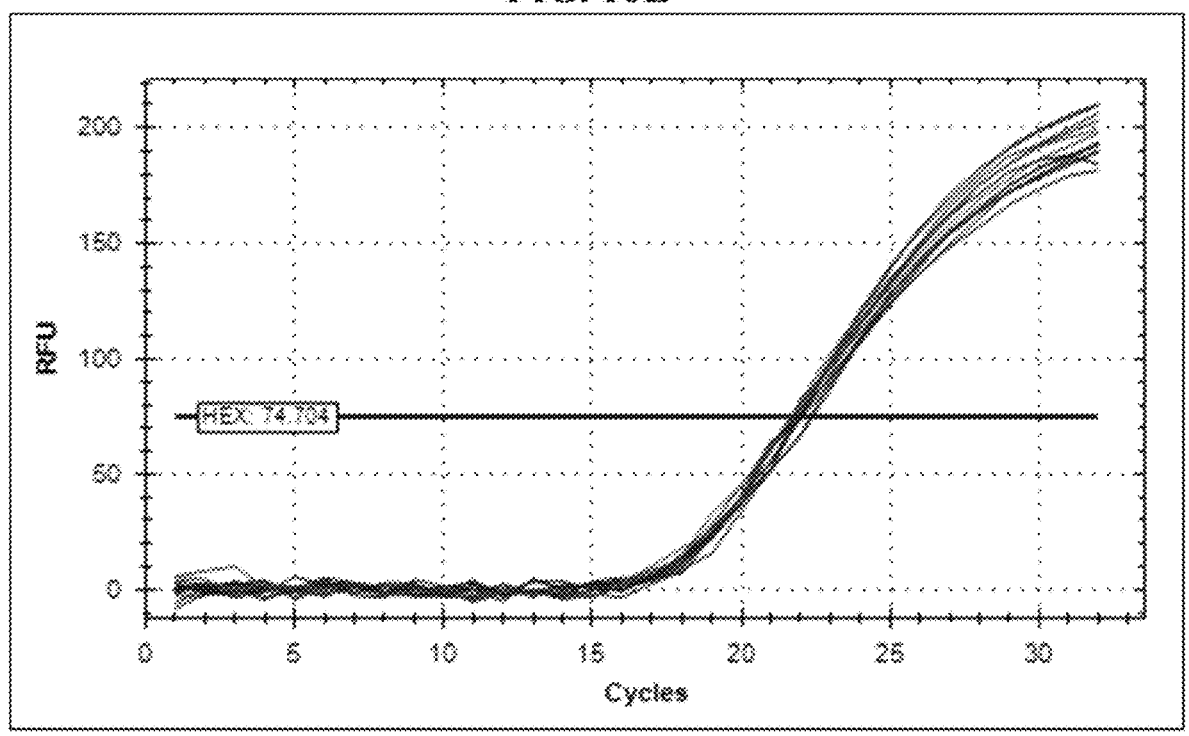
FIG. 10E shows an amplification plot of the internal positive control target within a real-time PCR multiplex of the Yb8-80 and SVA-265 targets, with amplification of the internal positive control target in blue.
Figure 11A:
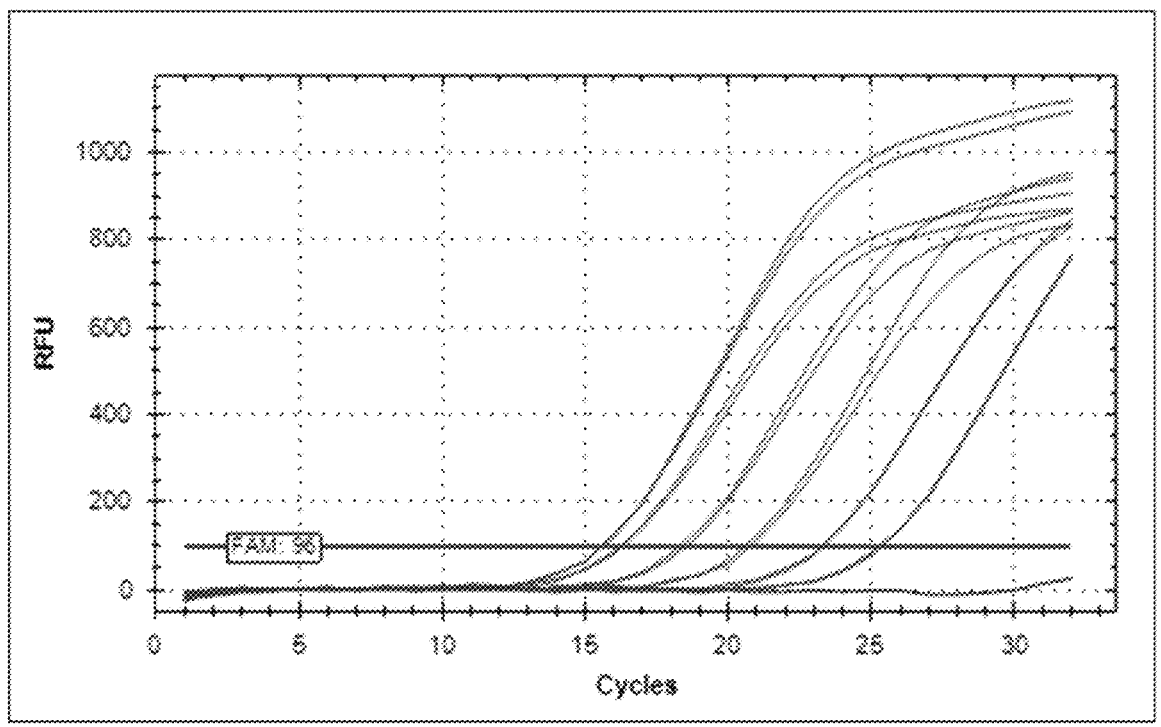
FIG. 11A shows an amplification plot for the Yb8-80 target of a real-time PCR multiplex of the Yb8-80 and SVA-290 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.
Figure 11B:
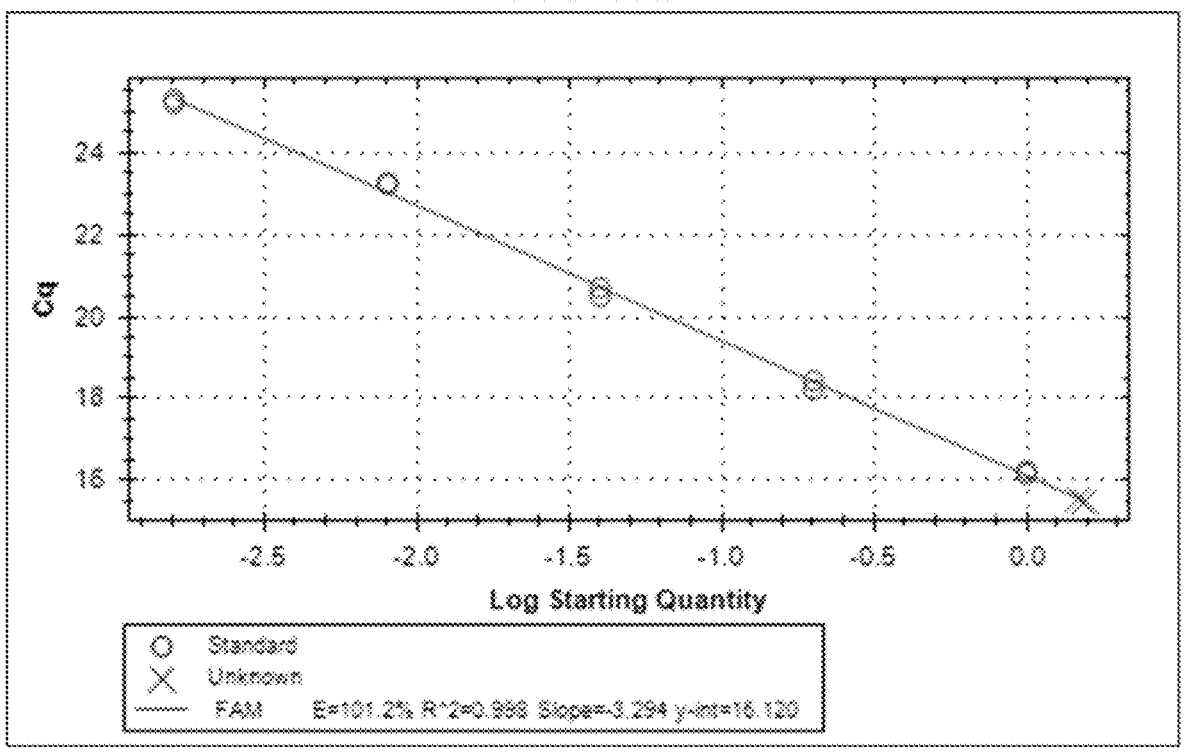
FIG. 11B shows a standard curve for the Yb8-80 target of a real-time PCR multiplex of the Yb8-80 and SVA-290 targets.
Figure 11C:
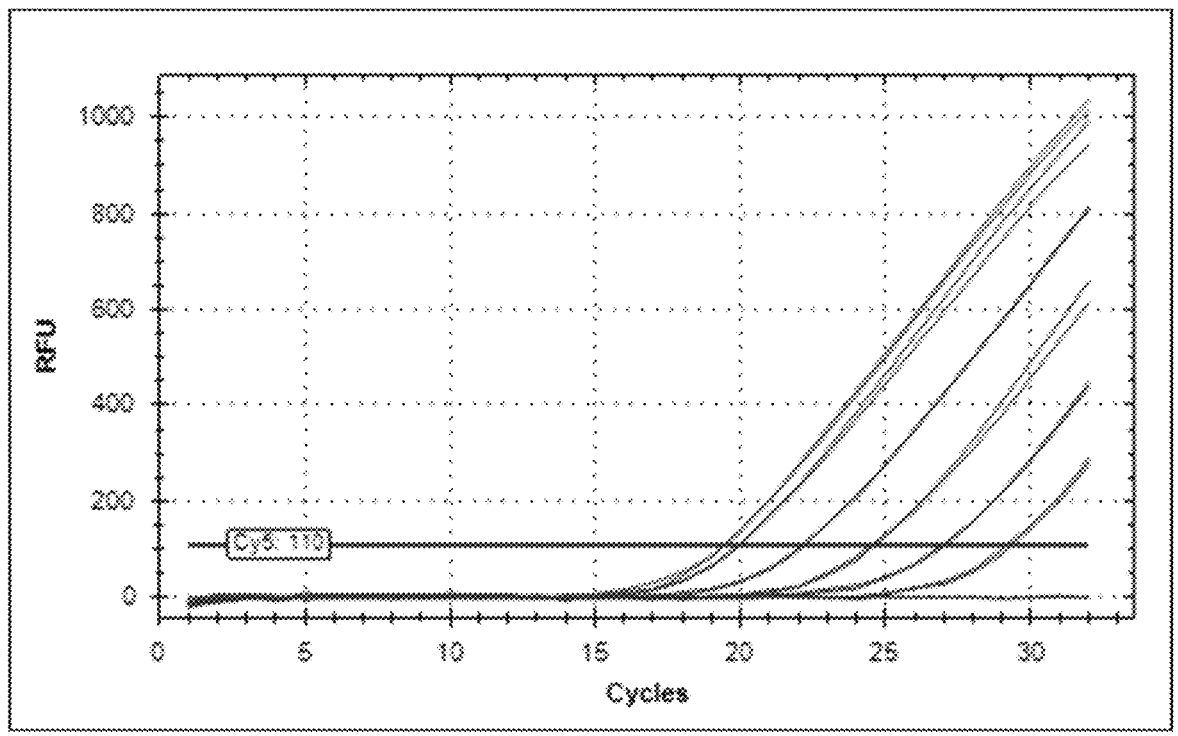
FIG. 11C shows an amplification plot for the SVA-290 target of a real-time PCR multiplex of the Yb8-80 and SVA-290 targets, the quantification of DNA in each sample being determined by use of a calibration curve with serial dilutions (1 ng, 200 pg, 40 pg, 8 pg, and 1.6 pg), with amplification of the SVA-290 target in purple, positive control in red and no template control in black.
Figure 11D:
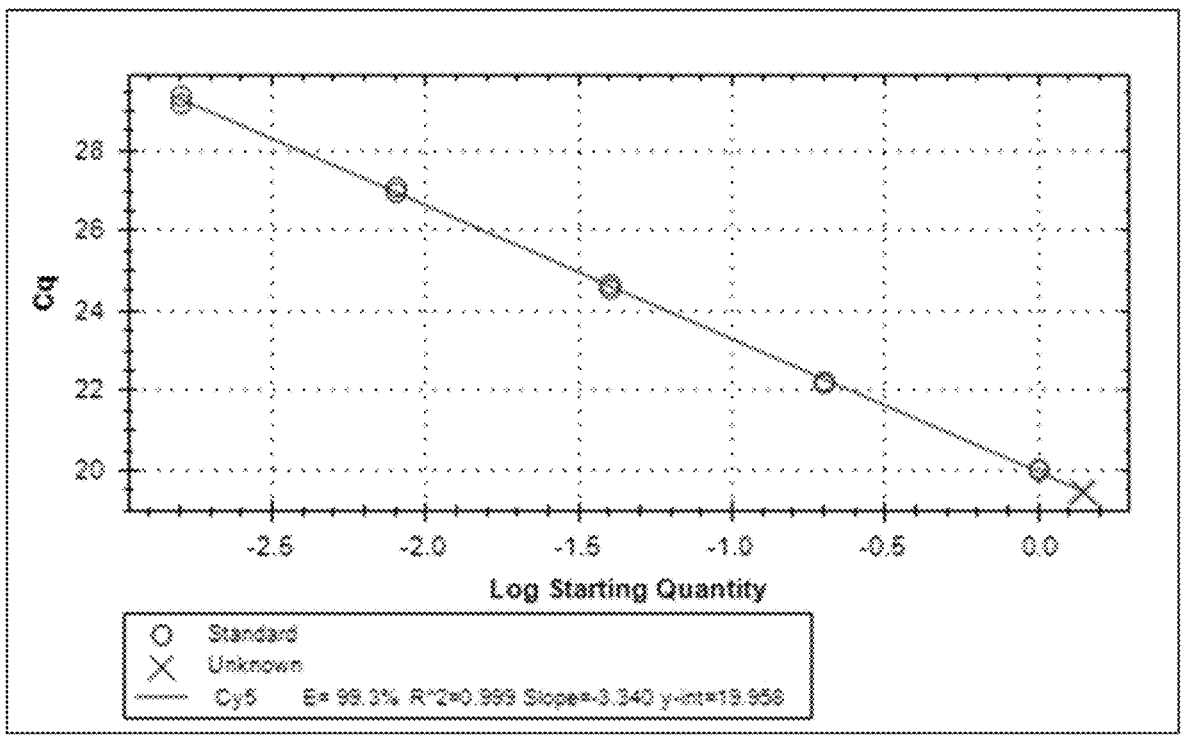
FIG. 11D shows a standard curve for the SVA-290 target of a real-time PCR multiplex of the Yb8-80 and SVA-290 targets.
Figure 11E:
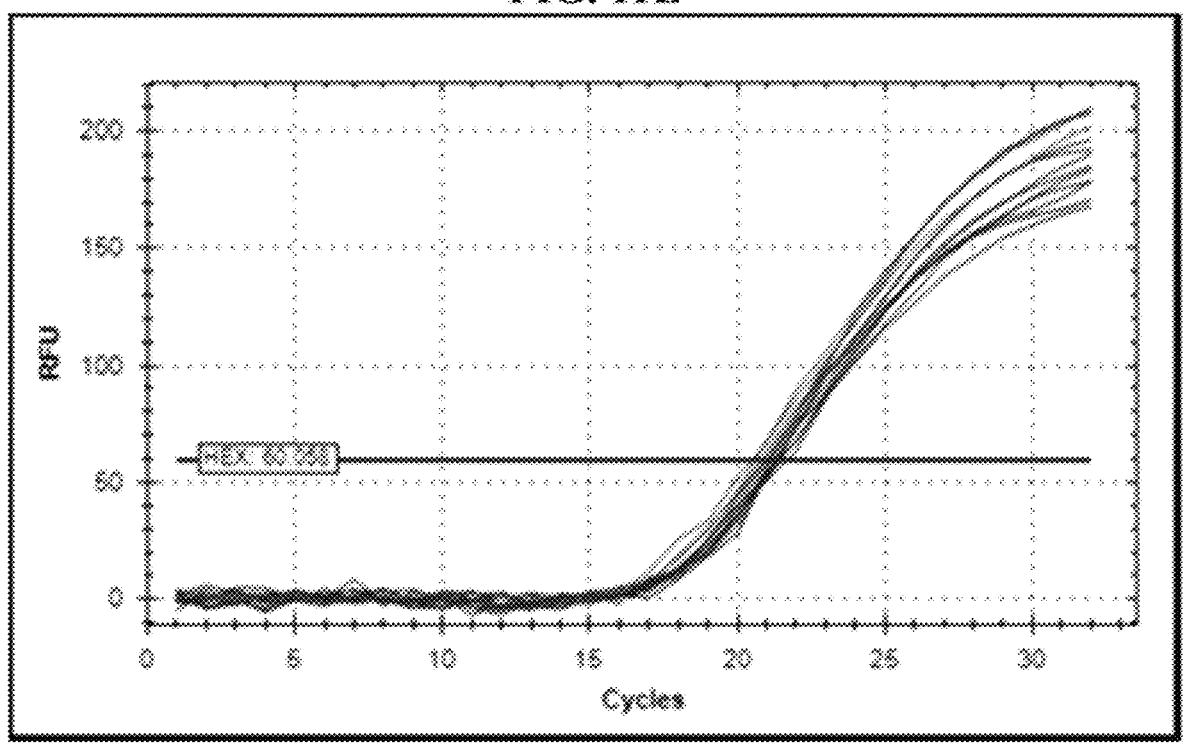
FIG. 11E shows an amplification plot of the internal positive control target within a real-time PCR multiplex of the Yb8-80 and SVA-290 targets, with amplification of the internal positive control target in blue.
Figure 12A:
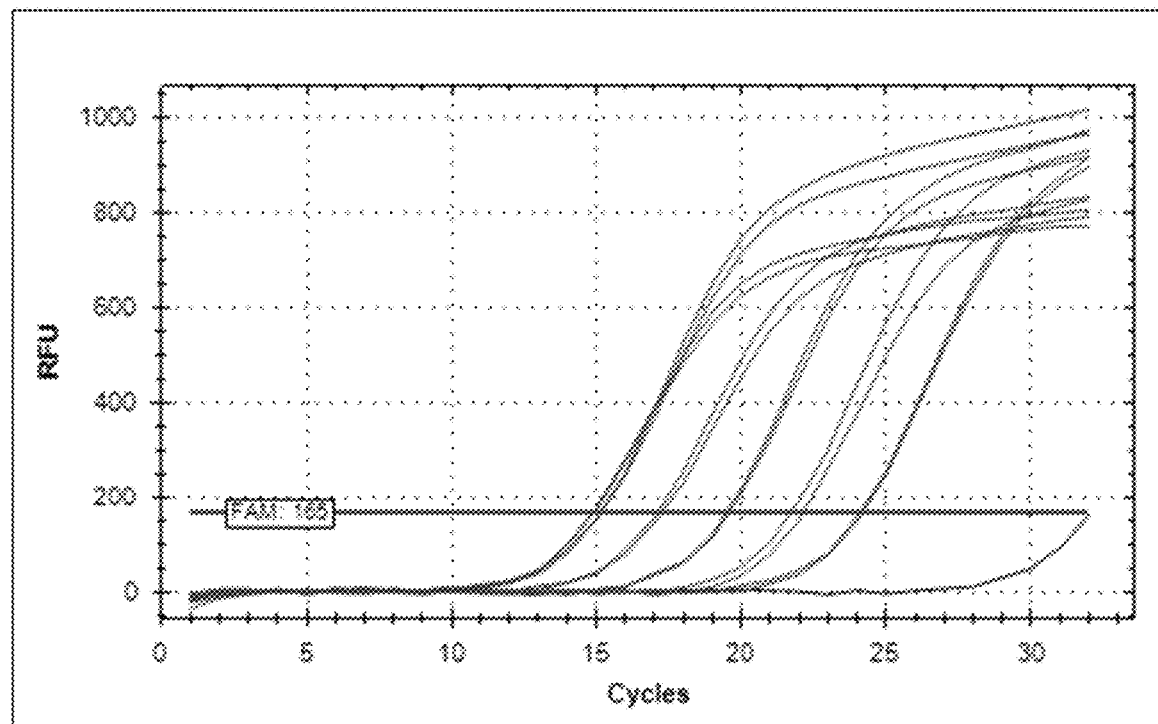
FIG. 12A shows an amplification plot for the Yb8-120 target of a real-time PCR multiplex of the Yb8-120 and SVA-207 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.
Figure 12B:
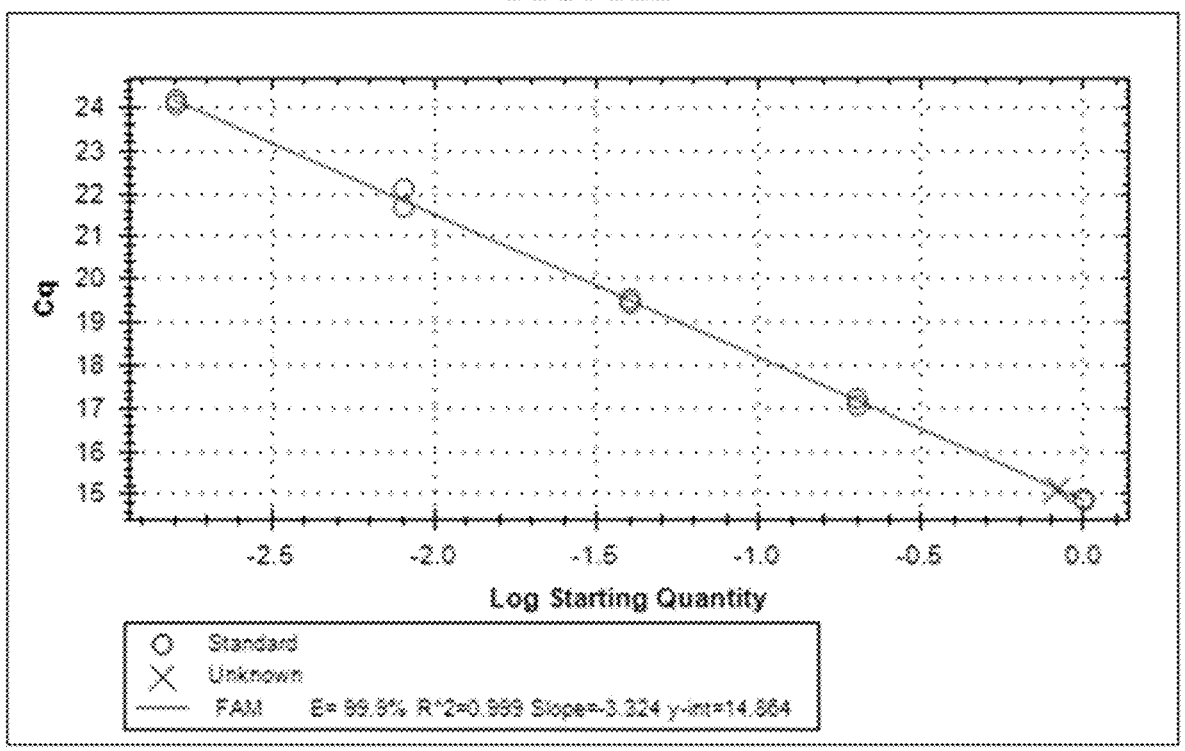
FIG. 12B shows a standard curve for the Yb8-120 target of a real-time PCR multiplex of the Yb8-120 and SVA-207 targets.
Figure 12C:
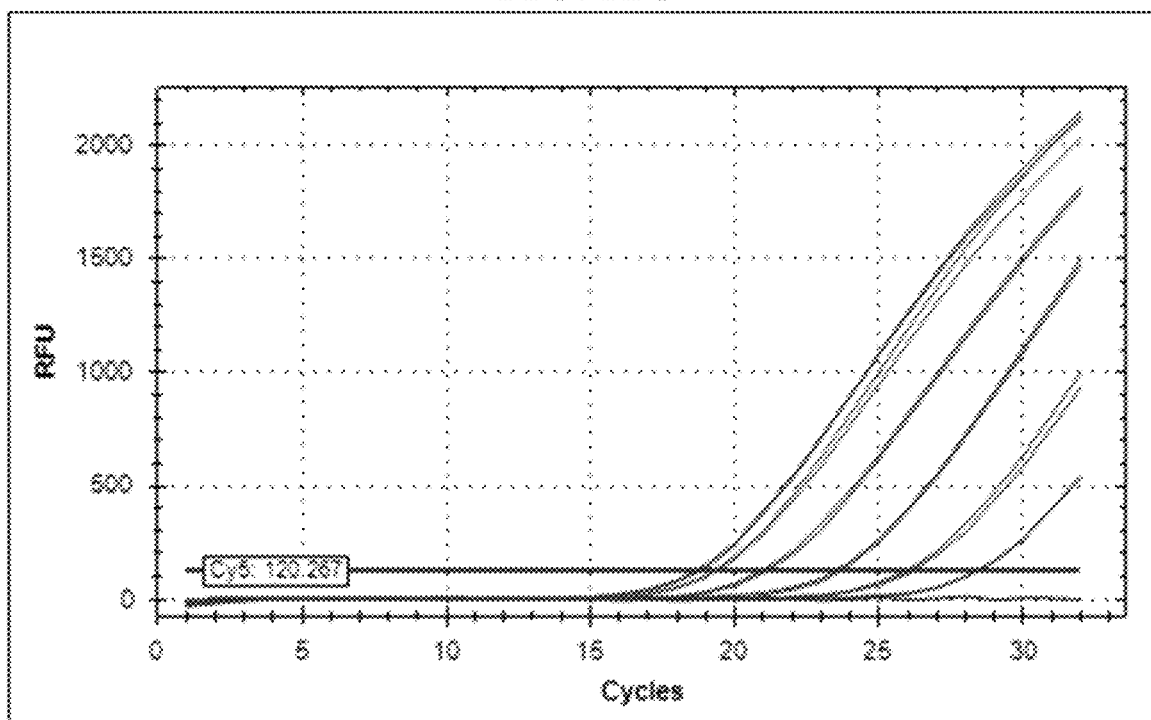
FIG. 12C shows an amplification plot for the SVA-207 target of a real-time PCR multiplex of the Yb8-120 and SVA-207 targets, the quantification of DNA in each sample being determined by use of a calibration curve with serial dilutions (1 ng, 200 pg, 40 pg, 8 pg, and 1.6 pg), with amplification of the SVA-207 target in purple, positive control in red and no template control in black.
Figure 12D:
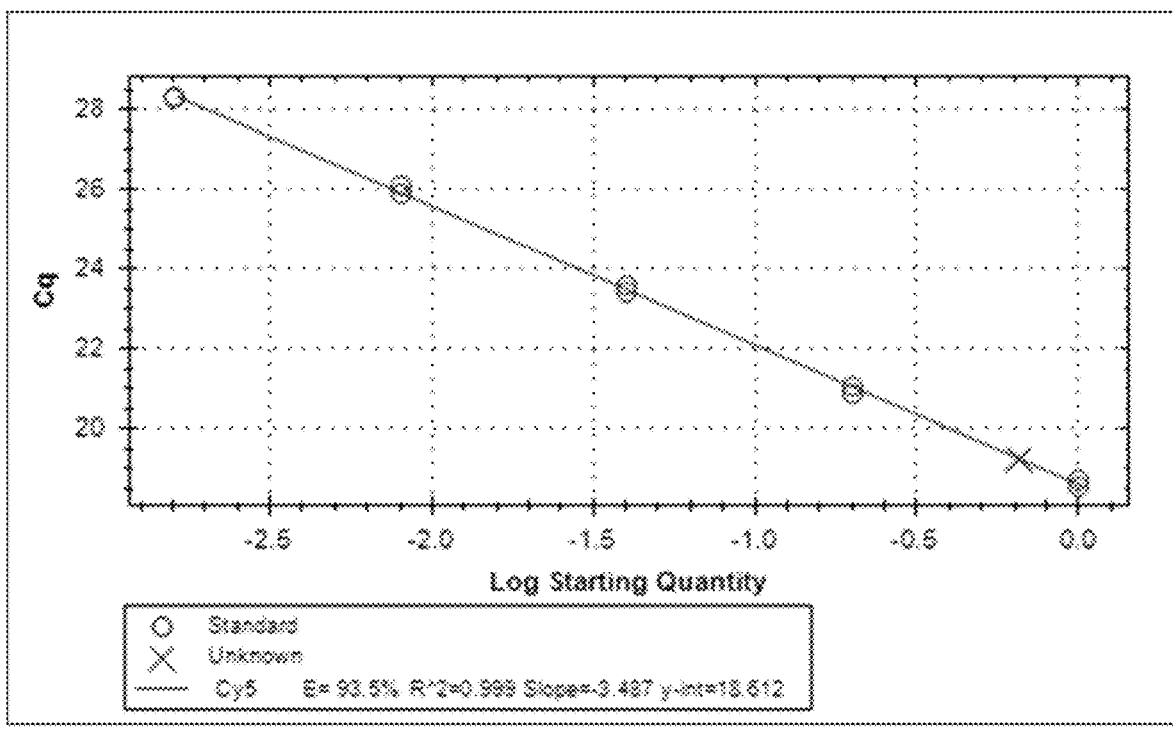
FIG. 12D shows a standard curve for the SVA-207 target of a real-time PCR multiplex of the Yb8-120 and SVA-207 targets.
Figure 12E:
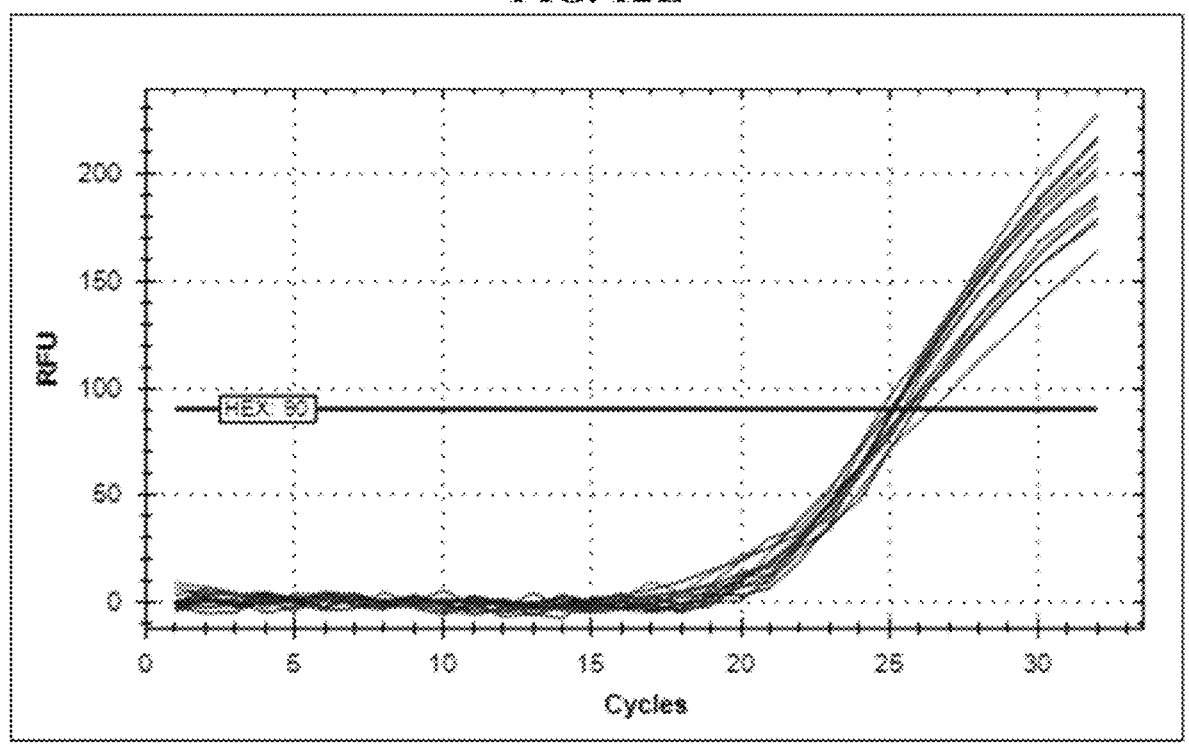
FIG. 12E shows an amplification plot of the internal positive control target within a real-time PCR multiplex of the Yb8-120 and SVA-207 targets, with amplification of the internal positive control target in blue.
Figure 13A:
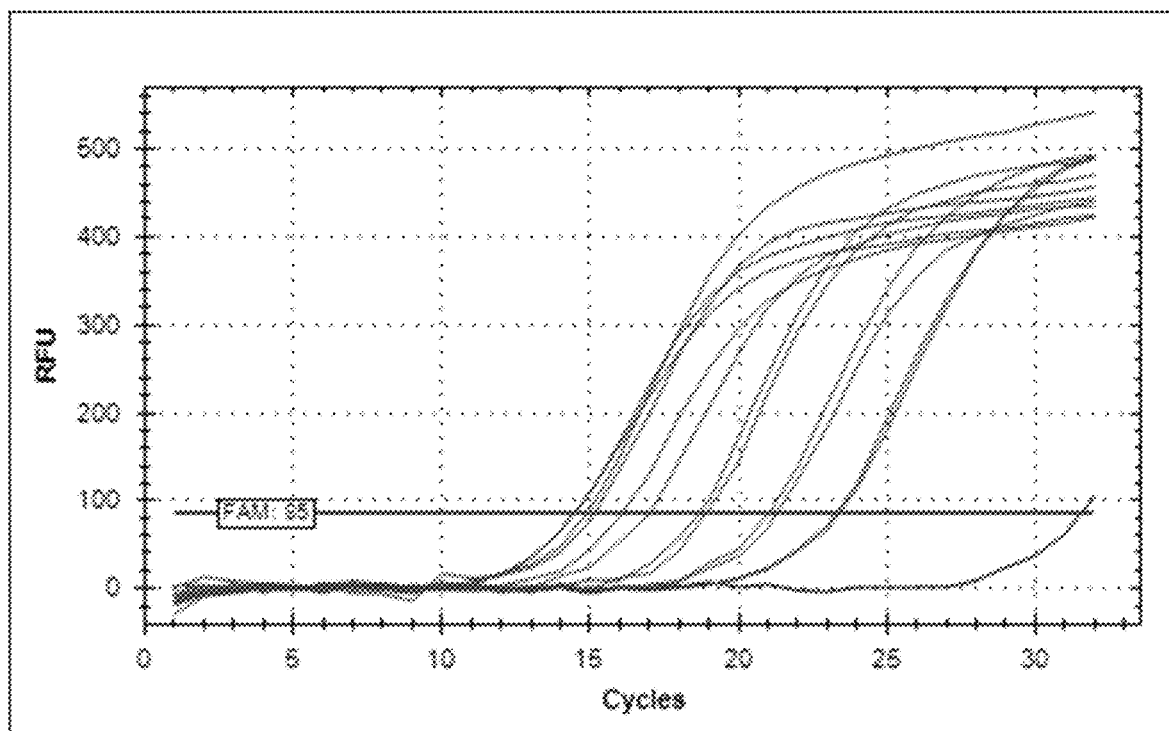
FIG. 13A shows an amplification plot for the Yb8-120 target of a real-time PCR multiplex of the Yb8-120 and SVA-257 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.
Figure 13B:
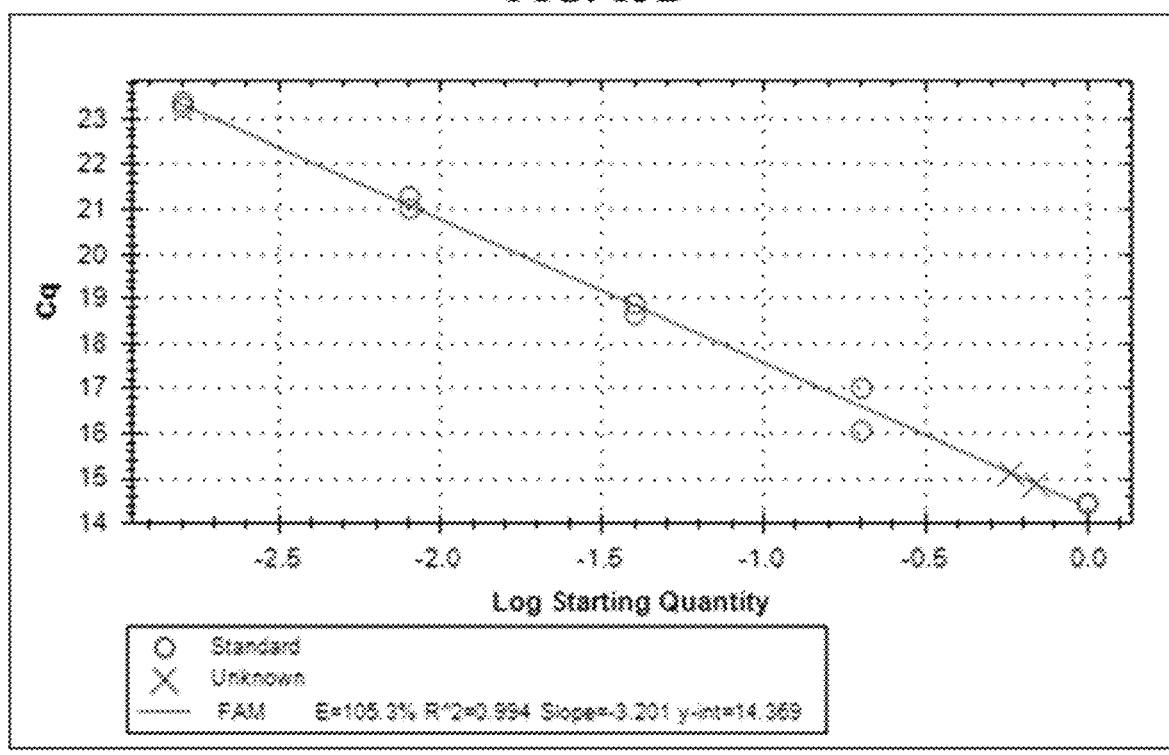
FIG. 13B shows a standard curve for the Yb8-120 target of a real-time PCR multiplex of the Yb8-120 and SVA-257 targets.
Figure 13C:
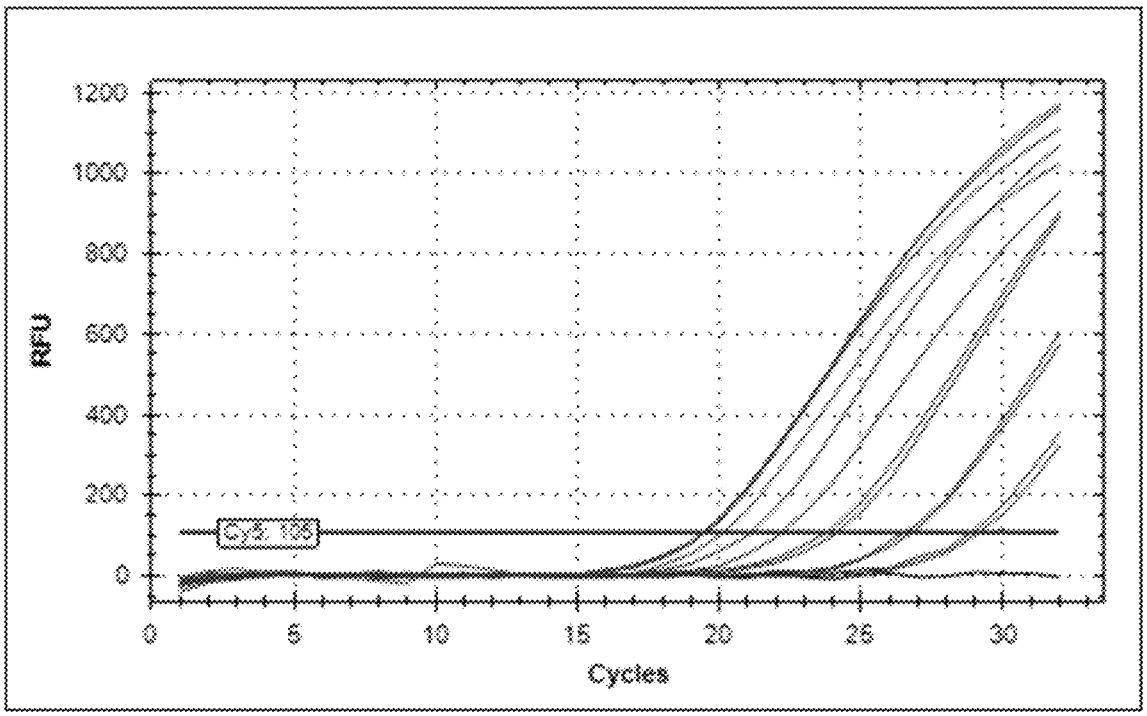
FIG. 13C shows an amplification plot for the SVA-257 target of a real-time PCR multiplex of the Yb8-120 and SVA-257 targets, the quantification of DNA in each sample being determined by use of a calibration curve with serial dilutions (1 ng, 200 pg, 40 pg, 8 pg, and 1.6 pg), with amplification of the SVA-257 target in purple, positive control in red and no template control in black.
Figure 13D:
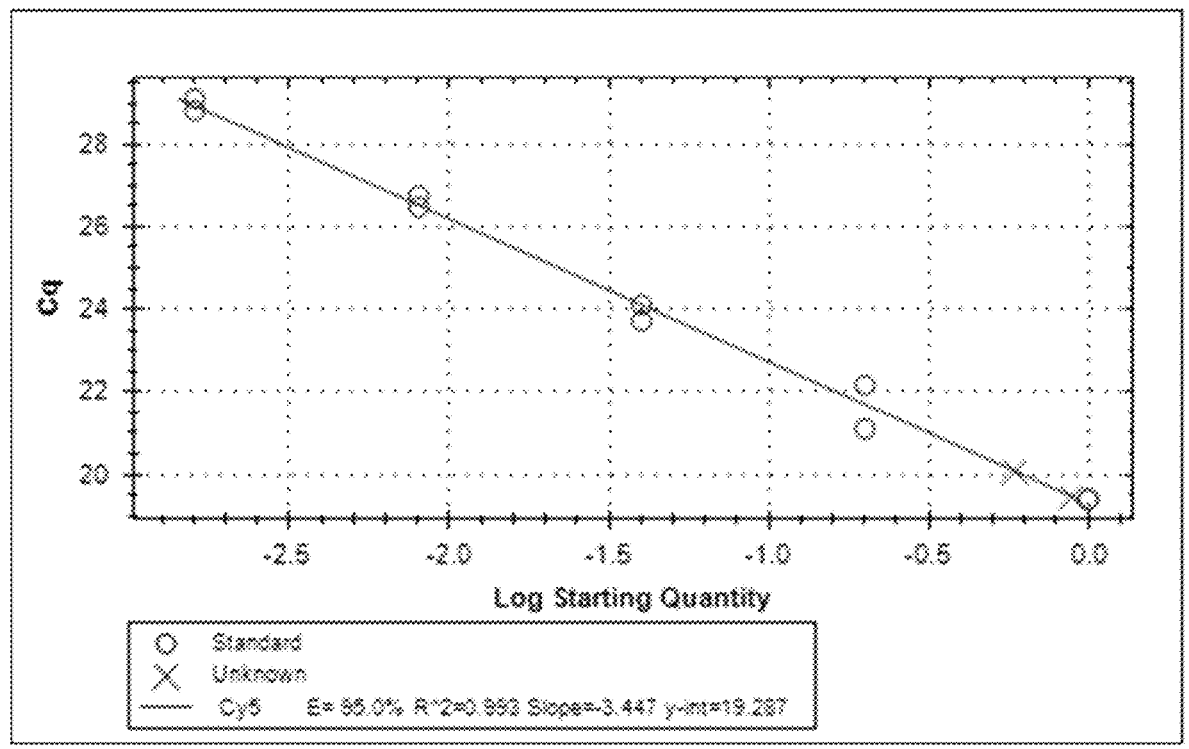
FIG. 13D shows a standard curve for the SVA-257 target of a real-time PCR multiplex of the Yb8-120 and SVA-257 targets.
Figure 13E:
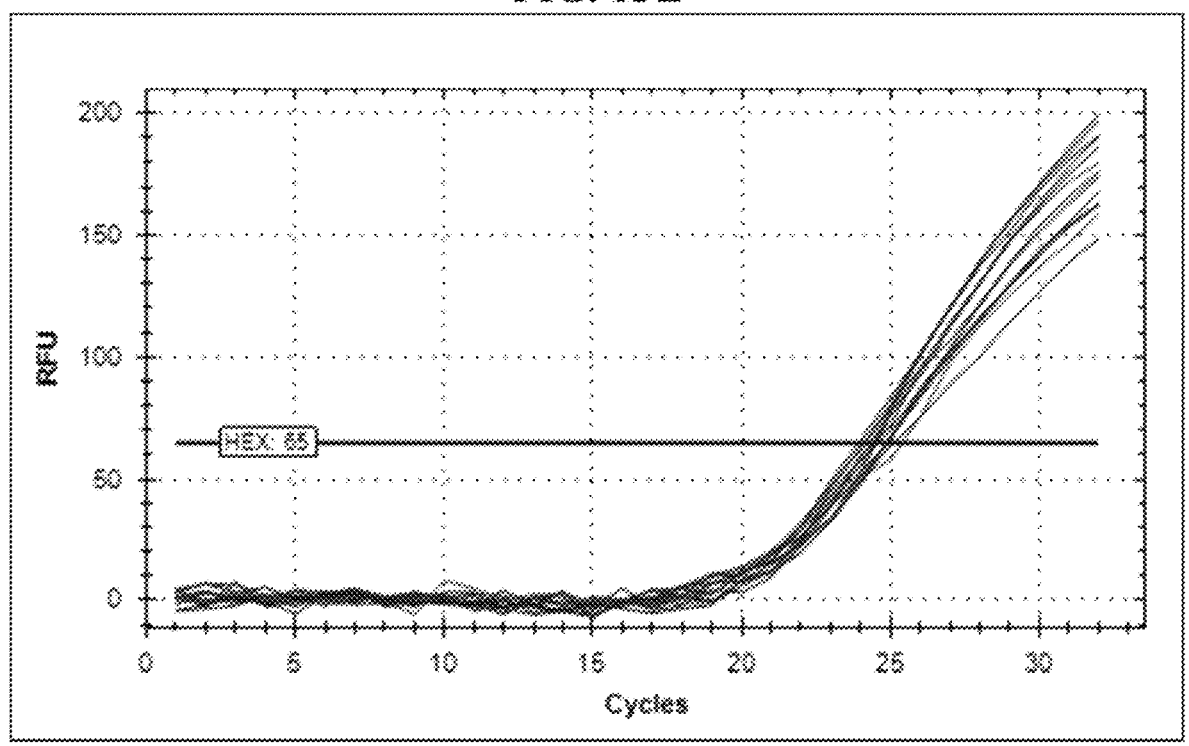
FIG. 13E shows an amplification plot of the internal positive control target within a real-time PCR multiplex of the Yb8-120 and SVA-257 targets, with amplification of the internal positive control target in blue.
Figure 14A:
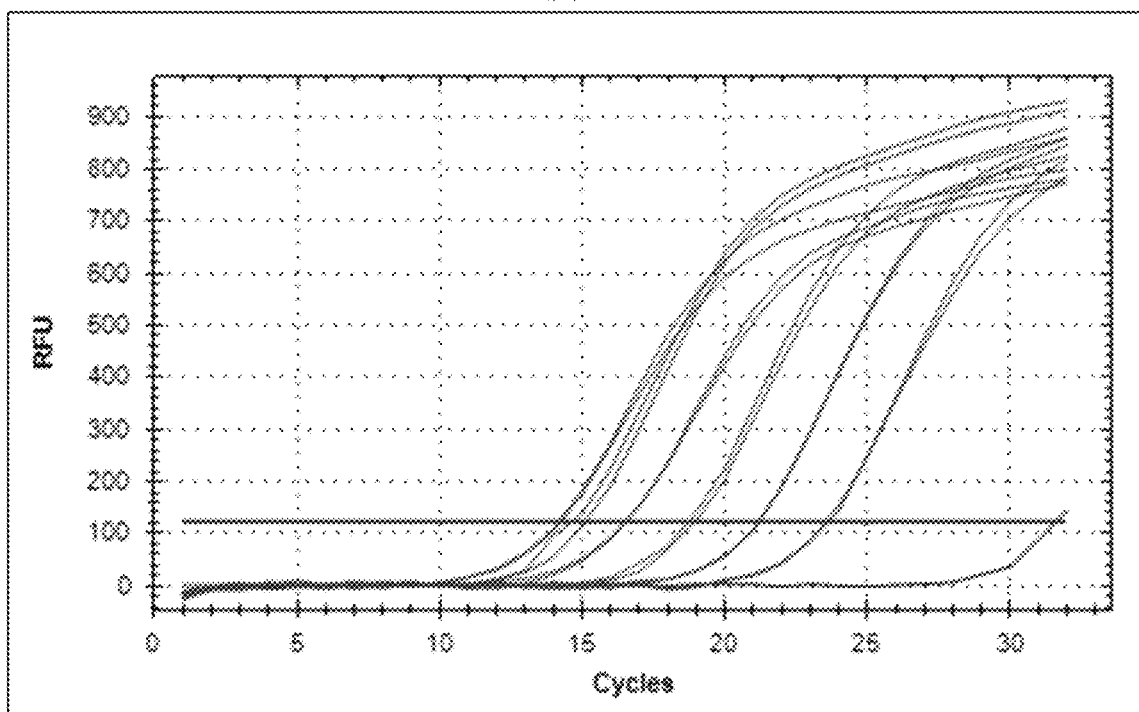
FIG. 14A shows an amplification plot for the Yb8-120 target of a real-time PCR multiplex of the Yb8-120 and SVA-265 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.
Figure 14B:
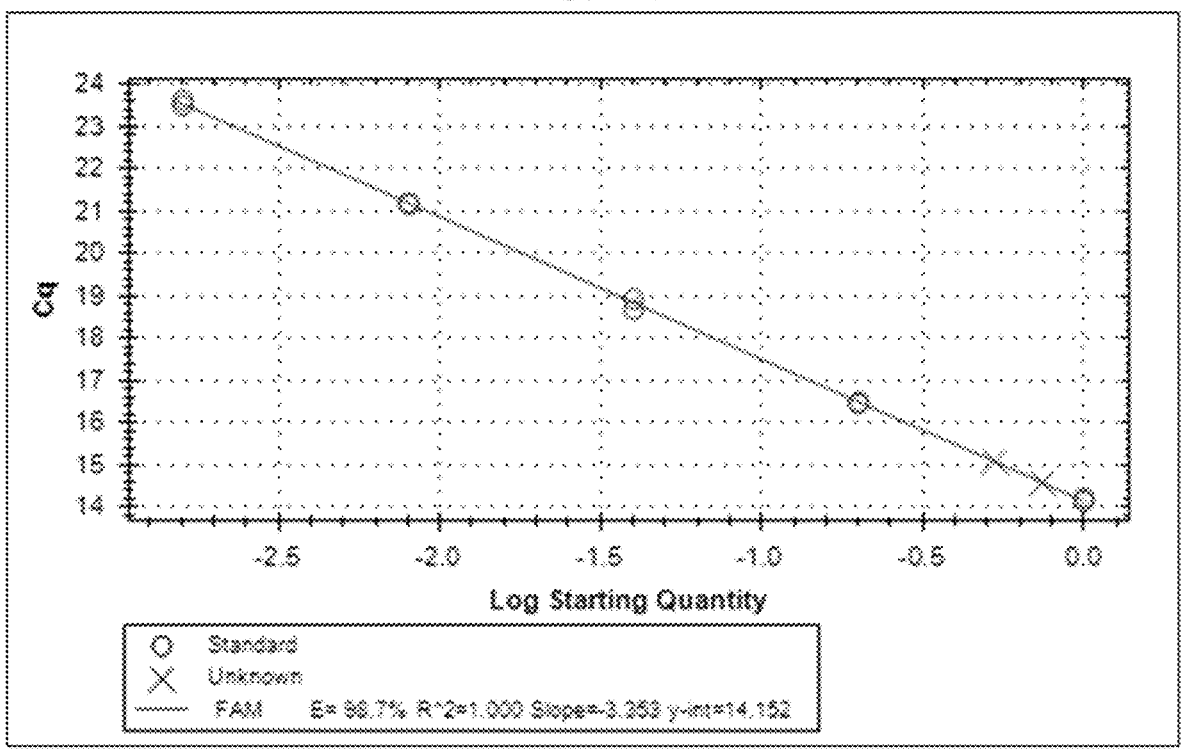
FIG. 14B shows a standard curve for the Yb8-120 target of a real-time PCR multiplex of the Yb8-120 and SVA-265 targets.
Figure 14C:
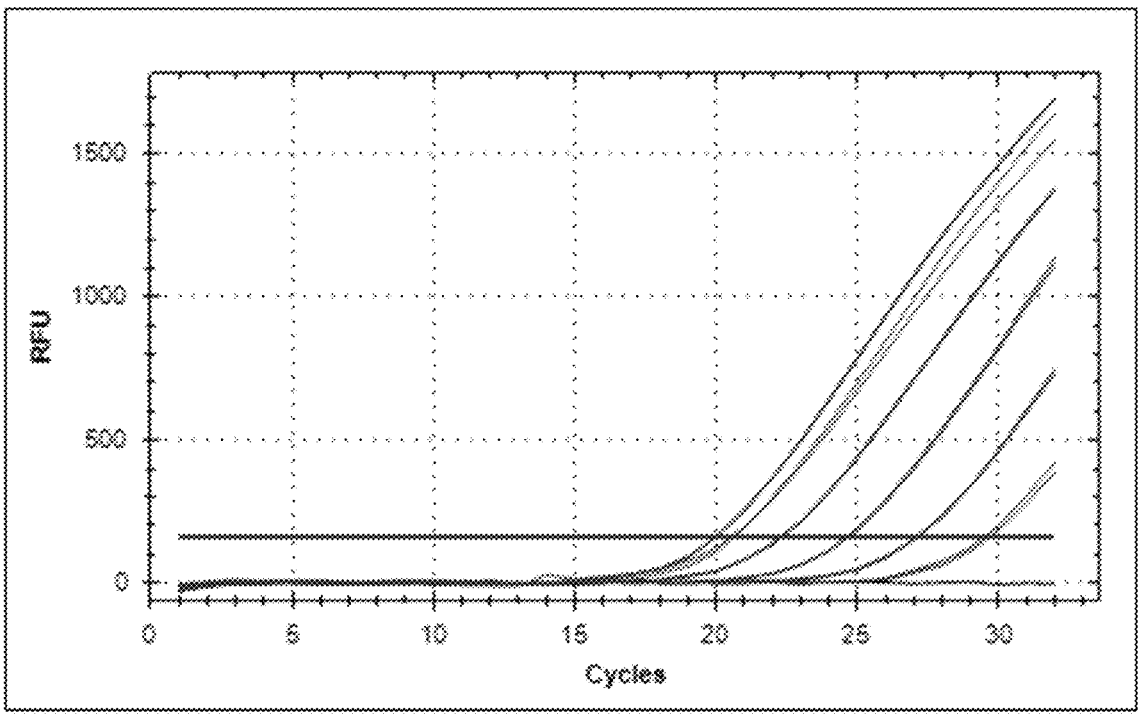
FIG. 14C shows an amplification plot for the SVA-265 target of a real-time PCR multiplex of the Yb8-120 and SVA-265 targets, the quantification of DNA in each sample being determined by use of a calibration curve with serial dilutions (1 ng, 200 pg, 40 pg, 8 pg, and 1.6 pg), with amplification of the SVA-265 target in purple, positive control in red and no template control in black.
Figure 14D:
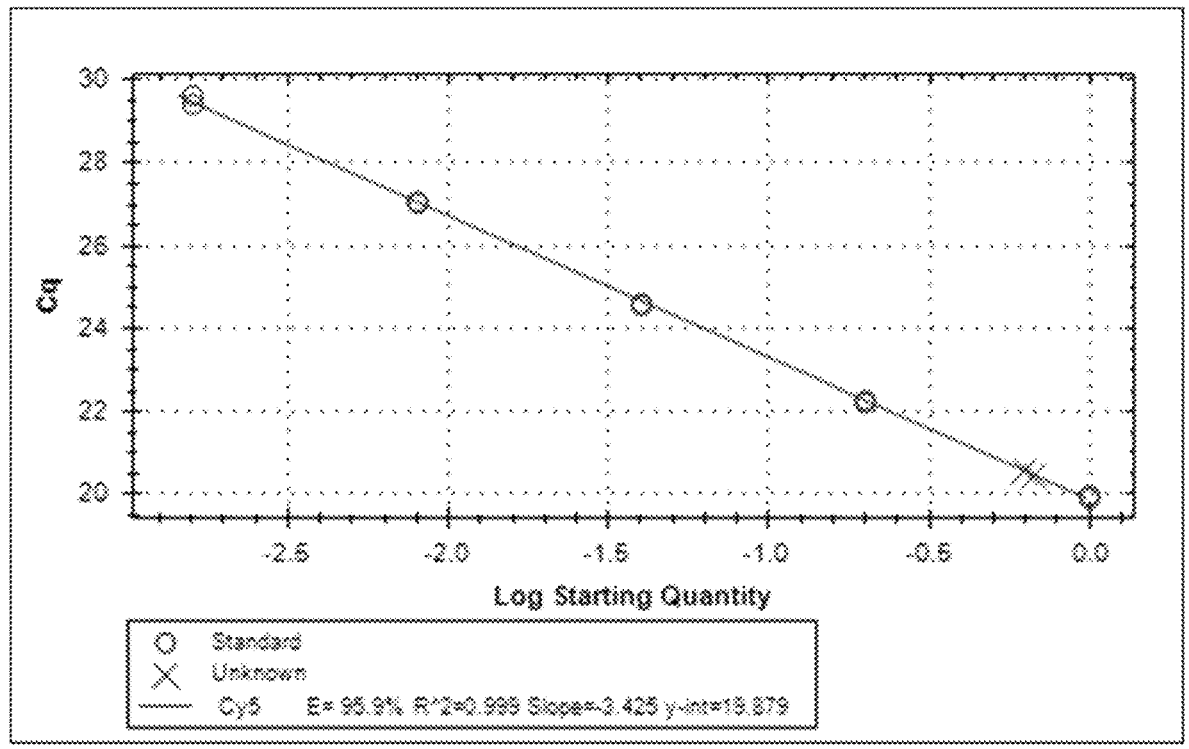
FIG. 14D shows a standard curve for the SVA-265 target of a real-time PCR multiplex of the Yb8-120 and SVA-265 targets.
Figure 14E:
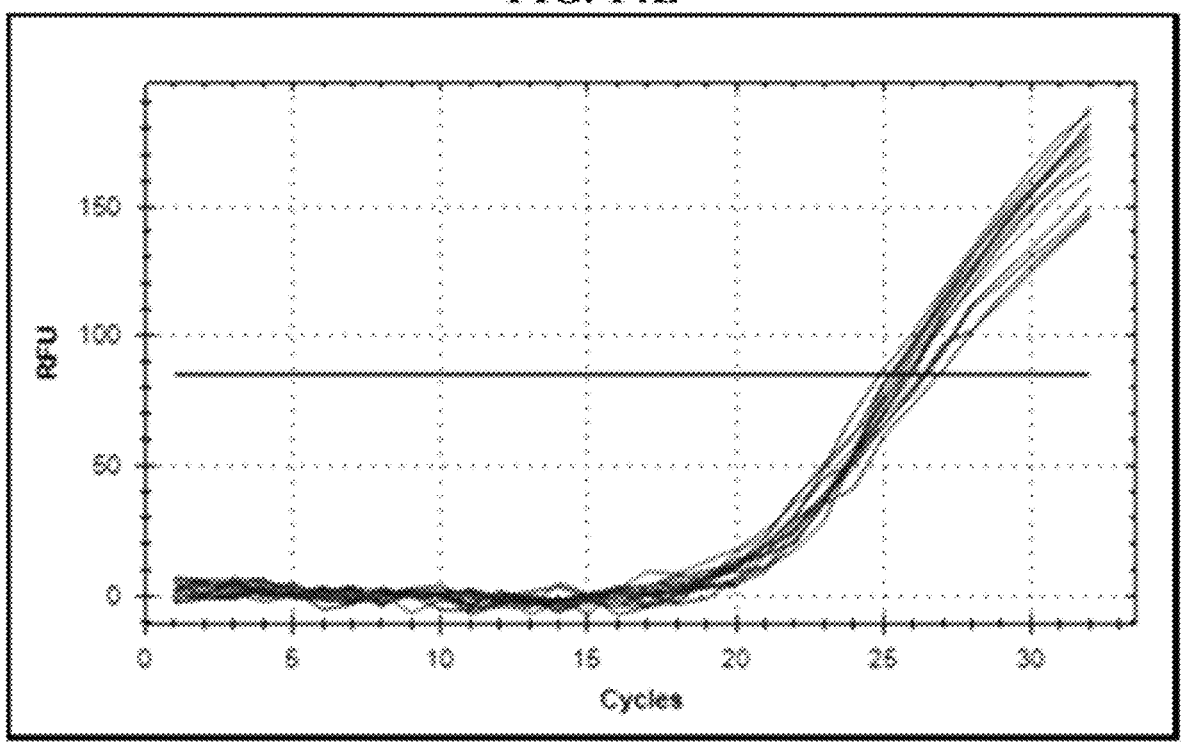
FIG. 14E shows an amplification plot of the internal positive control target within a real-time PCR multiplex of the Yb8-120 and SVA-265 targets, with amplification of the internal positive control target in blue.
Figure 15A:
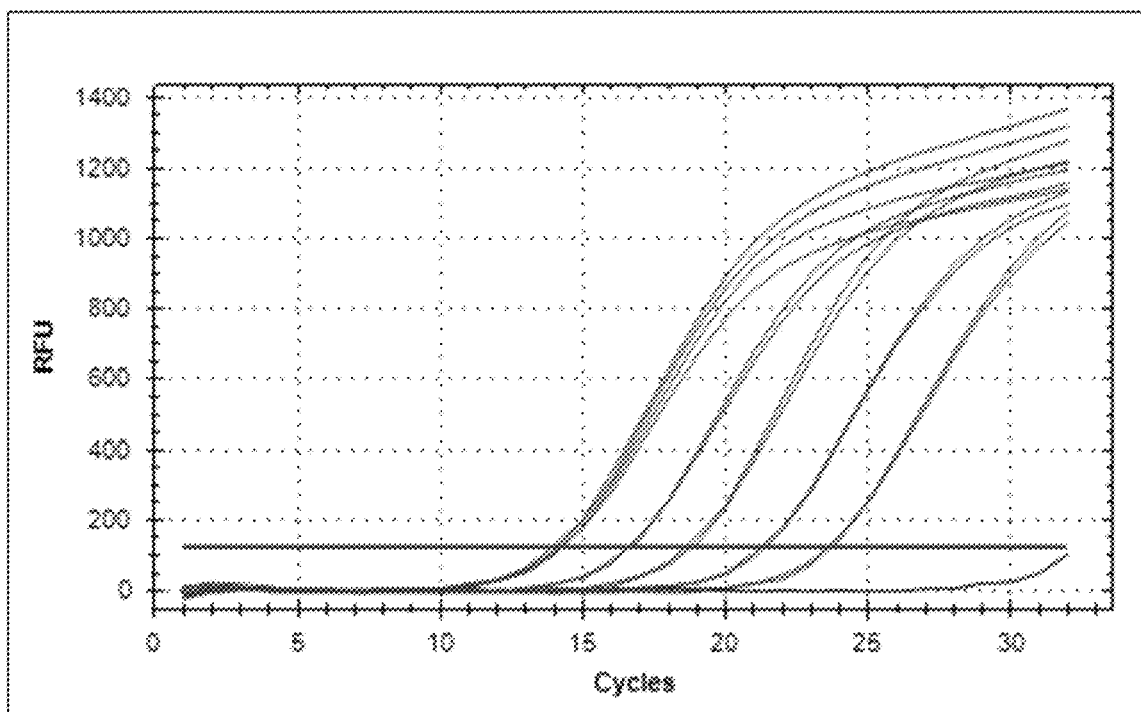
FIG. 15A shows an amplification plot for the Yb8-120 target of a real-time PCR multiplex of the Yb8-120 and SVA-290 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.
Figure 15B:
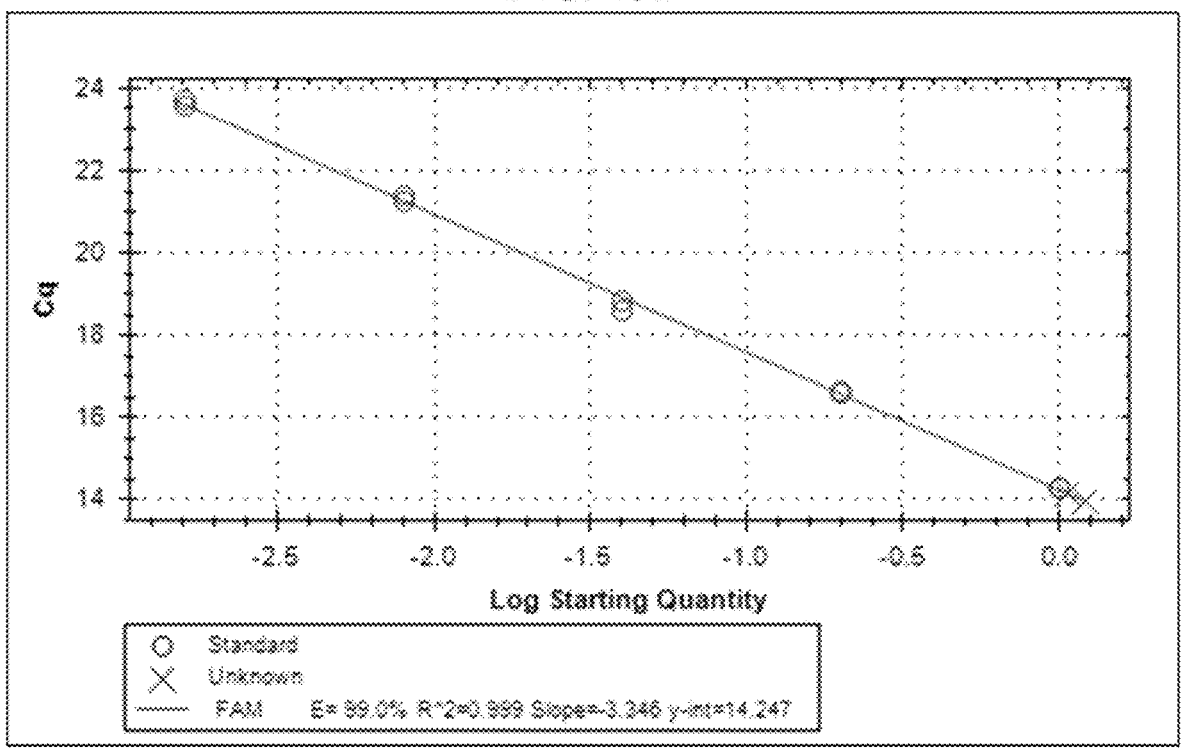
FIG. 15B shows a standard curve for the Yb8-120 target of a real-time PCR multiplex of the Yb8-120 and SVA-290 targets.
Figure 15C:
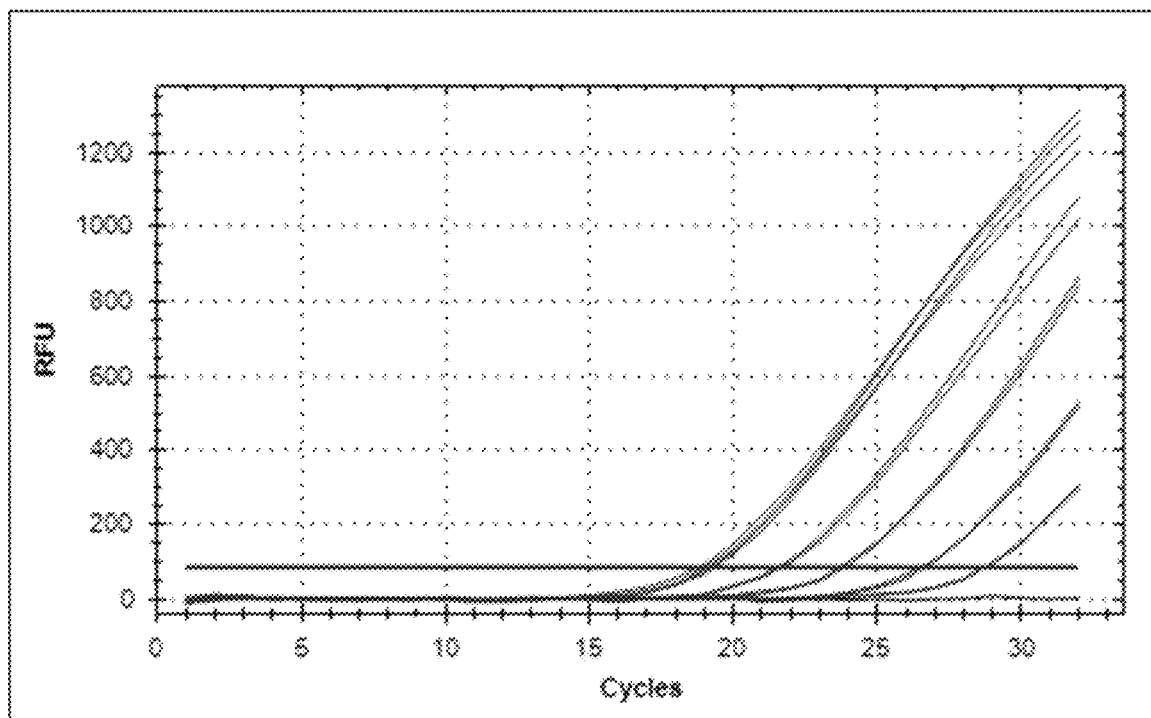
FIG. 15C shows an amplification plot for the SVA-290 target of a real-time PCR multiplex of the Yb8-120 and SVA-290 targets, the quantification of DNA in each sample being determined by use of a calibration curve with serial dilutions (1 ng, 200 pg, 40 pg, 8 pg, and 1.6 pg), with amplification of the SVA-290 target in purple, positive control in red and no template control in black.
Figure 15D:
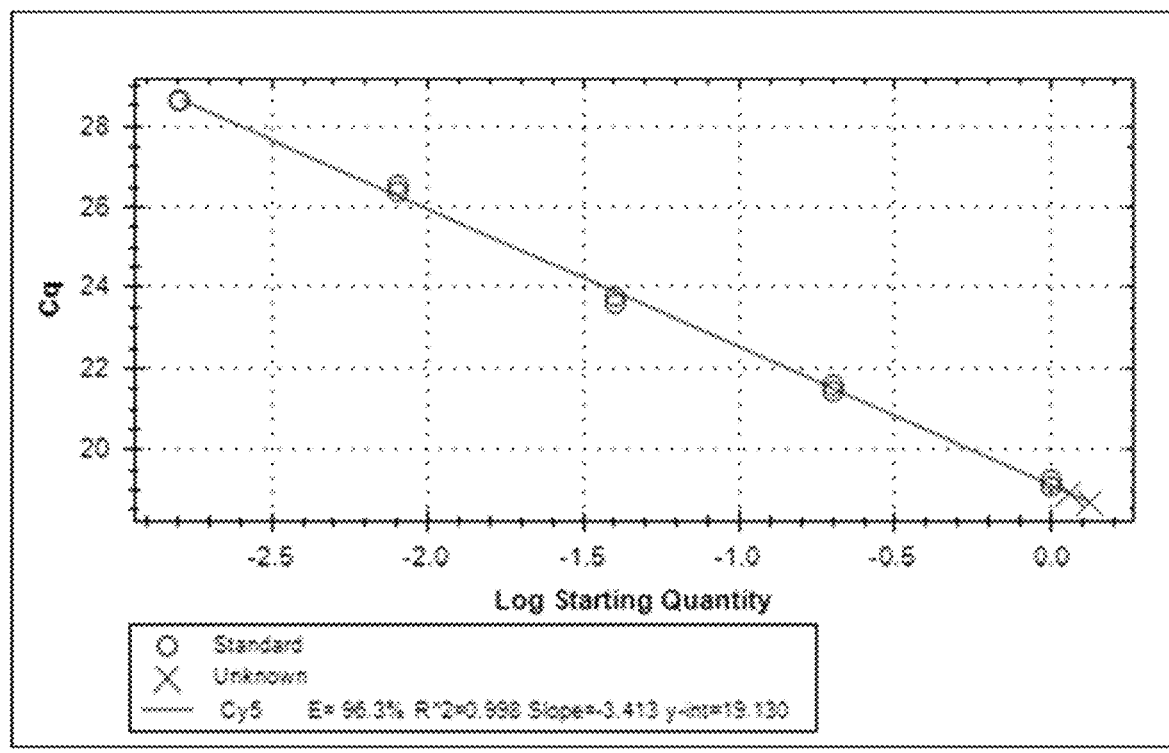
FIG. 15D shows a standard curve for the SVA-290 target of a real-time PCR multiplex of the Yb8-120 and SVA-290 targets.
Figure 15E:
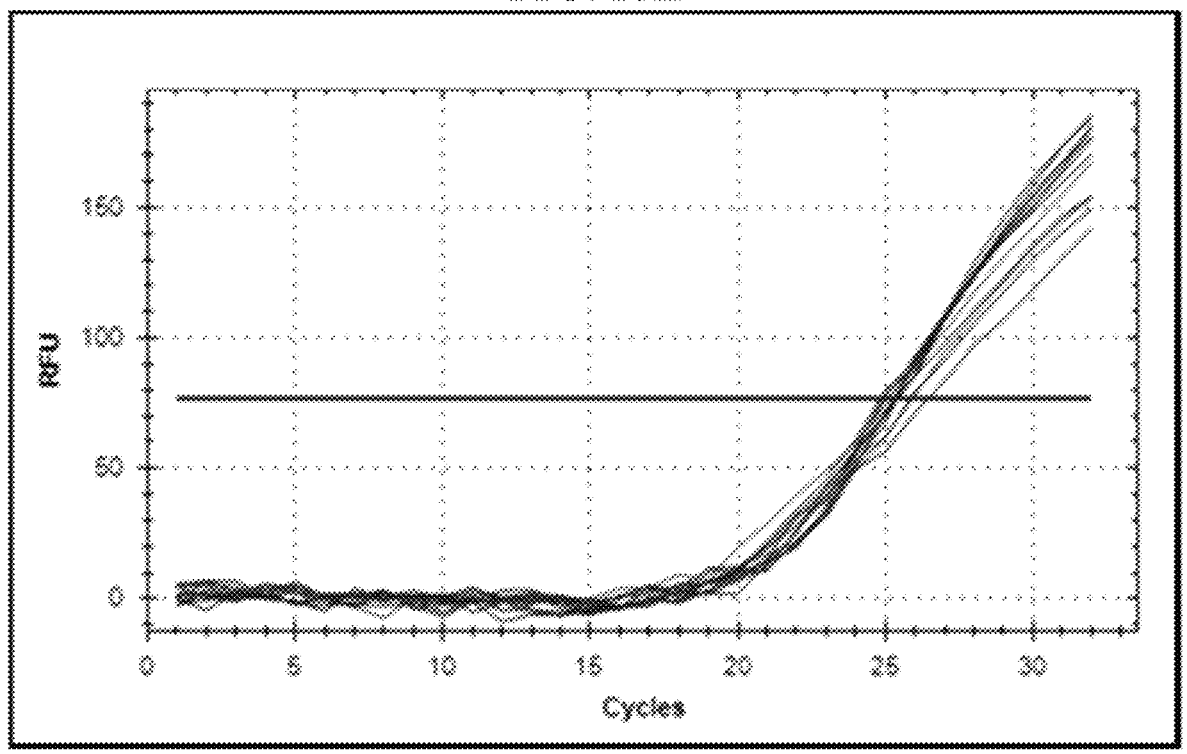
FIG. 15E shows an amplification plot of the internal positive control target within a real-time PCR multiplex of the Yb8-120 and SVA-290 targets, with amplification of the internal positive control target in blue.

Primers for our proposed targets ALU Yb8 and SVA were designed and tested. Two short ALU primer sets designed to produce amplicon lengths of 80 bp and 120 bp, among others, were developed for use in the multiplexed assay of the present invention. Four primer sets designed to produce amplicon lengths of 207 bp, 257 bp, 265 bp and 290 bp, among others, were developed using Primer 3 software and an SVA retrotransposon sequence. Because the SVA sequences are truncated in many individuals and also have sequence similarities with ALU sequences in certain regions, the target SVA sequence was selected from the SVA-R region, which has no or minimal sequence similarity as compared with the ALU sequence. FIG. 3 shows a schematic representation of the relative positions of the forward and reverse primers and the double labeled probes for both ALU-Yb8 and SVA sequences for qPCR analysis. The primer sequences are shown in Table 3. Any additional primer design may be done using Primer software (Koressaar, T; Remm, M, *Enhancements and modifications of primer design program Primer3*, Bioinformatics 23(10): 1289-91 (2007), doi: 10.1093/bioinformatics/btm091; Untergasser A, et al., *Primer3—new capabilities and interfaces*, Nucleic Acids Res. 40(15): e115 (2012), doi:10.1093/nar/gks596). Additionally, appropriate probes were developed for use in these amplifications. Probe sequences are shown in Table 4.

TABLE 3

Designed primers for ALU short and SVA long targets

| Marker Name | Target Size | Forward Primer | Reverse Primer |
|---|---|---|---|
| ALU | 80 | GGAAGCGGAGCTTGCAGTGA SEQ ID NO: 1 | AGACGGAGTCTCGCTCTGTCGC SEQ ID NO: 2 |
| ALU | 119 | AGACCATCCTGGCTAACAA SEQ ID NO: 3 | GCCATTCTCCTGCCTCA SEQ ID NO: 4 |
| ALU | 120 | TGGATCATGAGGTCAGGAGAT SEQ ID NO: 22 | CCGAGTAGCTGGGACTACA SEQ ID NO: 23 |
| ALU | 123 | ATCCTGGCTAACAAGGTCAAA SEQ ID NO: 5 | CGGGTTCACGCCATTCT SEQ ID NO: 6 |
| SVA | 207 | CTGTGTCCACTCAGGGTTAAAT SEQ ID NO: 7 | GAGGGAAGGTCAGCAGATAAAC SEQ ID NO: 8 |
| SVA | 257 | CCTGTGCTCTCTGAAACATGTGCT SEQ ID NO: 9 | GATTTGGCAGGGTCATGGGACAAT SEQ ID NO: 10 |
| SVA | 265 | ATGTGCTGTGTCCACTCAGGGTTA SEQ ID NO: 11 | ATTCTTGGGTGTTTCTCACAGAGG SEQ ID NO: 12 |
| SVA | 290 | TGGGATCCTGTTGATCTGTGACCT SEQ ID NO: 13 | GATTTGGCAGGGTCATGGGACAAT SEQ ID NO: 14 |
| SVA | 355 | GTTGCCGTGTCTGTGTAGAA SEQ ID NO: 24 | ATGGGACAATAGTGGAGGGA SEQ ID NO: 25 |
| SVA | 367 | CCGTGTCTGTGTAGAAAGAAGTAG SEQ ID NO: 26 | GGGATTTGGCAGGGTCAT SEQ ID NO: 27 |
| SVA | 399 | GGCGGCTTTGTGGAATAGA SEQ ID NO: 28 | GAGGGAAGGTCAGCAGATAAAC SEQ ID NO: 29 |
| SVA | 411 | TGGAATAGAAAGGCAGGAAGG SEQ ID NO: 30 | GCAGGGTCATGGGACAATAG SEQ ID NO: 31 |

TABLE 4

Designed probes for ALU short and SVA long targets

| Marker Name | Target Size | Probe |
|---|---|---|
| ALU | 80 | AGATTGCGCCACTGCAGTCCGCAGT SEQ ID NO: 15 |
| ALU | 119 | TGTAGTCCCAGCTACTCGGGAG SEQ ID NO: 16 |
| ALU | 120 | ACCATCCTGGCTAACAAGGTGAAACC SEQ ID NO: 32 |
| ALU | 123 | TGTAGTCCCAGCTACTCGGGAG SEQ ID NO: 17 |
| SVA | 207 | AAGGGCGGTGCAAGATGTGCTTTGTT SEQ ID NO: 18 |
| SVA | 257 | AAGGGCGGTGCAAGATGTGCTTTGTT SEQ ID NO: 19 |
| SVA | 265 | AAGGGCGGTGCAAGATGTGCTTTGTT SEQ ID NO: 20 |
| SVA | 290 | AAGGGCGGTGCAAGATGTGCTTTGTT SEQ ID NO: 21 |

TABLE 4-continued

Designed probes for ALU short and SVA long targets

| Marker Name | Target Size | Probe |
|---|---|---|
| SVA | 399 | ATCAGGGACACAAACACTGCGGAA SEQ ID NO: 33 |

Example 6

Optimization of Oligonucleotide Primers

Primers were evaluated by gel electrophoresis analysis of PCR products, noting the ability of each primer pair to produce a single PCR product when PCR amplification was carried out in the presence of human genomic DNA. Care was taken to ensure that no PCR amplification product was formed in the absence of genomic DNA. Primers were further evaluated using a SYBR green assay and melt curve analysis to examine the specificity of the PCR amplification. FIGS. 4 and 5 show exemplary SYBR green data in the form of an amplification plot, a standard curve, a melt curve and a melt peak (derivative melt curve) for the Yb8-119 and SVA-399 targets.

FIGS. 6 and 7 show the unacceptable SYBR green results obtained for the most common cell free DNA PCR biomarker, which includes ALU-115 and ALU-247 targets. Amplifications based on the ALU-115 and ALU-247 biomarkers were both unsuccessful as shown by primer dimer background in the no template controls.

Results obtained from SYBR green assays for particular primer pairs are summarized in Table 5 below:

TABLE 5

SYBR Green Assay Results for Individual Primer Pairs

| Primer Pair | Optimal Temperature | Results |
|---|---|---|
| Yb8-80 | 61° C. | High efficiency, low levels of DNA detected without any primer dimer background |
| Yb8-119 | 61° C. | Unsuitable due to high primer dimer background |
| Yb8-120 | 62.5° C. | High efficiency, low levels of DNA detected without any primer dimer background |
| SVA-207 | 61° C. | High efficiency, low levels of DNA detected without any primer dimer background |
| SVA-257 | 64° C. | High efficiency, low levels of DNA detected without any primer dimer background |
| SVA-265 | 57° C. | High efficiency, low levels of DNA detected without any primer dimer background |
| SVA-290 | 64° C. | High efficiency, low levels of DNA detected with very low levels of primer dimer background |
| SVA-367 | — | Unsuitable due to high primer dimer background |
| SVA-399 | — | Unsuitable due to high primer dimer background |
| SVA-411 | — | Unsuitable due to high primer dimer background |
| ALU-115 | 64° C. | Primer pairs reported in the prior art indicated high primer dimer background and therefore are not optimal for this application |
| ALU-147 | 64° C. | Primer pair reported in the prior art indicated high primer dimer background and therefore is not optimal for this application |

Example 7

Procedure for qPCR

The qPCR assays may be run on an Applied Biosystems 7500 Real Time PCR instrument and/or the Biorad CFX, but useful instrument platforms are not limited thereto. The qPCR assays of the present invention may be adapted to work on most Real-Time PCR instruments. To assess the concentration and integrity index of serum and plasma circulating cfDNA, both short and long fragments may be amplified and quantified. The short fragment primer sets may amplify the short (apoptotic) DNA fragments, whereas the long fragment primer sets may amplify the long (non-apoptotic) DNA fragments. The RE-qPCR multiplex reaction may contain three targets in a Taqman based assay: a short RE target, a long RE target, and a synthetic IPC sequence. The hybridization probes detecting each target may be labeled with different fluorophores (e.g. FAM, Cy5, or Cy3) to enable simultaneous detection. The following PCR conditions may be used, but they can be modified as necessary: 10 min 95° C. denaturation cycle, followed by 32 cycles of 2-step qPCR (15 s at 95° C. and 2 min at 61° C. combined annealing/extension time) at maximum ramp speed. Additional PCR parameters (i.e. cycle number, denaturation and annealing/extension times and temperatures) are investigated to obtain a robust, sensitive qPCR multiplex.

'Short' Yb8 and 'long' SVA primer pairs selected from those shown in Table 3 above were combined into eight different multiplex sets (Yb8-80 & SVA-207, Yb8-80 & SVA-257, Yb8-80 & SVA-265, Yb8-80 & SVA-290, Yb8-120 & SVA-207, Yb8-120 & SVA-257, Yb8-120 & SVA-265, and Yb8-120 & SVA-290). The optimal temperature for each multiplex was determined by a temperature gradient ranging from 64.0° C. to 55.0° C. The concentration of primers and additives including DMSO and additional $MgCl_2$ were optimized for each multiplex set.

The reaction mixture of each multiplex Yb8-SVA-qPCR included a template, forward primer, reverse primer, fluorescent probe, Brilliant Multiplex QPCR Master Mix (Agilent) and the additives bovine serum albumin ('BSA'), dimethyl sulfoxide ('DMSO'), and magnesium chloride ('$MgCl_2$'). Real-time PCR amplification was performed with pre-cycling heat activation of DNA polymerase at 95° C. for 10 min followed by 32 cycles of denaturation at 95° C. for 15 sec and extension at 61-62.5° C. (depending on the multiplex set) in a CFX96 Touch Real-Time PCR Detection System (Bio-Rad Laboratories). The quantification of DNA in each sample was determined by use of a calibration curve with serial dilutions (5 ng/μL to 1.6 pg/μL). Selected results are shown in FIGS. 8-15.

Example 8

Procedure for qPCR Data Analysis and Quality Control

Data analysis may be performed utilizing the respective AB 7500 or BioRad CFX instrument software. Melt curve analysis may be generated using Qiagen's QuantiTect SYBR1 Green PCR Kit (Cat#204141) and operated using the Applied Biosystems 7500 Real Time PCR instrument. For each experiment, a freshly prepared 3-fold serial dilution of high molecular weight standard DNA (ranging from 10 ng/μL to 0.004 ng/μL) was run in duplicate on each plate to generate standard curves for the long and short targets. The standard curves are plotted $C_T$ vs. Delta $R_n$ (the fluorescence emission intensity of the reporter dye divided by the fluorescence emission intensity of the passive reference dye). Resultant DNA quantitation values are interpolated from the resulting linear standard curves. At least one negative No Template Control (NTC) is run on each plate. The ratio between DNA concentration of the long target divided by DNA concentration of the short target provides an indication as to the degree of DNA integrity for the quantified sample. DNA integrity index is calculated as the ratio of concentrations ([concentration of long RE marker]/[concentration of short RE marker]). Quality metrics, including PCR efficiencies (i.e. slope) of both short and long targets, Y-intercept values, and verification of no true amplification in negative controls was assessed.

Efficiencies and integrity indices (long/short ratio) for some of the multiplex sets named above are shown in Table 6. As noted in Table 5, the primer pairs that performed exceptionally well individually in the SYBR green assay were Yb8-80, Yb8-120, SVA-207. SVA-257, SVA-265, and SVA-290.

TABLE 6

Efficiencies and Integrity Indices for Selected Multiplex Sets

| Short Target | Long Target | Efficiency Short Target | Efficiency Long Target | Integrity Index |
|---|---|---|---|---|
| Yb8-80 | SVA-207 | 101.8% | 101.7% | 0.995 |
| Yb8-80 | SVA-257 | 99.4 | 90.5 | 1.041 |
| Yb8-80 | SVA-265 | 99.9 | 98.3 | 1.069 |
| Yb8-80 | SVA-290 | 101.2 | 99.3 | 1.089 |
| Yb8-120 | SVA-207 | 99.9 | 93.5 | 0.786 |
| Yb8-120 | SVA-257 | 105.3 | 95.0 | 1.15 |
| Yb8-120 | SVA-265 | 98.7 | 95.9 | 1.046 |
| Yb8-120 | SVA-290 | 99.0 | 96.3 | 1.12 |

While this invention has been particularly shown and described with reference to embodiments thereof, it will be understood by those skilled in the art that various changes in form and details may be made therein without, departing from the spirit and scope of the invention as defined by the appended claims.

What is claimed is:

1. A multiplexed method to quantitate the integrity of cell free human DNA, comprising:
    providing a sample of serum, plasma, or urine, the sample comprising cell free human DNA, the cell free human DNA originating from circulating cell free human DNA and comprising a short nucleic acid target sequence including less than 180 bp and a long nucleic acid target sequence including more than 180 bp, the short nucleic acid target sequence and the long nucleic acid target sequence being retrotransposable element genomic targets that are independent of each other and that do not have any substantial portion of their sequences in common;
    preparing a standard curve plot for each of the short nucleic acid target sequence and the long nucleic acid target sequence;
    using a quantitative polymerase chain reaction (qPCR) method to separately and simultaneously quantitate the short nucleic acid target sequence and the long nucleic acid target sequence, wherein the short nucleic acid target sequence is a fragment of an ALU element and the long nucleic acid target sequence is a fragment of a SVA element, obtaining for each quantitated nucleic acid target sequence a threshold cycle number;
    comparing each threshold cycle number with the respective standard curve to determine for each quantitated nucleic acid target sequence a quantity of the DNA fragment that was present in the cell free DNA found in the sample;
    calculating a ratio of the quantity of DNA based on the long nucleic acid target sequence to the quantity of DNA based on the short nucleic acid target sequence; and
    accepting the ratio as a measure of an integrity of the cell free human DNA in the sample.

2. The multiplexed method of claim 1, the retrotransposable element genomic targets each having a copy number in excess of 1000 copies per genome.

3. The multiplexed method of claim 1, further comprising step of
    adding a synthetic DNA sequence as an internal positive control prior to the using step, and
    preparing a standard curve for the internal positive control, quantitating the internal positive control in the using step, and utilizing the quantitative internal positive control result in the comparing step to improve the accuracy and reliability of the comparing step.

4. The multiplexed method of claim 3, further comprised of making a determination of the concentration of cell free DNA in the sample using the internal positive control, wherein the determination takes into account PCR inhibitors that may be present.

5. The multiplexed method according to claim 3, the internal positive control having a size of about 172 bp.

6. The multiplexed method of claim 1, further comprised of the steps of providing and using being carried out in a single tube.

7. The multiplexed method of claim 1, the method further comprising a step of deactivating or eliminating proteins that bind to the short nucleic acid fragment or the long nucleic acid fragment.

8. The multiplexed method of claim 1, the sample being of serum or plasma, the method further comprising a step of diluting the sample of serum or plasma with sterile water.

9. The multiplexed method of claim 8, further comprised of the dilution consisting of mixing one part of sample with 40 parts of sterile water by volume.

10. The multiplexed method of claim 1, the providing step further comprising providing a hybridization probe corresponding to the short nucleic acid fragment and a hybridization probe corresponding to the long nucleic acid fragment.

11. The multiplexed method of claim 10, each probe including an observable label.

12. The multiplexed method of claim 11, each observable label being a fluorescent label, the fluorescent labels being distinct from each other.

13. The multiplexed method of claim 1, the using step further comprising a step of separating amplification products obtained from the qPCR reaction using electrophoresis.

14. The multiplexed method of claim 1, the method further comprising a step of determining an optimum temperature for the qPCR reaction.

15. The multiplexed method of claim 1, the sample being from an individual who is suffering from cancer or who is at risk for developing cancer.

16. The multiplexed method according to claim 1, the short nucleic acid fragment being an ALU element of the Yb8 subfamily having a size of about 80 bp, the long nucleic acid fragment being an SVA element having a size of about 207 bp.

17. The multiplexed method according to claim 1, the short nucleic acid fragment being an ALU element having one of the sizes indicated below, the long nucleic acid fragment being an SVA element having one of the sizes indicated below, the qPCR method quantitating the nucleic acid fragments by amplifying them, the amplifications each making use of a forward primer and a reverse primer, the forward primers and the reverse primers for the short nucleic acid fragment and the long nucleic acid fragment being selected from those presented in the table below:

18. The multiplexed method according to claim 17, the amplification products being visualized by displacement of probes hybridized to the short nucleic acid fragment and the long nucleic acid fragment, respectively, the short nucleic acid fragment being an ALU element having one of the sizes indicated below, the long nucleic acid fragment being an SVA element having one of the sizes indicated below, the probes for the short nucleic acid fragment and the long nucleic acid fragment each including a nucleic acid sequence selected from those presented in the table below:

| Marker Name | Target Size (bp) | Probe |
|---|---|---|
| ALU | 80 | AGATTGCGCCACTGCAGTCCGCAGT SEQ ID NO: 15 |
| ALU | 120 | ACCATCCTGGCTAACAAGGTGAAACC SEQ ID NO: 32 |
| ALU | 123 | TGTAGTCCCAGCTACTCGGGAG SEQ ID NO: 17 |
| SVA | 207 | AAGGGCGGTGCAAGATGTGCTTTGTT SEQ ID NO: 18 |
| SVA | 257 | AAGGGCGGTGCAAGATGTGCTTTGTT SEQ ID NO: 19 |
| SVA | 265 | AAGGGCGGTGCAAGATGTGCTTTGTT SEQ ID NO: 20 |
| SVA | 290 | AAGGGCGGTGCAAGATGTGCTTTGTT. SEQ ID NO: 21 |

| Marker Name | Target Size (bp) | Forward Primer | Reverse Primer |
|---|---|---|---|
| ALU | 80 | GGAAGCGGAGCTTGCAGTGA SEQ ID NO: 1 | AGACGGAGTCTCGCTCTGTCGC SEQ ID NO: 2 |
| ALU | 120 | TGGATCATGAGGTCAGGAGAT SEQ ID NO: 22 | CCGAGTAGCTGGGACTACA SEQ ID NO: 23 |
| ALU | 123 | ATCCTGGCTAACAAGGTCAAA SEQ ID NO: 5 | CGGGTTCACGCCATTCT SEQ ID NO: 6 |
| SVA | 207 | CTGTGTCCACTCAGGGTTAAAT SEQ ID NO: 7 | GAGGGAAGGTCAGCAGATAAAC SEQ ID NO: 8 |
| SVA | 257 | CCTGTGCTCTCTGAAACATGTGCT SEQ ID NO: 9 | GATTTGGCAGGGTCATGGGACAAT SEQ ID NO: 10 |
| SVA | 265 | ATGTGCTGTGTCCACTCAGGGTTA SEQ ID NO: 11 | ATTCTTGGGTGTTTCTCACAGAGG SEQ ID NO: 12 |
| SVA | 290 | TGGGATCCTGTTGATCTGTGACCT SEQ ID NO: 13 | GATTTGGCAGGGTCATGGGACAAT SEQ ID NO: 14 |
| SVA | 355 | GTTGCCGTGTCTGTGTAGAA SEQ ID NO: 24 | ATGGGACAATAGTGGAGGGA. SEQ ID NO: 25 |

19. The multiplexed method of claim 1, the sample being provided without prior purification of nucleic acids.

* * * * *

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Forward primer for ALU80 short target

<400> SEQUENCE: 1
ggaagcggag cttgcagtga                                              20

<210> SEQ ID NO 2
<211> LENGTH: 22
<212> TYPE: DNA
<213> ORGANISM: Artificial Sequence
<220> FEATURE:
<223> OTHER INFORMATION: Reverse primer for ALU80 short target

<400> SEQUENCE: 2
agacggagtc tcgctctgtc gc                                           22

<210> SEQ ID NO 3
<211> LENGTH: 19
<212> TYPE: DNA
<213> ORGANISM: Artificial Sequence
<220> FEATURE:
<223> OTHER INFORMATION: Forward primer for ALU119 short target

<400> SEQUENCE: 3
agaccatcct ggctaacaa                                               19

<210> SEQ ID NO 4
<211> LENGTH: 17
<212> TYPE: DNA
<213> ORGANISM: Artificial Sequence
<220> FEATURE:
<223> OTHER INFORMATION: Reverse primer for ALU short target

<400> SEQUENCE: 4
```

```
gccattctcc tgcctca                                                    17

<210> SEQ ID NO 5
<211> LENGTH: 21
<212> TYPE: DNA
<213> ORGANISM: Artificial Sequence
<220> FEATURE:
<223> OTHER INFORMATION: Forward primer for ALU123 short target

<400> SEQUENCE: 5
atcctggcta acaaggtcaa a                                               21

<210> SEQ ID NO 6
<211> LENGTH: 17
<212> TYPE: DNA
<213> ORGANISM: Artificial Sequence
<220> FEATURE:
<223> OTHER INFORMATION: Reverse primer for ALU123 short target

<400> SEQUENCE: 6
cgggttcacg ccattct                                                    17

<210> SEQ ID NO 7
<211> LENGTH: 22
<212> TYPE: DNA
<213> ORGANISM: Artificial Sequence
<220> FEATURE:
<223> OTHER INFORMATION: Forward primer for SVA207 long target

<400> SEQUENCE: 7
ctgtgtccac tcagggttaa at                                              22

<210> SEQ ID NO 8
<211> LENGTH: 22
<212> TYPE: DNA
<213> ORGANISM: Artificial Sequence
<220> FEATURE:
<223> OTHER INFORMATION: Reverse primer for SVA207 long target

<400> SEQUENCE: 8
gagggaaggt cagcagataa ac                                              22

<210> SEQ ID NO 9
<211> LENGTH: 24
<212> TYPE: DNA
<213> ORGANISM: Artificial Sequence
<220> FEATURE:
<223> OTHER INFORMATION: Forward primer for SVA257 long target

<400> SEQUENCE: 9
cctgtgctct ctgaaacatg tgct                                            24

<210> SEQ ID NO 10
<211> LENGTH: 24
<212> TYPE: DNA
<213> ORGANISM: Artificial Sequence
<220> FEATURE:
<223> OTHER INFORMATION: Reverse primer for SVA257 long target

<400> SEQUENCE: 10
gatttggcag ggtcatggga caat                                            24

<210> SEQ ID NO 11
<211> LENGTH: 24
<212> TYPE: DNA
```

<213> ORGANISM: Artificial Sequence
<220> FEATURE:
<223> OTHER INFORMATION: Forward primer for SVA265 long target

<400> SEQUENCE: 11
atgtgctgtg tccactcagg gtta                                            24

<210> SEQ ID NO 12
<211> LENGTH: 24
<212> TYPE: DNA
<213> ORGANISM: Artificial Sequence
<220> FEATURE:
<223> OTHER INFORMATION: Reverse primer for SVA265 long target

<400> SEQUENCE: 12
attcttgggt gtttctcaca gagg                                            24

<210> SEQ ID NO 13
<211> LENGTH: 24
<212> TYPE: DNA
<213> ORGANISM: Artificial Sequence
<220> FEATURE:
<223> OTHER INFORMATION: Forward primer for SVA290 long target

<400> SEQUENCE: 13
tgggatcctg ttgatctgtg acct                                            24

<210> SEQ ID NO 14
<211> LENGTH: 24
<212> TYPE: DNA
<213> ORGANISM: Artificial Sequence
<220> FEATURE:
<223> OTHER INFORMATION: Reverse primer for SVA290 long target

<400> SEQUENCE: 14
gatttggcag ggtcatggga caat                                            24

<210> SEQ ID NO 15
<211> LENGTH: 25
<212> TYPE: DNA
<213> ORGANISM: Artificial Sequence
<220> FEATURE:
<223> OTHER INFORMATION: Probe for ALU80 short target

<400> SEQUENCE: 15
agattgcgcc actgcagtcc gcagt                                           25

<210> SEQ ID NO 16
<211> LENGTH: 22
<212> TYPE: DNA
<213> ORGANISM: Artificial Sequence
<220> FEATURE:
<223> OTHER INFORMATION: Probe for ALU119 short target

<400> SEQUENCE: 16
tgtagtccca gctactcggg ag                                              22

<210> SEQ ID NO 17
<211> LENGTH: 22
<212> TYPE: DNA
<213> ORGANISM: Artificial Sequence
<220> FEATURE:
<223> OTHER INFORMATION: Probe for ALU123 short target

<400> SEQUENCE: 17
tgtagtccca gctactcggg ag                                              22

<210> SEQ ID NO 18
<211> LENGTH: 26
<212> TYPE: DNA
<213> ORGANISM: Artificial Sequence
<220> FEATURE:
<223> OTHER INFORMATION: Probe for SVA207 long target

<400> SEQUENCE: 18
aagggcggtg caagatgtgc tttgtt                                          26

<210> SEQ ID NO 19
<211> LENGTH: 26
<212> TYPE: DNA
<213> ORGANISM: Artificial Sequence
<220> FEATURE:
<223> OTHER INFORMATION: Probe for SVA257 long target

<400> SEQUENCE: 19
aagggcggtg caagatgtgc tttgtt                                          26

<210> SEQ ID NO 20
<211> LENGTH: 26
<212> TYPE: DNA
<213> ORGANISM: Artificial Sequence
<220> FEATURE:
<223> OTHER INFORMATION: Probe for SVA265 long target

<400> SEQUENCE: 20
aagggcggtg caagatgtgc tttgtt                                          26

<210> SEQ ID NO 21
<211> LENGTH: 26
<212> TYPE: DNA
<213> ORGANISM: Artificial Sequence
<220> FEATURE:
<223> OTHER INFORMATION: Probe for SVA290 long target

<400> SEQUENCE: 21
aagggcggtg caagatgtgc tttgtt                                          26

<210> SEQ ID NO 22
<211> LENGTH: 21
<212> TYPE: DNA
<213> ORGANISM: Artificial Sequence
<220> FEATURE:
<223> OTHER INFORMATION: Forward primer for ALU120 short target

<400> SEQUENCE: 22
tggatcatga ggtcaggaga t                                               21

<210> SEQ ID NO 23
<211> LENGTH: 19
<212> TYPE: DNA
<213> ORGANISM: Artificial Sequence
<220> FEATURE:
<223> OTHER INFORMATION: Reverse primer for ALU120 short target

<400> SEQUENCE: 23
ccgagtagct gggactaca                                                  19

<210> SEQ ID NO 24
<211> LENGTH: 20
<212> TYPE: DNA
<213> ORGANISM: Artificial Sequence
<220> FEATURE:

```
<223> OTHER INFORMATION: Forward primer for SVA355 long target

<400> SEQUENCE: 24
gttgccgtgt ctgtgtagaa                                                20

<210> SEQ ID NO 25
<211> LENGTH: 20
<212> TYPE: DNA
<213> ORGANISM: Artificial Sequence
<220> FEATURE:
<223> OTHER INFORMATION: Reverse primer for SVA355 long target

<400> SEQUENCE: 25
atgggacaat agtggaggga                                                20

<210> SEQ ID NO 26
<211> LENGTH: 24
<212> TYPE: DNA
<213> ORGANISM: Artificial Sequence
<220> FEATURE:
<223> OTHER INFORMATION: Forward primer for SVA367 long target

<400> SEQUENCE: 26
ccgtgtctgt gtagaaagaa gtag                                           24

<210> SEQ ID NO 27
<211> LENGTH: 18
<212> TYPE: DNA
<213> ORGANISM: Artificial Sequence
<220> FEATURE:
<223> OTHER INFORMATION: Reverse primer for SVA367 long target

<400> SEQUENCE: 27
gggatttggc agggtcat                                                  18

<210> SEQ ID NO 28
<211> LENGTH: 19
<212> TYPE: DNA
<213> ORGANISM: Artificial Sequence
<220> FEATURE:
<223> OTHER INFORMATION: Forward primer for SVA399 long target

<400> SEQUENCE: 28
ggcggctttg tggaataga                                                 19

<210> SEQ ID NO 29
<211> LENGTH: 22
<212> TYPE: DNA
<213> ORGANISM: Artificial Sequence
<220> FEATURE:
<223> OTHER INFORMATION: Reverse primer for SVA399 long target

<400> SEQUENCE: 29
gagggaaggt cagcagataa ac                                             22

<210> SEQ ID NO 30
<211> LENGTH: 22
<212> TYPE: DNA
<213> ORGANISM: Artificial Sequence
<220> FEATURE:
<223> OTHER INFORMATION: Forward primer for SVA411 long target

<400> SEQUENCE: 30
tggaatagaa aggcaggaaa gg                                             22
```

```
<210> SEQ ID NO 31
<211> LENGTH: 20
<212> TYPE: DNA
<213> ORGANISM: Artificial Sequence
<220> FEATURE:
<223> OTHER INFORMATION: Reverse primer for SVA411 long target

<400> SEQUENCE: 31
gcagggtcat gggacaatag                                              20

<210> SEQ ID NO 32
<211> LENGTH: 26
<212> TYPE: DNA
<213> ORGANISM: Artificial Sequence
<220> FEATURE:
<223> OTHER INFORMATION: Probe for ALU120 short target

<400> SEQUENCE: 32
accatcctgg ctaacaaggt gaaacc                                       26

<210> SEQ ID NO 33
<211> LENGTH: 24
<212> TYPE: DNA
<213> ORGANISM: Artificial Sequence
<220> FEATURE:
<223> OTHER INFORMATION: Probe for SVA399 long target

<400> SEQUENCE: 33
atcagggaca caaacactgc ggaa                                         24
```